US007625725B1

(12) United States Patent
Hogrefe et al.

(10) Patent No.: US 7,625,725 B1
(45) Date of Patent: Dec. 1, 2009

(54) POLYMERASE ENHANCING FACTOR (PEF) EXTRACTS, PEF PROTEIN COMPLEXES, ISOLATED PEF PROTEINS, AND METHODS FOR PURIFYING AND IDENTIFYING THEM

(75) Inventors: Holly Hogrefe, San Diego, CA (US); Connie J. Hansen, San Diego, CA (US)

(73) Assignee: Stratagene California, La Jolla, CA (US)

( * ) Notice: Subject to any disclaimer, the term of this patent is extended or adjusted under 35 U.S.C. 154(b) by 170 days.

(21) Appl. No.: 09/631,613

(22) Filed: Aug. 4, 2000

Related U.S. Application Data

(60) Division of application No. 08/957,709, filed on Oct. 24, 1997, which is a continuation-in-part of application No. 08/822,774, filed on Mar. 21, 1997.

(51) Int. Cl.
*C12P 19/34* (2006.01)
(52) U.S. Cl. .................................... 435/91.2
(58) Field of Classification Search ............ 435/6, 435/194, 195, 91.1, 91.2; 536/24.1, 23.7
See application file for complete search history.

(56) References Cited

U.S. PATENT DOCUMENTS

| | | | |
|---|---|---|---|
| 4,376,110 A | 3/1983 | David et al. | |
| 4,683,202 A | 7/1987 | Mullis | |
| 4,795,699 A | 1/1989 | Tabor et al. | |
| 4,873,192 A | 10/1989 | Kunkel | |
| 4,921,794 A | 5/1990 | Tabor et al. | |
| 4,946,786 A | 8/1990 | Tabor et al. | |
| 5,001,050 A | 3/1991 | Blanco et al. | |
| 5,073,632 A | 12/1991 | Donovan et al. | |
| 5,075,216 A | 12/1991 | Innis et al. | |
| 5,079,352 A | 1/1992 | Gelfand et al. | |
| 5,210,036 A | 5/1993 | Comb et al. | |
| 5,262,529 A | 11/1993 | Dryja et al. | |
| 5,310,652 A | 5/1994 | Gelfand et al. | |
| 5,322,785 A | 6/1994 | Comb et al. | |
| 5,352,778 A | 10/1994 | Comb et al. | |
| 5,352,785 A | 10/1994 | Herzberg et al. | |
| 5,374,553 A | 12/1994 | Gelfand et al. | |
| 5,407,800 A | 4/1995 | Gelfand et al. ............... 435/6 |
| 5,422,239 A | 6/1995 | Wands et al. | |
| 5,427,928 A | 6/1995 | Slesarev ............... 435/91.5 |
| 5,436,149 A | 7/1995 | Barnes ............... 435/194 |
| 5,449,603 A * | 9/1995 | Nielson et al. ............... 435/6 |
| 5,466,591 A | 11/1995 | Abramson et al. | |
| 5,474,796 A | 12/1995 | Brennan | |
| 5,489,523 A | 2/1996 | Mathur | |
| 5,500,363 A | 3/1996 | Comb et al. | |
| 5,512,462 A | 4/1996 | Cheng | |
| 5,534,407 A | 7/1996 | Tabor et al. | |
| 5,545,552 A | 8/1996 | Mathur | |
| 5,556,772 A | 9/1996 | Sorge et al. ............... 435/91.2 |
| 5,605,824 A * | 2/1997 | Nielson et al. ............... 435/194 |
| 5,618,702 A | 4/1997 | Scanlon | |
| 6,183,997 B1 * | 2/2001 | Hogrefe ............... 435/91.2 |
| 6,333,165 B1 | 12/2001 | Hogrefe | |
| 6,379,553 B1 | 4/2002 | Hogrefe | |
| 6,410,277 B1 | 6/2002 | Barnes | |
| 6,444,428 B1 | 9/2002 | Hogrefe | |

FOREIGN PATENT DOCUMENTS

| | | |
|---|---|---|
| EP | 0 265 293 B1 | 4/1988 |
| EP | 0 386 857 B1 | 9/1990 |
| EP | 0 416 755 A1 | 3/1991 |
| EP | 0 502 589 A2 | 9/1992 |
| EP | 0 669 401 A2 | 8/1995 |
| EP | 0 669 401 A3 | 8/1995 |
| EP | 0 870 832 A1 | 10/1998 |
| EP | 0 997 530 A1 | 5/2000 |
| WO | WO 89/06691 A2 | 7/1989 |
| WO | WO 91/02090 A1 | 2/1991 |
| WO | WO 92/06188 A2 | 4/1992 |
| WO | WO 92/06200 A1 | 4/1992 |
| WO | WO 92/09689 A1 | 6/1992 |
| WO | WO 94/26766 A A1 | 11/1994 |
| WO | WO 97/37038 A1 | 10/1997 |
| WO | WO 98/42860 A1 | 10/1998 |
| WO | WO 99/00506 A1 | 1/1999 |
| WO | WO 01/09347 A2 | 2/2001 |
| WO | WO 01/09347 A3 | 2/2001 |
| WO | WO 01/16333 A1 | 3/2001 |

OTHER PUBLICATIONS

Lasken et al., "Archaebacterial DNA Polymerases Tightly Bind Uracil-containing DNA", Journal of Biological Chemistry, vol. 271, No. 30, pp. 17692-17696 (1996).*
Barnes, "PCR amplification of up to 35-kb DNA with high fidelity and high yield from λ bacteriophage templates", Proc. Natl. Acad. Sci., vol. 91,pp. 2216-2220 (1994).*
T.A. Brown, Molecular Biology LabFax. Biosis Scientific Publishers, Blackwell Scientific Publications, Madison, WI, pp. 140-153, Dec. 1991.*
Hogrefeet al. "Archael dUTPase enhances PCR amplifications with archeal DNA polymerases by preventing dUTP incorporation." *Proc. Natl. Acad. Sci. USA*, 99(2):596-601 (2002).
Lasken et al., "Archaebacterial DNA Polymerases Tightly Bind Uracil-containing DNA," *The Journal of Biological Chemistry*, 271(30):17692-17696 (1996).
Slupphaug et al., "Low Incorporation of dUMP by Some Thermostable DNA Polymerase May Limit Their Use in PCR Amplifications." *Analytical Biochemistry*, 211:164-169 (1993).

(Continued)

*Primary Examiner*—Gary Benzion
*Assistant Examiner*—Cynthia B Wilder

(57) ABSTRACT

The invention provides novel extracts, proteins, and complexes that improve the polymerization activity of nucleic acid polymerases. Included within the aspects of the invention are methods for identifying compositions with a polymerase enhancing activity, methods for purifying and using these compositions, and specific extracts, proteins, and complexes that function to enhance polymerase activity. As an example, specifically described is nucleotide and amino acid sequence information for *Pyrococcus furiousus* PEF (P45), which was used to produce a recombinant PEF.

4 Claims, 45 Drawing Sheets

OTHER PUBLICATIONS

Wang et al., "*dcd* (dCTP Deaminase) Gene of *Escherichia coil*: Mapping, Cloning, Sequencing, and Identification as a Locus of Supressors of Lethal *dut* (dUTPase) Mutations," *Journal of Bacteriology*, 174(17):5647-5653 (1992).

E.M.B.L. Database Accession No. Q02103 (1993).

E.M.B.L. Database Accession No. P44953 (1995).

Supplementary European Search Report, for corresponding EP 98911883, mailed Nov. 6, 2002.

Udy et al., "Microplate DNA Preparation, PCR Screening and Cell Freezing for Gene Targeting in Embryonic Stem Cells," *BioTechniques*, 17(5):887-894 (1994).

Office Action mailed Mar. 2, 1999, in U.S. Appl. No. 08/957,709, filed Oct. 24, 1997.

Amendment and Response to Mar. 2, 1999. Office Action filed Sep. 2, 1999, in U.S. Appl. No. 08/957,709, filed Oct. 24, 1997.

Office Action mailed Nov. 23, 1999, in U.S. Appl. No. 08/957,709, filed Oct. 24, 1997.

Response Under 37 C.F.R. § 1.116 filed Aug. 16, 2000, in U.S. Appl. No. 08/957,709, filed Oct. 24, 1997.

Advisory Action mailed Mar. 1, 2001, in U.S. Appl. No. 08/957,709, filed Oct. 24, 1997.

Office Action mailed Feb. 27, 2002, in U.S. Appl. No. 08/957,709, filed Oct. 24, 1997.

Amendment filed Jul. 29, 2002, in U.S. Appl. No. 08/957,709, filed Oct. 24, 1997.

Office Action mailed Oct. 8, 2002, in U.S. Appl. No. 08/957,709, filed Oct. 24, 1997.

Amendment filed Mar. 10, 2003, in U.S. Patent Application No. 08/957.709, filed Oct. 24. 1997.

Office Action mailed May 6, 2003, in U.S. Appl. No. 08/957,709, filed Oct. 24, 1997.

Amendment After Final filed Nov. 7, 2003, in U.S. Appl. No. 08/957,709, filed Oct. 24, 1997.

Advisory Action mailed Apr. 20, 2004, in U.S. Appl. No. 08/957,709, filed Oct. 24, 1997.

Amendment filed Sep. 13, 2004, in U.S. Appl. No. 08/957,709, filed Oct. 24, 1997.

Office Action mailed Nov. 18, 2004, in U.S. Appl. No. 08/957,709, filed Oct. 24, 1997.

Amendment filed May 18, 2005, in U.S. Appl. No. 08/957,709, filed Oct. 24, 1997.

Office Action mailed Aug. 9, 2005, in U.S. Appl. No. 08/957,709, filed Oct. 24, 1997.

Office Action mailed Mar. 25, 2003, in U.S. Appl. No. 09/631,614, filed Aug. 4, 2000.

Amendment filed Aug. 25, 2003, in U.S. Appl. No. 09/631,614, filed Aug. 4. 2000.

Amendment (replacement) dated Nov. 3, 2003, in U.S. Appl. No. 09/631,614, filed Aug. 4, 2000.

Office Action mailed Dec. 29, 2003, in U.S. Appl. No. 09/631.614, filed Aug. 4, 2000.

Amendment After Final filed Apr. 29. 2004, in U.S. Appl. No. 09/631.614, filed Aug. 4, 2000.

Advisory Action mailed May 27. 2004, in U.S. Appl. No. 09/631,614, filed Aug. 4, 2000.

Office Action mailed Jul. 21, 2004, in U.S. Appl. No. 09/631,614, filed Aug. 4, 2000.

Amendment filed Jan. 21, 2005. In U.S. Appl. No. 09/631.614, filed Aug. 4, 2000.

Office Action mailed Apr. 20, 2005, in U.S. Appl. No. 09/631,614, filed Aug. 4. 2000.

Albrecht et al., Swiss-Prot accession No. Q01034, Apr. 1, 1993.

Anonymous, "Recombinant Vent$^R$198 DNA Polymerase," *The Neb Transcript*, vol. 3, No. 1, p. 4 (1991).

Attachment for 20XSSC—*cDNA Hybridization protocol using GeneTac Hybridization Unit*.

Baker et al., "Polymerases and the replisome: machines within machines," *Cell*, 92:295-305, 1998.

Barnes, "The fidelity of *Taq* polymerase catalyzing PCR is improved by an N-terminal deletion," *Gene*, 112: 29-35 (1992).

Bork, "Powers and Pitfalls in Sequence Analysis: The 70% Hurdle," *Genome Research*, 10:398-400 (2000).

Branden et al., *Introduction to Protein Structure*, Garland Publishing Inc., New York, p. 247 (1991).

Broun et al., "Catalytic Plasticity of Fatty Acid Modification Enzymes Underlying Chemical Diversity of Plant Upids," *Science*, 282:1315-1317 (1998).

Bult et al., PIR accession No. D64437, Sep. 13, 1996.

Bult et al., PIR 68 accession No. F64353, Sep. 16, 1996.

Cheng et al., "Effective amplification of long targets from cloned inserts and human genomic DNA," *Proc. Natl. Acad. Sci. USA*, 91:5695-5699 (1994).

Clark et al. "Novel blunt-end addition reactions catalyzed by DNA Polymerase I of *Escherichia coli*," *J. Mol. Biol.*, 198:123-127 (1987).

Clark, "Novel non-templated nucleotide addition reactions catalyzed by procaryotic and eucaryotic DNA polymerases," *Nucl. Acids Res.*, 16:9677-9686 (1988).

Cohen et al., *Genomics*, 40(1):213-215 (1997).

Dabrowski et al., GenBank Accession No. AAR15897 (2003).

Deng et al., "Site-directed mutagenesis of virtually any plasmid by eliminating a unique site," *Anal. Bioch.*, 200:81-88(1992).

Eckert et al., "Effect of reaction pH on the fidelity and processivity of exonuclease-deficient klenow polymerase," *J. Biol Chem.*, 268:13462-13471 (1993).

Foord et al., "Long distance PCR" pp. 63-77 (1995), in *PCR Primer*, Dieffenbach and Dveksler, eds., Cold Spring Harbor Press.

Gadsden et al., Swiss-Prot accession No. P33317, Feb. 1, 1994.

Guo et al., "Protein tolerance to random amino acid change," *PNAS*, 101:9205-9210(2004).

Hall et al., "A rapid and efficient method for site-directed mutagenesis by PCR, using biotinylated universal primers and streptavidin-coated magnetic beads," *Prot. Eng.*, 4(5):601 (1991).

Hames et al., *Nucleic Acid Hybridization: a practical approach*, IRL Press Limited, Oxford, England, pp. 76-82 (1985).

Hemsley et al., "A simple method for site-directed mutagenesis using the polymerase chain reaction," *Nucl. Acids Res.*, 17(16):6545-6551 (1989).

Henke et al., "Betaine Improves the PCR amplification of GC-rich DNA sequences," *Nucl. Acid Res.*, 25:3957-3958 (1997).

Ho et al. "Site-directed mutagenesis by overlap extension using the polymerase chain reaction," *Gene*, 77(1):51-59 (1989).

Hu, "DNA polymerase-catalyzed addition of nontemplated extra nucleotides to the 3' end of a DNA fragment," *DNA Cell Biol.*, 12(8):763-770 (1993).

Huang et al., "Fidelity and predominant mutations produced by deep vent wild-type and exonuclease-deficient DNA polymerases during *in vitro* DNA amplification," *DNA Cell Biol.*, 15:589-594 (1996).

Huang et al., "DNA polymerase C of the therrnophilic bacterium *Thennus aquaticus*: classification and phylogenetic analysis of the family C DNA polymerases," *J Mol. Evol.*, 48:756-69 (1999).

Hultman et al., "Solid phase *in vitro* mutagenesis using plasmid DNA template," *Nucl. Acids Res.*, 18(17):5107-5111 (1990).

Ishino et al., "A novel DNA polymerase family found in Archaea," *J. Bacteriol.*, 180:2232-36 (1998).

Jones et al., "DNA mutagenesis and recombination," *Nature*, 344:793-794 (1990).

Jones et al., "Recombinant circle PCR and recombination PCR for site-specific mutagenesis without PCR product purification," *BioTechniques*, 12(4):528-533 (1992).

Joyce et al., "Purification of *Escherichia coli* DNA polymerase I and klenow fragment," *Meth. Enzymol.*; 262:3-13 (1995).

Kellog et al., "TagStart Antibody™: 'Hot start' PCR facilitated by a neutralizing monoclonal antibody directed against *Taq* DNA polymerase," *BioTechniques*, 16:1134-1137 (1994).

Kennell, "Principles and practices of nucleic acid hybridization," *Prog. Nucl. Acid. Res. Mol. Biol.* 11:259-301 (1971).

Kletzin, Swiss-Prot accession No. Q02103, Apr. 1, 1993.

Kohler et al., "Development of a short-term, in vivo mutagenesis assay: the effects of methylation on the recovery of a lambda phage shuttle vector from transgenic mice," *Nucl. Acid Res.*, 18:3007-3013 (1990).

Kristjansson, *Themiophilic* Bacteria, CCR Press, Inc. (1992).

Kunkel, "Rapid and efficient site-specific mutagenesis without phenotypic selection," *Proc. Natl. Acad. Sci, USA.*, 82:488-492(1985).

Landre et al., "The use of cosolvents to enhance amplification by the polymerase chain reaction,"*In PCR Strategies*, M. Innis et al., eds. Academic Press, Inc., San Diego, CA, pp. 3-16 (1995).

Landt et al., "A general method for rapid site-directed mutagenesis using the polymerase chain reaction," *Gene*, 96:125-128 (1990).

Lawyer et al., "High-level expression, purification, and enzymatic characterization of full-length *Thermus aquaticus* DNA polymerase and a truncated form deficient in 5' to 3' exonuclease activity," *PCR Meth. And Appl.*, 2:275-87 (1993).

Lehninger et al., *Principles of Biochemistry*, Second Edition, published by Worth Publishers, New York, New York, pp. 822-824 (1993).

Livingston et al., "Affinity chromatography of avian type C viral reverse transcriptase: studies with Rous Sarcoma virus transformed rat cells," *Virology*, 50:388-95(1972).

Lundberg et al., "High-fidelity amplification using a thermostable DNA polymerase isolated from *Pyrococcus furiosus*," *Gene*, 108:1-6 (1991).

Lundberg et al., Swiss-Prot accession No. P06968, Apr. 1, 1988.

Makinjemi et al., "A novel family of DNA-polymerase-associated B subunits," *Trends Biochem. Sci.*, 24:14-16 (1999).

Mattila et al., "Fidelity of DNA synthesis by the *Thermococcus litoralis* DNA polymerase—an extremely heat stable enzyme with proofreading activity," *Nucl. Acid Res.*, 19:4967-4973 (1991).

Mercer et al., Swiss-Prot accession No. P14597. Apr. 1, 1990.

Meinkoth et al., "*Hybridization analysis of DNA blots*," *Current Protocols in Molecular Biology*, pp. 2.10.1, 2.10.8-2.10.12 (2000).

McHenry et al., "Purification and characterization of DNA polymerase III," *J. BioL Chem.*, 257:2657-2663 (1982).

Morrison et al., "Eurkaryotic Dna polymerase amino acid sequence required for 3' — 5' exonuclease acitivity," Proc. Natl. Acad. Sci. USA, 88:9473-9477 (1991).

Nassal et al., "PCR-based site-directed mutagenesis using primers with mismatched 3'-ends," *Nucl. Acids Res.*, 18(10):3077-3078 (1990).

Nelson et al., "A general method of site-specific mutagenesis using a modification of the *Thermus aquaticus* polymerase chain reaction," *Anal. Biochem.*, 180:147-151 (1989).

Nieto et al., "Effects of temperature and pH on the regeneration of the amino groups of ovalbumin after modification with citraconic and dimethylmaleic anhydrides," *Biochem. Biophys. Acta.*, 749:204-210 (1983).

Ohler et al., "Optimization of long-distance PCR using a transposon-based model system," *PCR Meth. & Applic.*, 2:51-59 (1992).

Perler et al., "Thermostable DNA polymerases," *Adv. Prot. Chem.*, 48:377-435 (1996).

Perrion et al., "Proofreading by the ε subunit of *Escherichia coli* DNA polymerase III increases the fidelity of calf thymus DNA polymerase α," *Proc. Natl. Acad. Sci. USA*, 86:3085-3088 (1989).

Perrino et al., "Differential Extension of 3' mispairs is a major contribution to the high fidelity of calf thymus DNA polymerase-α," *J. Biol. Chem.*, 264(5):2898-2905 (1989).

Perrino et al., "Hydrolosis of 3'-terminal mispairs in vitro by the 3'—5' exonuclease of DNA polymerase δ permits subsequent extension by DNA polymerase α," Biochem., 29: 5226-5231 (1990).

Prangishvili et al., "Biochemical and phylogenetic characterization of the dUTPase from the archaeal virus SIRV," *J. Biol. Chem.*, 273:6024-6029 (1998).

Robb et al. eds., *Archea: A Laboratory Manual*, Cold Spring Harbor Press (1995).

Saiki et al., "Enzymatic amplification of β-globin genomic sequences and restriction site analysis for diagnosis of sickle cell anemia," *Science*, 230:1350-1354 (1985).

Sambrook et al., *Molecular Cloning*, Cold Spring Harbor Press (1989).

Sears et al., "CircumVent™ thermal cycle sequencing and alternative manual and automated DNA sequencing protocols using highly thermostable Vent$_R$™ (exo-) DNA polymerase," *BioTechniques*, 13(4):626-633 (1992).

Seffernick et al., *J. Bacteriol.*, 183(8):2405-2410 (2001).

Southworth et al., "Cloning of thermostable DNA polymerases from hyperthermophilic marine Archaea with emphasis on *Thennococcus* sp. 9°N-7 and mutations affecting 3'-5' exonuclease activity," *Proc. Natl. Acad. Sci. USA*, 93:5281-5285 (1996).

Taylor et al. "The rapid generation of oligonucleotide-directed mutations at high frequency using phosphorothioate-modified DNA," *Nucl. Acids Res.*, 13(24):8765-8775 (1985).

Tindall et al., "Fidelity of DNA synthesis by the *Thermus aquaticus* DNA polymerase," *Biochem.*, 27: 6008-6013 (1988).

Uemori et al., "Organization and nucleotide sequence of the DNA polymerase gene from the archaeon *Pyrococcus furiosus*," *Nucl. Acids Res.*, 21:259-65(1993).

Uemori et al., "A novel DNA polyemerase in the hyperthermophilic archaeon, *Pyrococcus furiosus*: gene cloning, expression, and characterization," *Genes to Cells*, 2:499-512 (1997).

Van de Loo et al., "An oleate 12-hydroxylase from *Ricinus communis* L. is a fatty acyl desaturase homolog," *Proc. Natl. Acad. Sci.*, 92:6743-6747 (1995).

Vallette et al., "Construction of mutant and chimeric genes using the polymerase chain reaction," *Nucleic Acids Research*, 17(2):723-733 (1989).

Vandeyar et al. "A simple and rapid method for the selection of oligodeoxynudeotide-directed mutants," *Gene*, 65:129-133 (1988).

Wang et al., Swiss-Prot accession No. P28248, Dec. 1, 1992.

Watkins et al., "A rapid method for site-specific mutagenesis using larger plasmids as templates," *BioTechniques*, 15(4):700-704 (1993).

Weiner et al., "A method for the site-directed mono- and multimutagenesis of double-stranded DNA," *Gene*, 126:35-41 (1993).

Witkowski et al., *Biochemistry*, 38:11643-11650 (1999).

Yao et al. "Site-directed mutagenesis of herpesvirus glycoprotein phosphorylation sites by recombination polymerase chain reaction," *PCR Methods and Applications*, 1:205-207 (1992).

Zhu et al. "The use of exonuclease III for polymerase chain reaction sterilization," *Nucl. Acids Res.*, 19(9):2511 (1991).

GenBank Accession No. U62891 and AAC51123.

Amendment filed Jun. 9, 2006, in U.S. Appl. No. 08/957,709, filed Oct. 24, 1997.

Office Action mailed Aug. 24, 2006, in U.S. Appl. No. 08/957,709, filed Oct. 24, 1997.

Office Action mailed Jun. 2, 2006, in U.S. Appl. No. 101738,917, filed Dec. 16, 2003.

Sarkar, Gobinda et al., "Formamide can dramatically improve the specificity of PCT," *Nucleic Acids Research*, 18:7465 (1990).

Richter, Oliver-Matthias H. et al, "Cloning and sequencing of the gene for the cytoplasmic inorganic pyrophosphatase from the thermoacidophilic archaebacterium Thermoplasma acidophilum," *Eur. J. Biochem.*, 209:351-355 (1992).

Spitzer, Eric D. et al., "β-Alanine auxotrophy associated with dfp, a locus affecting DNA synthesis in *Escherichia coli,*" *Journal of Bacteriology*, 170:872-876 (1988).

Spitzer, Eric D. et al., "dfp gene of *Escherichia coli* K-12, a locus affecting DNA synthesis, codes for a flavoprotein," *Journal of Bacteriology*, 164:994-1003 (1985).

Kelman, Zvi et al., "Structural and functional similarities of prokaryotic and eukaryotic DNA polymerase sliding clamps,"*Nucleic Acids Research*, 23:3613-3620 (1995).

Takamatsu, Satoko et al., "Mismatch DNA recognition protein from an extremely thermophilic bacterium, Thermus thermophilus HB8," *Nucleic Acids Research*, 24:640-647 (1996).

Wagner, Robert et al., "Mutation detection using immobilized mismatch binding protein (MutS)," *Nucleic Acids Research*, 23:3944-3948 (1995).

Tabor, Stanley et al., "DNA sequence analysis with a modified bacteriophage T7 DNA polymerase," *Proc. Natl. Acad. Sci. USA*, 84:4767-4771 (1987).

Gottlieb, J. et al., "Interaction of Herpes Simplex Virus Type 1 DNA polymerase and the UL42 accessory protein with a model primer template," *Journal of Virology*, 68:4937-4945 (1994).

Tsurumi, Tatsuya et al., "Functional interaction between Epstein-Barr virus DNA polymerase catalytic subunit and its accessory subunit in vitro," *Journal of Virology*, 67:7648-7653 (1993).

Chevet, Eric et al., "Low concentrations of tetramethylammonium chloride increase yield and specificity of PCR," *Nucleic Acids Research*, 23:3343-3344 (1995).

Hung, Ted et al., "A specificity enhancer for polymerase chain reaction," *Nucleic Acids Research*, 18:4953 (1990).

Schwarz, Klaus et al., "Improved yields of long PCR products using gene 32 protein," *Nucleic Acids Research*, 18:1079 (1990).

Young, Mark C. et al., "Structure and function of the bacteriophage T4 DNA polymerase Holoenzyme," *Biochemistry*, 31:8675-8690 (1992).

Barnes, Wayne M., "PCR amplification of up to 35-kb DNA with high fidelity and high yield from lambda bacteriophage templates," *Proc. Natl. Acad. Sci. USA*, 91:2216-2220 (1994).

Oncor Fidelity DNA Sequencing System Product Profile, Aug. 1995.

* cited by examiner

Pfu "PCR ENHANCER" IN QUICKCHANGE MUTAGENESIS

| | LINEAR AMPLIFICATION CONDITIONS | | | TRANSFORMATION RESULTS | |
|---|---|---|---|---|---|
| POL. | BUFFER | H.S. #75 | AMPL. PROD. | #cfu | %MUTANTS |
| nPfu (#38) | nPfu | 0 | + | 84 | 95 |
| | | 1µl | ± | 47 | 87 |
| | | .1µl | + | 154 | 97 |
| | | .01µl | ++ | 632 | 95 |
| | | .001µl | + | 484 | 94 |
| nPfu (#24A) | nPfu | 0 | + | 94 | 89 |
| | | 1µl | + | 34 | 85 |
| | | .1µl | + | 173 | 91 |
| | | .01µl | ++ | 468 | 96 |
| | | .001µl | + | 230 | 90 |

*FIG. 39*

SEQUENCE LISTING

<160> NUMBER OF SEQ ID NOS: 89

<210> SEQ ID NO 1
<211> LENGTH: 15
<212> TYPE: PRT
<213> ORGANISM: Artificial Sequence
<220> FEATURE:
<223> OTHER INFORMATION: Primary N-terminal sequence of PEF protein
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid

<400> SEQUENCE: 1

Xaa Xaa Leu His His Val Lys Leu Ile Tyr Ala Thr Xaa Xaa Xaa
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Secondary N-terminal sequence of PEF
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 2

Xaa Xaa Xaa Pro Asp Trp Xaa Xaa Arg Xaa Glu Xaa Leu Xaa Xaa
1               5                   10                  15

<210> SEQ ID NO 3
<211> LENGTH: 35
<212> TYPE: PRT
<213> ORGANISM: Artificial Sequence
<220> FEATURE:
<223> OTHER INFORMATION: Primary sequence of P50
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature

```
<222> LOCATION: (21)..(21)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (32)..(35)
<223> OTHER INFORMATION: Xaa can be any naturally occurring amino acid

<400> SEQUENCE: 3

Xaa Leu Leu His His Val Lys Leu Ile Tyr Ala Thr Lys Xaa Arg Xaa
1               5                   10                  15

Leu Val Gly Lys Xaa Ile Val Leu Ala Ile Pro Gly Xaa Xaa Ala Xaa
            20                  25                  30

Xaa Xaa Xaa
        35

<210> SEQ ID NO 4
<211> LENGTH: 18
<212> TYPE: PRT
<213> ORGANISM: Artificial Sequence
<220> FEATURE:
<223> OTHER INFORMATION: Secondary sequence of P50
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(18)
<223> OTHER INFORMATION: Xaa can be any naturally occurring amino acid

<400> SEQUENCE: 4

Xaa Xaa Xaa Pro Asp Trp Xaa Xaa Arg Xaa Glu Xaa Leu Xaa Glu Xaa
1               5                   10                  15

Xaa Xaa

<210> SEQ ID NO 5
<211> LENGTH: 17
<212> TYPE: PRT
<213> ORGANISM: Artificial Sequence
<220> FEATURE:
<223> OTHER INFORMATION: Tryptic peptide 107/108
<220> FEATURE:
<221> NAME/KEY: misc_feature
<222> LOCATION: (1)..(1)
<223> OTHER INFORMATION: Xaa can be any naturally occurring amino acid

<400> SEQUENCE: 5

Xaa Trp Asp Ala Val Ile Met Ala Ala Ala Val Val Asp Phe Arg Pro
1               5                   10                  15

Lys
```

```
<210> SEQ ID NO 6
<211> LENGTH: 24
<212> TYPE: PRT
<213> ORGANISM: Artificial Sequence
<220> FEATURE:
<223> OTHER INFORMATION: Tryptic peptide 112

<400> SEQUENCE: 6

Ala Asp Leu Val Val Gly Asn Thr Leu Glu Ala Phe Gly Ser Glu Glu
1               5                   10                  15

Asn Gln Val Val Leu Ile Gly Arg
            20

<210> SEQ ID NO 7
<211> LENGTH: 17
<212> TYPE: PRT
<213> ORGANISM: Artificial Sequence
<220> FEATURE:
<223> OTHER INFORMATION: Peptide from PEF complex
<220> FEATURE:
<221> NAME/KEY: misc_feature
<222> LOCATION: (13)..(13)
<223> OTHER INFORMATION: Xaa can be any naturally occurring amino acid

<400> SEQUENCE: 7

Gly Ala Met Leu His His Val Lys Leu Ile Tyr Ala Xaa Lys Leu Arg
1               5                   10                  15

Lys

<210> SEQ ID NO 8
<211> LENGTH: 18
<212> TYPE: PRT
<213> ORGANISM: Artificial Sequence
<220> FEATURE:
<223> OTHER INFORMATION: Peptide from PEF complex
<220> FEATURE:
<221> NAME/KEY: misc_feature
<222> LOCATION: (15)..(16)
<223> OTHER INFORMATION: Xaa can be any naturally occurring amino acid

<400> SEQUENCE: 8

Gly Ala Met Leu His His Val Lys Leu Ile Tyr Ala Thr Lys Xaa Xaa
1               5                   10                  15

Arg Lys

<210> SEQ ID NO 9
<211> LENGTH: 13
<212> TYPE: PRT
<213> ORGANISM: Artificial Sequence
<220> FEATURE:
<223> OTHER INFORMATION: Peptide from PEF complex

<400> SEQUENCE: 9

Met Leu His His Val Lys Leu Ile Tyr Ala Thr Lys Leu
1               5                   10

<210> SEQ ID NO 10
<211> LENGTH: 16
<212> TYPE: PRT
<213> ORGANISM: Artificial Sequence
<220> FEATURE:
<223> OTHER INFORMATION: Peptide from PEF complex
<220> FEATURE:
<221> NAME/KEY: misc_feature
<222> LOCATION: (2)..(4)
<223> OTHER INFORMATION: Xaa can be any naturally occurring amino acid
```

```
<220> FEATURE:
<221> NAME/KEY: misc_feature
<222> LOCATION: (8)..(9)
<223> OTHER INFORMATION: Xaa can be any naturally occurring amino acid

<400> SEQUENCE: 10

Gly Xaa Xaa Xaa Pro Asp Trp Xaa Xaa Lys Phe Arg Lys Glu Glu Ser
1               5                   10                  15

<210> SEQ ID NO 11
<211> LENGTH: 17
<212> TYPE: PRT
<213> ORGANISM: Artificial Sequence
<220> FEATURE:
<223> OTHER INFORMATION: Peptide from PEF complex

<400> SEQUENCE: 11

Gly Ala Ile Leu Leu Pro Asp Trp Lys Ile Arg Lys Glu Ile Leu Ile
1               5                   10                  15

Glu

<210> SEQ ID NO 12
<211> LENGTH: 16
<212> TYPE: PRT
<213> ORGANISM: Artificial Sequence
<220> FEATURE:
<223> OTHER INFORMATION: Peptide from PEF complex
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 12

Xaa Met His His Val Ile Lys Leu Xaa Tyr Ala Thr Xaa Ser Arg Lys
1               5                   10                  15

<210> SEQ ID NO 13
<211> LENGTH: 18
<212> TYPE: PRT
<213> ORGANISM: Artificial Sequence
<220> FEATURE:
<223> OTHER INFORMATION: Peptide from PEF complex

<400> SEQUENCE: 13

Met Leu Tyr Leu Val Arg Pro Asp Trp Lys Arg Arg Lys Glu Ile Leu
1               5                   10                  15

Ile Glu

<210> SEQ ID NO 14
<211> LENGTH: 23
<212> TYPE: DNA
<213> ORGANISM: Artificial Sequence
<220> FEATURE:
<223> OTHER INFORMATION: Degenerate primer

<400> SEQUENCE: 14
caycaygaha arythattta cgc                                         23

<210> SEQ ID NO 15
```

```
<211> LENGTH: 23
<212> TYPE: DNA
<213> ORGANISM: Artificial Sequence
<220> FEATURE:
<223> OTHER INFORMATION: Degenerate primer
<220> FEATURE:
<221> NAME/KEY: misc_feature
<222> LOCATION: (9)..(9)
<223> OTHER INFORMATION: n is a, c, g, or t

<400> SEQUENCE: 15
gccatdatna cdgcrtcgta ttt                                              23

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide probe

<400> SEQUENCE: 16
caycaygaha arythatata cgc                                              23

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 17
ardacdacyt grttttcttc                                                  20

<210> SEQ ID NO 18
<211> LENGTH: 1209
<212> TYPE: DNA
<213> ORGANISM: Pyrococcus furiosus
<220> FEATURE:
<221> NAME/KEY: misc_feature
<222> LOCATION: (67)..(75)
<223> OTHER INFORMATION: n is a, c, g, or t
<220> FEATURE:
<221> NAME/KEY: misc_feature
<222> LOCATION: (930)..(933)
<223> OTHER INFORMATION: n is a, c, g, or t
<220> FEATURE:
<221> NAME/KEY: misc_feature
<222> LOCATION: (1203)..(1203)
<223> OTHER INFORMATION: n is a, c, g, or t

<400> SEQUENCE: 18
atgcttcacc acgtcaagct aatctacgcc acaaaaagtc gaaagctagt tggaaaaaag      60
atagtcnnnn nnnnnccagg gagtattgcg gctttggatg tgaaagcttg tgagggacta     120
attaggcatg gggccgaagt tcatgcagtg atgagtgagg cagccaccaa gataattcat     180
ccttatgcat ggaatttgcc cacgggaaat ccagtcataa ctgagatcac tggatttatc     240
gagcatgttg agttagcagg ggaacatgag aataaagcag atttaatttt ggtttgtcct     300
gccactgcca acacaattag taagattgca tgtggaatag atgatactcc agtaactaca     360
gtcgtgacca cagcatttcc ccacattcca attatgatag ccccagcaat gcatgagaca     420
atgtacaggc atcccatagt aagggagaac attgaaaggt taagaagctt ggcgttgag      480 tttataggac caagaattga ggagggaaag gcaaagttg caagcattga tgaaatagtt     540
tacagagtta ttaaaaacgt tccacaaaaaa acattggaag ggaagagagt cctagtaacg     600
gcgggagcaa caagagagta catagatcca ataagattca taacaaatgc cagcagtgga     660
```

-continued

```
aaaatgggag tagcgttggc tgaagaagca gattttagag gagctgttac cctcataaga    720
acaaagggaa gtgtaaaggc ttttagaatc agaaaaatca aattgaaggt tgagacagtg    780
gaagaaatgc tttcagcgat tgaaaatgag ttgaggagta aaaagtatga cgtagttatt    840
atggcagctg ctgtaagcga ttttaggcca aaaattaaag cagagggaaa aattaaaagc    900
ggaagatcaa taacgataga gctcgttccn nnnaatccca aaatcattga tagaataaag    960
gaaattcaac caaatgtctt tcttgttgga tttaaagcag aaacttcaaa agaaaagctt   1020
atagaagaag gtaaaaggca gattgagagg gccaaggctg acttagtcgt tggtaacaca   1080
ttggaagcct ttggaagcga ggaaaaccaa gtagtattaa ttggcagaga tttcacaaaa   1140
gaacttccaa aaatgaaaaa gagagagtta gcagagagaa tttgggatga gatagagaaa   1200 ttnctgtcc                                                           1209
```

<210> SEQ ID NO 19
<211> LENGTH: 403
<212> TYPE: PRT
<213> ORGANISM: Pyrococcus furiosus
<220> FEATURE:
<221> NAME/KEY: misc_feature
<222> LOCATION: (23)..(25)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (401)..(401)
<223> OTHER INFORMATION: Xaa can be any naturally occurring amino acid

<400> SEQUENCE: 19

```
Met Leu His His Val Lys Leu Ile Tyr Ala Thr Lys Ser Arg Lys Leu
1               5                   10                  15

Val Gly Lys Lys Ile Val Xaa Xaa Xaa Pro Gly Ser Ile Ala Ala Leu
            20                  25                  30

Asp Val Lys Ala Cys Glu Gly Leu Ile Arg His Gly Ala Glu Val His
        35                  40                  45

Ala Val Met Ser Glu Ala Ala Thr Lys Ile Ile His Pro Tyr Ala Trp
    50                  55                  60

Asn Leu Pro Thr Gly Asn Pro Val Ile Thr Glu Ile Thr Gly Phe Ile
65                  70                  75                  80

Glu His Val Glu Leu Ala Gly Glu His Glu Asn Lys Ala Asp Leu Ile
                85                  90                  95

Leu Val Cys Pro Ala Thr Ala Asn Thr Ile Ser Lys Ile Ala Cys Gly
            100                 105                 110

Ile Asp Asp Thr Pro Val Thr Thr Val Val Thr Thr Ala Phe Pro His
        115                 120                 125

Ile Pro Ile Met Ile Ala Pro Ala Met His Glu Thr Met Tyr Arg His
    130                 135                 140

Pro Ile Val Arg Glu Asn Ile Glu Arg Leu Lys Lys Leu Gly Val Glu
145                 150                 155                 160

Phe Ile Gly Pro Arg Ile Glu Glu Gly Arg Ala Lys Val Ala Ser Ile
                165                 170                 175

Asp Glu Ile Val Tyr Arg Val Ile Lys Lys Leu His Lys Lys Thr Leu
            180                 185                 190

Glu Gly Lys Arg Val Leu Val Thr Ala Gly Ala Thr Arg Glu Tyr Ile
        195                 200                 205
```

Asp Pro Ile Arg Phe Ile Thr Asn Ala Ser Ser Gly Lys Met Gly Val
    210                 215                 220

Ala Leu Ala Glu Glu Ala Asp Phe Arg Gly Ala Val Thr Leu Ile Arg
225                 230                 235                 240

Thr Lys Gly Ser Val Lys Ala Phe Arg Ile Arg Lys Ile Lys Leu Lys
                245                 250                 255

Val Glu Thr Val Glu Glu Met Leu Ser Ala Ile Glu Asn Glu Leu Arg
            260                 265                 270

Ser Lys Lys Tyr Asp Val Val Ile Met Ala Ala Val Ser Asp Phe
        275                 280                 285

Arg Pro Lys Ile Lys Ala Glu Gly Lys Ile Lys Ser Gly Arg Ser Ile
290                 295                 300

Thr Ile Glu Leu Val Pro Xaa Asn Pro Lys Ile Ile Asp Arg Ile Lys
305                 310                 315                 320

Glu Ile Gln Pro Asn Val Phe Leu Val Gly Phe Lys Ala Glu Thr Ser
                325                 330                 335

Lys Glu Lys Leu Ile Glu Glu Gly Lys Arg Gln Ile Glu Arg Ala Lys
            340                 345                 350

Ala Asp Leu Val Val Gly Asn Thr Leu Glu Ala Phe Gly Ser Glu Glu
        355                 360                 365

Asn Gln Val Val Leu Ile Gly Arg Asp Phe Thr Lys Glu Leu Pro Lys
    370                 375                 380

Met Lys Lys Arg Glu Leu Ala Glu Arg Ile Trp Asp Glu Ile Glu Lys
385                 390                 395                 400

Xaa Leu Ser

<210> SEQ ID NO 20
<211> LENGTH: 33
<212> TYPE: DNA
<213> ORGANISM: Artificial Sequence
<220> FEATURE:
<223> OTHER INFORMATION: Amplification primer

<400> SEQUENCE: 20
catagcgaat cgcaaaacc tttcgcggta tgg                    33

<210> SEQ ID NO 21
<211> LENGTH: 33
<212> TYPE: DNA
<213> ORGANISM: Artificial Sequence
<220> FEATURE:
<223> OTHER INFORMATION: Amplification primer

<400> SEQUENCE: 21
actacggaat tccacggaaa atgccgctca tcc                    33

<210> SEQ ID NO 22
<211> LENGTH: 20
<212> TYPE: DNA
<213> ORGANISM: Artificial Sequence
<220> FEATURE:
<223> OTHER INFORMATION: Amplification primer

<400> SEQUENCE: 22
ggcgtttccg ttcttcttcg                                   20

<210> SEQ ID NO 23
<211> LENGTH: 20
<212> TYPE: DNA

-continued

<213> ORGANISM: Artificial Sequence
<220> FEATURE:
<223> OTHER INFORMATION: Amplification primer

<400> SEQUENCE: 23
ccatctcacg cgccagtttc                                              20

<210> SEQ ID NO 24
<211> LENGTH: 23
<212> TYPE: DNA
<213> ORGANISM: Artificial Sequence
<220> FEATURE:
<223> OTHER INFORMATION: Amplification primer

<400> SEQUENCE: 24
gaggagagca ggaaaggtgg aac                                          23

<210> SEQ ID NO 25
<211> LENGTH: 21
<212> TYPE: DNA
<213> ORGANISM: Artificial Sequence
<220> FEATURE:
<223> OTHER INFORMATION: Amplification primer

<400> SEQUENCE: 25
gctgggagaa gacttcactg g                                            21

<210> SEQ ID NO 26
<211> LENGTH: 19
<212> TYPE: DNA
<213> ORGANISM: Artificial Sequence
<220> FEATURE:
<223> OTHER INFORMATION: Amplification primer

<400> SEQUENCE: 26
gagcttgctc aactttatc                                               19

<210> SEQ ID NO 27
<211> LENGTH: 23
<212> TYPE: DNA
<213> ORGANISM: Artificial Sequence
<220> FEATURE:
<223> OTHER INFORMATION: Amplification primer

<400> SEQUENCE: 27
gatagagata gtttctggag acg                                          23

<210> SEQ ID NO 28
<211> LENGTH: 23
<212> TYPE: DNA
<213> ORGANISM: Artificial Sequence
<220> FEATURE:
<223> OTHER INFORMATION: Amplification primer

<400> SEQUENCE: 28
cgggatatcg acatttctgc acc                                          23

<210> SEQ ID NO 29
<211> LENGTH: 24
<212> TYPE: DNA
<213> ORGANISM: Artificial Sequence
<220> FEATURE:
<223> OTHER INFORMATION: Amplification primer

<400> SEQUENCE: 29
gagttaaatg cctacactgt atct                                         24

-continued

```
<210> SEQ ID NO 30
<211> LENGTH: 24
<212> TYPE: DNA
<213> ORGANISM: Artificial Sequence
<220> FEATURE:
<223> OTHER INFORMATION: Amplification primer

<400> SEQUENCE: 30
caggactcag aagctgctat cgaa                                           24

<210> SEQ ID NO 31
<211> LENGTH: 24
<212> TYPE: DNA
<213> ORGANISM: Artificial Sequence
<220> FEATURE:
<223> OTHER INFORMATION: Amplification primer

<400> SEQUENCE: 31
ctgcacgtgc cctgtaggat ttgt                                           24

<210> SEQ ID NO 32
<211> LENGTH: 23
<212> TYPE: DNA
<213> ORGANISM: Artificial Sequence
<220> FEATURE:
<223> OTHER INFORMATION: Degenerate oligonucleotide probe
<220> FEATURE:
<221> NAME/KEY: misc_feature
<222> LOCATION: (15)..(15)
<223> OTHER INFORMATION: n is a, c, g, or t

<400> SEQUENCE: 32
ccagaytgga arwknaggaa aga                                            23

<210> SEQ ID NO 33
<211> LENGTH: 23
<212> TYPE: DNA
<213> ORGANISM: Artificial Sequence
<220> FEATURE:
<223> OTHER INFORMATION: Degenerate oligonucleotide probe
<220> FEATURE:
<221> NAME/KEY: misc_feature
<222> LOCATION: (15)..(15)
<223> OTHER INFORMATION: n is a, c, g, or t

<400> SEQUENCE: 33
ccagaytgga arwknagaaa aga                                            23

<210> SEQ ID NO 34
<211> LENGTH: 23
<212> TYPE: DNA
<213> ORGANISM: Artificial Sequence
<220> FEATURE:
<223> OTHER INFORMATION: Degenerate oligonucleotide probe
<220> FEATURE:
<221> NAME/KEY: misc_feature
<222> LOCATION: (15)..(15)
<223> OTHER INFORMATION: n is a, c, g, or t

<400> SEQUENCE: 34
ccagaytgga arwknaggaa gga                                            23

<210> SEQ ID NO 35
<211> LENGTH: 23
<212> TYPE: DNA
<213> ORGANISM: Artificial Sequence
<220> FEATURE:
```

-continued

<223> OTHER INFORMATION: Degenerate oligonucleotide probe
<220> FEATURE:
<221> NAME/KEY: misc_feature
<222> LOCATION: (15)..(15)
<223> OTHER INFORMATION: n is a, c, g, or t

<400> SEQUENCE: 35
ccagaytgga arwknagaaa gga                                              23

<210> SEQ ID NO 36
<211> LENGTH: 84
<212> TYPE: DNA
<213> ORGANISM: Pyrococcus furiosus
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t

<400> SEQUENCE: 36
cagagtgggc agagaggctn ttgttaaggg gaaattaatc gacgtggaaa aggaaggaaa      60
agtcgntatt cctccaaggg aata                                             84

<210> SEQ ID NO 37
<211> LENGTH: 27
<212> TYPE: PRT
<213> ORGANISM: Pyrococcus furiosus
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 37

Glu Trp Ala Glu Arg Leu Leu Leu Arg Gly Asn Xaa Ser Lys Trp Lys
1               5                   10                  15

Arg Lys Glu Lys Ser Xaa Phe Leu Gln Gly Asn
            20                  25

<210> SEQ ID NO 38
<211> LENGTH: 27
<212> TYPE: PRT
<213> ORGANISM: Pyrococcus furiosus
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 38

Arg Val Gly Arg Glu Ala Xaa Val Lys Gly Lys Leu Ile Glu Val Glu
1               5                   10                  15

Lys Glu Gly Lys Val Xaa Ile Pro Pro Arg Glu
            20                  25

<210> SEQ ID NO 39
<211> LENGTH: 28
<212> TYPE: PRT
<213> ORGANISM: Pyrococcus furiosus

```
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 39

Gln Ser Gly Gln Arg Gly Xaa Cys Xaa Gly Glu Ile Asn Arg Ser Gly
1               5                   10                  15

Lys Gly Arg Lys Ser Arg Tyr Ser Ser Lys Gly Leu
            20                  25

<210> SEQ ID NO 40
<211> LENGTH: 129
<212> TYPE: DNA
<213> ORGANISM: Pyrococcus furiosus

<400> SEQUENCE: 40
ctgcccactc tgaggtcata acctgctggt tggagccatt cttcagaaaa tggctctata      60
agtatttctt ttctgatttt ccagtctgga agtagcattt taccaccgaa acctttattt     120
ttaatttaa                                                             129

<210> SEQ ID NO 41
<211> LENGTH: 42
<212> TYPE: PRT
<213> ORGANISM: Pyrococcus furiosus
<220> FEATURE:
<221> NAME/KEY: misc_feature
<222> LOCATION: (1)..(1)
<223> OTHER INFORMATION: Xaa can be any naturally occurring amino acid

<400> SEQUENCE: 41

Xaa Ile Lys Asn Lys Gly Phe Gly Gly Lys Met Leu Leu Pro Asp Trp
1               5                   10                  15

Lys Ile Arg Lys Glu Ile Leu Ile Glu Pro Phe Ser Glu Glu Trp Leu
            20                  25                  30

Gln Pro Ala Gly Tyr Asp Leu Arg Val Gly
        35                  40

<210> SEQ ID NO 42
<211> LENGTH: 740
<212> TYPE: DNA
<213> ORGANISM: Pyrococcus furiosus
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (686)..(686)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t
<220> FEATURE:
<221> NAME/KEY: misc_feature
<222> LOCATION: (699)..(700)
<223> OTHER INFORMATION: n is a, c, g, or t
<220> FEATURE:
<221> NAME/KEY: misc_feature
```

```
<222> LOCATION: (703)..(703)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t

<400> SEQUENCE: 42
tcctccaagg gaatacgcct taatcctaac cctcgagagg ataaagttgc ccgacgatgt      60
tatgggggat atgaagataa ggagcagttt agcaagagaa ggggttattg gttcttttgc     120
ttgggttgac ccaggatggg atggaaactt aacactaatg ctctacaatg cctcaaatga     180
acctgtcgaa ttaagatatg gagagagatt tgtgcagatc gcatttataa ggctagaggg     240
tccggcaaga aacccttaca gaggaaacta tcaggggagc acaaggttag cgttttcaaa     300
gagaaagaaa ctctagcgtc ttttcaatag catcctcaat atctcgtgtg aagtaatcaa     360
tgtaaatact tgctgggtgg gttttttaggg attcaaactc gtaagatggg cctgtatagc    420
agaaaactat ttttgcctct tcttcattta tctttctgtg aataaaaaat ccaacatcca     480
cactagttcc aaaagatatt gtttgcgtga ttaccaacaa gatctggca ttattttga      540 tcttatactc tattctcctt tctccctcca atttgcccaa aataaacctg ggtagtatac    600
attcactcct ctcttttaaa ttcctataaa ttcgtacata gtttagaaaa atgtcaaatt    660
ctttnttccc tgttaaatta accncnaaat ctttatnann aancttttta taattcccaa    720 aaccctaat tttccccttn                                                 740

<210> SEQ ID NO 43
<211> LENGTH: 246
<212> TYPE: PRT
<213> ORGANISM: Pyrococcus furiosus
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (76)..(76)
```

```
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (232)..(234)
<223> OTHER INFORMATION: Xaa can be any naturally occurring amino acid
<220> FEATURE:
<221> NAME/KEY: misc_feature
<222> LOCATION: (237)..(237)
<223> OTHER INFORMATION: Xaa can be any naturally occurring amino acid
<220> FEATURE:
<221> NAME/KEY: misc_feature
<222> LOCATION: (246)..(246)
<223> OTHER INFORMATION: Xaa can be any naturally occurring amino acid

<400> SEQUENCE: 43

Leu Gln Gly Asn Thr Pro Xaa Ser Xaa Pro Ser Arg Gly Xaa Ser Cys
1               5                   10                  15

Pro Thr Met Leu Trp Gly Ile Xaa Arg Xaa Gly Ala Val Xaa Gln Glu
            20                  25                  30

Lys Gly Leu Leu Val Leu Leu Leu Gly Leu Thr Gln Asp Gly Met Glu
        35                  40                  45

Thr Xaa His Xaa Cys Ser Thr Met Pro Gln Met Asn Leu Ser Asn Xaa
    50                  55                  60

Asp Met Glu Arg Asp Leu Cys Arg Ser His Leu Xaa Gly Xaa Arg Val
65                  70                  75                  80

Arg Gln Glu Thr Leu Thr Glu Glu Thr Ile Arg Gly Ala Gln Gly Xaa
                85                  90                  95

Arg Phe Gln Arg Glu Arg Asn Ser Ser Val Phe Ser Ile Ala Ser Ser
```

-continued

```
                   100                 105                 110
Ile Ser Arg Val Lys Xaa Ser Met Xaa Ile Leu Ala Gly Trp Val Phe
            115                 120                 125

Arg Asp Ser Asn Ser Xaa Asp Gly Pro Val Xaa Gln Lys Thr Ile Phe
        130                 135                 140

Ala Ser Ser Ser Phe Ile Phe Leu Xaa Ile Lys Asn Pro Thr Ser Thr
145                 150                 155                 160

Leu Val Pro Lys Asp Ile Val Cys Val Ile Thr Asn Lys Ile Leu Ala
                165                 170                 175

Leu Phe Leu Ile Leu Tyr Ser Ile Leu Leu Ser Pro Ser Asn Leu Pro
            180                 185                 190

Lys Ile Asn Leu Gly Ser Ile His Ser Leu Leu Ser Phe Lys Phe Leu
        195                 200                 205

Xaa Ile Arg Thr Xaa Phe Arg Lys Met Ser Asn Ser Xaa Phe Pro Val
    210                 215                 220

Lys Leu Thr Xaa Lys Ser Leu Xaa Xaa Xaa Phe Leu Xaa Phe Pro Lys
225                 230                 235                 240

Pro Leu Ile Phe Pro Xaa
                245

<210> SEQ ID NO 44
<211> LENGTH: 246
<212> TYPE: PRT
<213> ORGANISM: Pyrococcus furiosus
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (228)..(229)
<223> OTHER INFORMATION: Xaa can be any naturally occurring amino acid
<220> FEATURE:
<221> NAME/KEY: misc_feature
<222> LOCATION: (232)..(234)
<223> OTHER INFORMATION: Xaa can be any naturally occurring amino acid

<400> SEQUENCE: 44

Pro Pro Arg Glu Tyr Ala Leu Ile Leu Thr Leu Glu Arg Ile Lys Leu
1               5                   10                  15

Pro Asn Asn Val Met Gly Asp Met Lys Ile Arg Ser Ser Leu Ala Arg
            20                  25                  30
```

Glu Gly Val Ile Gly Ser Phe Ala Trp Val Asp Pro Gly Trp Asp Gly
          35                  40                  45

Asn Leu Thr Leu Met Leu Tyr Asn Ala Ser Asn Glu Pro Val Glu Leu
 50                  55                  60

Arg Tyr Gly Glu Arg Phe Val Gln Ile Ala Phe Ile Arg Leu Glu Gly
 65                  70                  75                  80

Pro Ala Arg Asn Pro Tyr Arg Gly Asn Tyr Gln Gly Ser Thr Arg Leu
              85                  90                  95

Ala Phe Ser Lys Arg Lys Lys Leu Xaa Arg Leu Phe Asn Ser Ile Leu
             100                 105                 110

Asn Ile Ser Cys Glu Val Ile Asn Val Asn Thr Cys Trp Val Gly Phe
             115                 120                 125

Xaa Gly Phe Lys Leu Val Arg Trp Ala Cys Ile Ala Glu Asn Tyr Phe
130                 135                 140

Cys Leu Phe Phe Ile Tyr Leu Ser Val Asn Lys Lys Ser Asn Ile His
145                 150                 155                 160

Thr Ser Ser Lys Arg Tyr Cys Leu Arg Asp Tyr Gln Gln Asp Leu Gly
             165                 170                 175

Ile Ile Phe Asp Leu Ile Leu Tyr Ser Pro Phe Ser Leu Gln Phe Ala
             180                 185                 190

Gln Asn Lys Pro Gly Xaa Tyr Thr Phe Thr Pro Leu Phe Xaa Ile Pro
             195                 200                 205

Ile Asn Ser Tyr Ile Val Xaa Lys Asn Val Lys Phe Phe Xaa Pro Cys
             210                 215                 220

Xaa Ile Asn Xaa Xaa Ile Phe Xaa Xaa Xaa Leu Phe Ile Ile Pro Lys
225                 230                 235                 240

Thr Pro Asn Phe Pro Leu
             245

<210> SEQ ID NO 45
<211> LENGTH: 246
<212> TYPE: PRT
<213> ORGANISM: Pyrococcus furiosus
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (155)..(155)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid

```
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (229)..(229)
<223> OTHER INFORMATION: Xaa can be any naturally occurring amino acid
<220> FEATURE:
<221> NAME/KEY: misc_feature
<222> LOCATION: (233)..(235)
<223> OTHER INFORMATION: Xaa can be any naturally occurring amino acid
<220> FEATURE:
<221> NAME/KEY: misc_feature
<222> LOCATION: (243)..(243)
<223> OTHER INFORMATION: Xaa can be any naturally occurring amino acid

<400> SEQUENCE: 45

Ser Ser Lys Gly Ile Arg Leu Asn Pro Asn Pro Arg Glu Asp Lys Val
  1               5                  10                  15

Ala Arg Arg Cys Tyr Gly Gly Tyr Glu Asp Lys Glu Gln Phe Ser Lys
             20                  25                  30

Arg Arg Gly Tyr Trp Phe Phe Cys Leu Gly Xaa Pro Arg Met Gly Trp
         35                  40                  45

Lys Leu Asn Thr Asn Ala Leu Gln Cys Leu Lys Xaa Thr Cys Arg Ile
     50                  55                  60

Lys Ile Trp Arg Glu Ile Cys Ala Asp Arg Ile Tyr Lys Ala Arg Gly
 65                  70                  75                  80

Ser Gly Lys Lys Pro Leu Gln Arg Lys Leu Ser Gly Glu His Lys Val
                 85                  90                  95

Ser Val Phe Lys Glu Lys Glu Thr Leu Ala Ser Phe Gln Xaa His Pro
            100                 105                 110

Gln Tyr Leu Val Xaa Ser Asn Gln Cys Lys Tyr Leu Leu Gly Gly Phe
        115                 120                 125

Leu Gly Ile Gln Thr Arg Lys Met Gly Leu Tyr Ser Arg Lys Leu Phe
    130                 135                 140

Leu Pro Leu Leu His Leu Ser Phe Cys Glu Xaa Lys Ile Gln His Pro
145                 150                 155                 160

His Xaa Phe Gln Lys Ile Leu Phe Ala Xaa Leu Pro Thr Arg Ser Trp
                165                 170                 175

His Tyr Phe Xaa Ser Tyr Thr Leu Phe Ser Phe Leu Pro Pro Ile Cys
            180                 185                 190

Pro Lys Xaa Thr Trp Val Val Tyr Ile His Ser Ser Leu Leu Asn Ser
        195                 200                 205

Tyr Lys Phe Val His Ser Leu Glu Lys Cys Gln Ile Leu Xaa Ser Leu
    210                 215                 220

Leu Asn Xaa Pro Xaa Asn Leu Tyr Xaa Xaa Xaa Phe Tyr Asn Ser Gln
225                 230                 235                 240

Asn Pro Xaa Phe Ser Pro
                245

<210> SEQ ID NO 46
<211> LENGTH: 31
<212> TYPE: PRT
```

```
<213> ORGANISM: Pyrococcus furiosus
<220> FEATURE:
<221> NAME/KEY: misc_feature
<222> LOCATION: (23)..(25)
<223> OTHER INFORMATION: Xaa can be any naturally occurring amino acid

<400> SEQUENCE: 46

Met Leu His His Val Lys Leu Ile Tyr Ala Thr Lys Ser Arg Lys Leu
1               5                   10                  15

Val Gly Lys Lys Ile Val Xaa Xaa Xaa Pro Gly Ser Ile Ala Ala
            20                  25                  30

<210> SEQ ID NO 47
<211> LENGTH: 17
<212> TYPE: PRT
<213> ORGANISM: Pyrococcus furiousus

<400> SEQUENCE: 47

Lys Tyr Asp Val Val Ile Met Ala Ala Ala Val Ser Asp Phe Arg Phe
1               5                   10                  15

Lys

<210> SEQ ID NO 48
<211> LENGTH: 24
<212> TYPE: PRT
<213> ORGANISM: Pyrococcus furiosus

<400> SEQUENCE: 48

Ala Asp Leu Val Val Gly Asn Thr Leu Glu Ala Phe Gly Ser Glu Glu
1               5                   10                  15

Asn Gln Val Val Leu Ile Gly Arg
            20

<210> SEQ ID NO 49
<211> LENGTH: 21
<212> TYPE: DNA
<213> ORGANISM: Artificial Sequence
<220> FEATURE:
<223> OTHER INFORMATION: Amplification primer

<400> SEQUENCE: 49
ctattgagta cgaacgccat c                                          21

<210> SEQ ID NO 50
<211> LENGTH: 20
<212> TYPE: DNA
<213> ORGANISM: Artificial Sequence
<220> FEATURE:
<223> OTHER INFORMATION: Oligonucleotide probe

<400> SEQUENCE: 50
gtcacgcttg ctccactccg                                            20

<210> SEQ ID NO 51
<211> LENGTH: 437
<212> TYPE: PRT
<213> ORGANISM: Methanococcus jannaschii
<220> FEATURE:
<221> NAME/KEY: misc_feature
<222> LOCATION: (84)..(88)
<223> OTHER INFORMATION: Xaa can be any naturally occurring amino acid
<220> FEATURE:
<221> NAME/KEY: misc_feature
<222> LOCATION: (97)..(100)
<223> OTHER INFORMATION: Xaa can be any naturally occurring amino acid
<220> FEATURE:
```

```
<221> NAME/KEY: misc_feature
<222> LOCATION: (154)..(155)
<223> OTHER INFORMATION: Xaa can be any naturally occurring amino acid
<220> FEATURE:
<221> NAME/KEY: misc_feature
<222> LOCATION: (180)..(185)
<223> OTHER INFORMATION: Xaa can be any naturally occurring amino acid
<220> FEATURE:
<221> NAME/KEY: misc_feature
<222> LOCATION: (287)..(288)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (322)..(325)
<223> OTHER INFORMATION: Xaa can be any naturally occurring amino acid
<220> FEATURE:
<221> NAME/KEY: misc_feature
<222> LOCATION: (333)..(333)
<223> OTHER INFORMATION: Xaa can be any naturally occurring amino acid
<220> FEATURE:
<221> NAME/KEY: misc_feature
<222> LOCATION: (348)..(348)
<223> OTHER INFORMATION: Xaa can be any naturally occurring amino acid
<220> FEATURE:
<221> NAME/KEY: misc_feature
<222> LOCATION: (389)..(390)
<223> OTHER INFORMATION: Xaa can be any naturally occurring amino acid
<220> FEATURE:
<221> NAME/KEY: misc_feature
<222> LOCATION: (417)..(417)
<223> OTHER INFORMATION: Xaa can be any naturally occurring amino acid
<220> FEATURE:
<221> NAME/KEY: misc_feature
<222> LOCATION: (434)..(437)
<223> OTHER INFORMATION: Xaa can be any naturally occurring amino acid

<400> SEQUENCE: 51

Met Ile Ser Glu Ile Met His Pro Thr Lys Leu Leu Lys Gly Thr Lys
1               5                   10                  15

Ser Lys Leu Leu Glu Asn Lys Lys Ile Leu Val Ala Val Thr Ser Ser
            20                  25                  30

Ile Ala Ala Ile Glu Thr Pro Lys Leu Met Arg Glu Leu Ile Arg His
        35                  40                  45

Gly Ala Glu Val Tyr Cys Ile Ile Thr Glu Glu Thr Lys Lys Ile Ile
    50                  55                  60

Gly Lys Glu Ala Leu Lys Phe Gly Cys Gly Asn Glu Val Tyr Glu Glu
65                  70                  75                  80

Ile Thr Gly Xaa Xaa Xaa Xaa Xaa Asp Ile Glu His Ile Leu Leu Tyr
                85                  90                  95

Xaa Xaa Xaa Xaa Asn Glu Cys Asp Cys Leu Leu Ile Tyr Pro Ala Thr
            100                 105                 110

Ala Asn Ile Ile Ser Lys Ile Asn Leu Gly Ile Ala Asp Asn Ile Val
        115                 120                 125

Asn Thr Thr Ala Leu Met Phe Phe Gly Asn Lys Pro Ile Phe Ile Val
    130                 135                 140

Pro Ala Met His Glu Asn Met Phe Asn Xaa Xaa Ala Ile Lys Arg His
145                 150                 155                 160

Ile Asp Lys Leu Lys Glu Lys Asp Lys Ile Tyr Ile Ile Ser Pro Lys
                165                 170                 175
```

```
Phe Glu Glu Xaa Xaa Xaa Xaa Xaa Gly Lys Ala Lys Val Ala Asn
                180                 185                 190
Ile Glu Asp Val Val Lys Ala Val Ile Glu Lys Ile Gly Asn Asn Leu
            195                 200                 205
Lys Lys Glu Gly Asn Arg Val Leu Ile Leu Asn Gly Gly Thr Val Glu
        210                 215                 220
Phe Ile Asp Lys Val Arg Val Ile Ser Asn Leu Ser Ser Gly Lys Met
225                 230                 235                 240
Gly Val Ala Leu Ala Glu Ala Phe Cys Lys Glu Gly Phe Tyr Val Glu
                245                 250                 255
Val Ile Thr Ala Met Gly Leu Glu Pro Pro Tyr Tyr Ile Lys Asn His
            260                 265                 270
Lys Val Leu Thr Ala Lys Glu Met Leu Asn Lys Ala Ile Glu Xaa Xaa
        275                 280                 285
Leu Xaa Ala Lys Asp Phe Asp Ile Ile Ile Ser Ser Ala Ala Ile Ser
    290                 295                 300
Asp Phe Thr Val Glu Ser Xaa Phe Glu Gly Lys Leu Ser Ser Glu Glu
305                 310                 315                 320
Glu Xaa Xaa Xaa Xaa Leu Ile Leu Lys Leu Lys Arg Xaa Asn Pro Lys
                325                 330                 335
Val Leu Glu Glu Leu Arg Arg Ile Tyr Lys Asp Xaa Lys Val Ile Ile
            340                 345                 350
Gly Phe Lys Ala Glu Tyr Asn Leu Asp Glu Lys Glu Leu Ile Asn Arg
        355                 360                 365
Ala Lys Glu Arg Leu Asn Lys Tyr Asn Leu Asn Met Ile Ile Ala Asn
    370                 375                 380
Asp Leu Ser Lys Xaa Xaa His Tyr Phe Gly Asp Asp Tyr Ile Glu Val
385                 390                 395                 400
Tyr Ile Ile Thr Lys Tyr Glu Val Glu Lys Ile Ser Gly Ser Lys Lys
                405                 410                 415
Xaa Glu Ile Ser Glu Arg Ile Val Glu Lys Val Lys Lys Leu Val Lys
            420                 425                 430
Ser Xaa Xaa Xaa Xaa
        435

<210> SEQ ID NO 52
<211> LENGTH: 444
<212> TYPE: PRT
<213> ORGANISM: E. coli
<220> FEATURE:
<221> NAME/KEY: misc_feature
<222> LOCATION: (104)..(107)
<223> OTHER INFORMATION: Xaa can be any naturally occurring amino acid
<220> FEATURE:
<221> NAME/KEY: misc_feature
<222> LOCATION: (144)..(145)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (197)..(198)
<223> OTHER INFORMATION: Xaa can be any naturally occurring amino acid
<220> FEATURE:
<221> NAME/KEY: misc_feature
<222> LOCATION: (294)..(295)
<223> OTHER INFORMATION: Xaa can be any naturally occurring amino acid
<220> FEATURE:
<221> NAME/KEY: misc_feature
<222> LOCATION: (340)..(340)
```

<223> OTHER INFORMATION: Xaa can be any naturally occurring amino acid
<220> FEATURE:
<221> NAME/KEY: misc_feature
<222> LOCATION: (368)..(371)
<223> OTHER INFORMATION: Xaa can be any naturally occurring amino acid

<400> SEQUENCE: 52

```
Met Lys Ala Arg Gln Gln Lys Tyr Cys Asp Lys Ile Ala Asn Phe Trp
1               5                   10                  15

Cys His Pro Thr Gly Lys Ile Ile Met Ser Leu Ala Gly Lys Lys Ile
            20                  25                  30

Val Leu Gly Val Ser Gly Gly Ile Ala Ala Tyr Lys Thr Pro Glu Leu
        35                  40                  45

Val Arg Arg Leu Arg Asp Arg Gly Ala Asp Val Arg Val Ala Met Thr
50                  55                  60

Glu Ala Ala Lys Ala Phe Ile Thr Pro Leu Ser Leu Gln Ala Val Ser
65                  70                  75                  80

Gly Tyr Pro Val Ser Asp Ser Leu Leu Asp Pro Ala Ala Glu Ala Ala
                85                  90                  95

Met Gly His Ile Glu Leu Gly Xaa Xaa Xaa Xaa Lys Trp Ala Asp Leu
            100                 105                 110

Val Ile Leu Ala Pro Ala Thr Ala Asp Leu Ile Ala Arg Val Ala Ala
        115                 120                 125

Gly Met Ala Asn Asp Leu Val Ser Thr Ile Cys Leu Ala Thr Pro Xaa
130                 135                 140

Xaa Ala Pro Val Ala Val Leu Pro Ala Met Asn Gln Gln Met Tyr Arg
145                 150                 155                 160

Ala Ala Ala Thr Gln His Asn Leu Glu Val Leu Ala Xaa Ser Arg Gly
                165                 170                 175

Leu Leu Ile Trp Gly Pro Asp Ser Gly Ser Gln Ala Cys Gly Asp Ile
            180                 185                 190

Gly Pro Gly Arg Xaa Xaa Asp Pro Leu Thr Ile Val Asp Met Ala Val
        195                 200                 205

Ala His Phe Ser Pro Val Asn Asp Leu Lys His Leu Asn Ile Met Ile
210                 215                 220

Thr Ala Gly Pro Thr Arg Glu Pro Leu Asp Pro Val Arg Tyr Ile Ser
225                 230                 235                 240

Asn His Ser Ser Gly Lys Met Gly Phe Ala Ile Ala Ala Ala Ala Ala
                245                 250                 255

Arg Arg Gly Ala Asn Val Thr Leu Val Ser Gly Pro Val Ser Leu Pro
            260                 265                 270

Thr Pro Pro Phe Val Lys Arg Val Asp Val Met Thr Ala Leu Glu Met
        275                 280                 285

Glu Ala Ala Val Asn Xaa Xaa Ala Ser Val Gln Gln Gln Asn Ile Phe
290                 295                 300

Ile Gly Cys Ala Ala Val Ala Asp Tyr Arg Ala Ala Thr Val Ala Pro
305                 310                 315                 320

Glu Lys Ile Lys Lys Gln Ala Thr Gln Gly Asp Glu Leu Thr Ile Lys
                325                 330                 335

Met Val Lys Xaa Asn Pro Asp Ile Val Ala Gly Val Ala Ala Leu Lys
            340                 345                 350

Asp His Arg Pro Tyr Val Val Gly Phe Ala Ala Glu Thr Asn Asn Xaa
        355                 360                 365

Xaa Xaa Xaa Val Glu Glu Tyr Ala Arg Gln Lys Arg Ile Arg Lys Asn
370                 375                 380
```

-continued

Leu Asp Leu Ile Cys Ala Asn Asp Val Ser Gln Pro Thr Gln Gly Phe
385                 390                 395                 400

Asn Ser Asp Asn Ala Leu His Leu Phe Trp Gln Asp Gly Asp Lys
            405                 410                 415

Val Leu Pro Leu Glu Arg Lys Glu Leu Gly Gln Leu Leu Leu Asp
            420                 425                 430

Glu Ile Val Thr Arg Tyr Asp Glu Lys Asn Arg Arg
        435                 440

<210> SEQ ID NO 53
<211> LENGTH: 14
<212> TYPE: PRT
<213> ORGANISM: Pyrococcus furiosus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (11)..(14)
<223> OTHER INFORMATION: Xaa can be any naturally occurring amino acid

<400> SEQUENCE: 53

Xaa Gly Xaa Xaa Asp Xaa Xaa Xaa Xaa Gly Xaa Xaa Xaa Xaa
1               5                   10

<210> SEQ ID NO 54
<211> LENGTH: 14
<212> TYPE: PRT
<213> ORGANISM: Pyrococcus furiosus

<400> SEQUENCE: 54

Phe Ala Trp Val Asp Pro Gly Trp Asp Gly Asn Thr Leu Met
1               5                   10

<210> SEQ ID NO 55
<211> LENGTH: 14
<212> TYPE: PRT
<213> ORGANISM: Pyrococcus furiosus

<400> SEQUENCE: 55

Ala Gly Trp Ile Asp Ala Gly Phe Lys Gly Lys Ile Thr Leu
1               5                   10

<210> SEQ ID NO 56
<211> LENGTH: 14
<212> TYPE: PRT
<213> ORGANISM: Pyrococcus furiosus

<400> SEQUENCE: 56

Ser Ala Val His Asp Pro Gly Tyr Glu Gly Arg Pro Glu Tyr
1               5                   10

<210> SEQ ID NO 57
<211> LENGTH: 14
<212> TYPE: PRT
<213> ORGANISM: Pyrococcus furiosus

```
<400> SEQUENCE: 57

Pro Thr Ile Val Asp Ala Gly Phe Glu Gly Gln Leu Thr Ile
1               5                   10

<210> SEQ ID NO 58
<211> LENGTH: 14
<212> TYPE: PRT
<213> ORGANISM: Pyrococcus furiosus

<400> SEQUENCE: 58

Ala His Arg Ile Asp Pro Gly Trp Ser Gly Cys Ile Val Leu
1               5                   10

<210> SEQ ID NO 59
<211> LENGTH: 24
<212> TYPE: DNA
<213> ORGANISM: Artificial Sequence
<220> FEATURE:
<223> OTHER INFORMATION: Amplification primer

<400> SEQUENCE: 59
gagttaaatg cctacactgt atct                                      24

<210> SEQ ID NO 60
<211> LENGTH: 24
<212> TYPE: DNA
<213> ORGANISM: Artificial Sequence
<220> FEATURE:
<223> OTHER INFORMATION: Sequence used to design probes

<400> SEQUENCE: 60
caggactcag aagctgctat cgaa                                      24

<210> SEQ ID NO 61
<211> LENGTH: 24
<212> TYPE: DNA
<213> ORGANISM: Artificial Sequence
<220> FEATURE:
<223> OTHER INFORMATION: Oligonucleotide probe

<400> SEQUENCE: 61
ctgcacgtgc cctgtaggat ttgt                                      24

<210> SEQ ID NO 62
<211> LENGTH: 21
<212> TYPE: DNA
<213> ORGANISM: Artificial Sequence
<220> FEATURE:
<223> OTHER INFORMATION: Amplification primer

<400> SEQUENCE: 62
ctattgagta cgaacgccat c                                         21

<210> SEQ ID NO 63
<211> LENGTH: 20
<212> TYPE: DNA
<213> ORGANISM: Artificial Sequence
<220> FEATURE:
<223> OTHER INFORMATION: Amplification primer

<400> SEQUENCE: 63
gtcacgcttg ctccactccg                                           20

<210> SEQ ID NO 64
<211> LENGTH: 23
```

```
<212> TYPE: DNA
<213> ORGANISM: Artificial Sequence
<220> FEATURE:
<223> OTHER INFORMATION: Amplification primer

<400> SEQUENCE: 64
gaggagagca ggaaaggtgg aac                                          23

<210> SEQ ID NO 65
<211> LENGTH: 21
<212> TYPE: DNA
<213> ORGANISM: Artificial Sequence
<220> FEATURE:
<223> OTHER INFORMATION: Amplification primer

<400> SEQUENCE: 65
gctgggagaa gacttcactg g                                            21

<210> SEQ ID NO 66
<211> LENGTH: 8
<212> TYPE: PRT
<213> ORGANISM: Pyrococcus furiosus

<400> SEQUENCE: 66

His His Val Lys Leu Ile Tyr Ala
1               5

<210> SEQ ID NO 67
<211> LENGTH: 8
<212> TYPE: PRT
<213> ORGANISM: Pyrococcus furiosus

<400> SEQUENCE: 67

Lys Tyr Asp Ala Val Ile Met Ala
1               5

<210> SEQ ID NO 68
<211> LENGTH: 7
<212> TYPE: PRT
<213> ORGANISM: Pyrococcus furiosus

<400> SEQUENCE: 68

Glu Glu Asn Gln Val Val Leu
1               5

<210> SEQ ID NO 69
<211> LENGTH: 8
<212> TYPE: PRT
<213> ORGANISM: Pyrococcus furiosus

<400> SEQUENCE: 69

Pro Asp Trp Lys Ile Arg Lys Glu
1               5

<210> SEQ ID NO 70
<211> LENGTH: 471
<212> TYPE: DNA
<213> ORGANISM: Pyrococcus furiosus

<400> SEQUENCE: 70
atgctacttc cagactggaa aatcagaaaa gaaatactta tagagccatt ttctgaagaa      60
tcgctccaac cagcaggtta tgacctcaga gtgggcagag aggcttttgt taagggaaa      120 ttaatcgacg tggaaaagga aggaaaagtc gttattcctc caagggaata cgccttaatc     180
```

```
ctaaccctcg agaggataaa gttgcccgac gatgttatgg gggatatgaa gataaggagc    240
agtttagcaa gagaaggggt tattggttct tttgcttggg ttgacccagg atgggatgga    300
aacttaacac taatgctcta caatgcctca aatgaacctg tcgaattaag atatggagag    360
agatttgtgc agatcgcatt tataaggcta gagggtccgg caagaaaccc ttacagagga    420
aactatcagg ggagcacaag gttagcgttt tcaaagagaa agaaactcta g             471
```

<210> SEQ ID NO 71
<211> LENGTH: 156
<212> TYPE: PRT
<213> ORGANISM: Pyrococcus furiosus

<400> SEQUENCE: 71

```
Met Leu Leu Pro Asp Trp Lys Ile Arg Lys Glu Ile Leu Ile Glu Pro
1               5                   10                  15

Phe Ser Glu Glu Ser Leu Gln Pro Ala Gly Tyr Asp Leu Arg Val Gly
                20                  25                  30

Arg Glu Ala Phe Val Lys Gly Lys Leu Ile Asp Val Glu Lys Glu Gly
            35                  40                  45

Lys Val Val Ile Pro Pro Arg Glu Tyr Ala Leu Ile Leu Thr Leu Glu
        50                  55                  60

Arg Ile Lys Leu Pro Asp Asp Val Met Gly Asp Met Lys Ile Arg Ser
65                  70                  75                  80

Ser Leu Ala Arg Glu Gly Val Ile Gly Ser Phe Ala Trp Val Asp Pro
                85                  90                  95

Gly Trp Asp Gly Asn Leu Thr Leu Met Leu Tyr Asn Ala Ser Asn Glu
                100                 105                 110

Pro Val Glu Leu Arg Tyr Gly Glu Arg Phe Val Gln Ile Ala Phe Ile
            115                 120                 125

Arg Leu Glu Gly Pro Ala Arg Asn Pro Tyr Arg Gly Asn Tyr Gln Gly
        130                 135                 140

Ser Thr Arg Leu Ala Phe Ser Lys Arg Lys Lys Leu
145                 150                 155
```

<210> SEQ ID NO 72
<211> LENGTH: 13
<212> TYPE: PRT
<213> ORGANISM: Artificial Sequence
<220> FEATURE:
<223> OTHER INFORMATION: Consensus uridine binding sequence motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(13)
<223> OTHER INFORMATION: Xaa can be any naturally occurring amino acid

<400> SEQUENCE: 72

```
Xaa Gly Xaa Xaa Asp Xaa Xaa Xaa Gly Xaa Xaa Xaa Xaa
1               5                   10
```

<210> SEQ ID NO 73

-continued

```
<211> LENGTH: 14
<212> TYPE: PRT
<213> ORGANISM: Artificial Sequence
<220> FEATURE:
<223> OTHER INFORMATION: Artificial uridine binding motif

<400> SEQUENCE: 73

Phe Ala Trp Val Asp Pro Gly Trp Asp Gly Asn Thr Leu Met
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Artificial uridine binding motif

<400> SEQUENCE: 74

Ala Gly Trp Ile Asp Ala Gly Phe Lys Gly Lys Ile Thr Leu
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Artificial uridine binding motif

<400> SEQUENCE: 75

Ser Ala Val His Asp Pro Gly Tyr Glu Gly Arg Pro Glu Tyr
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Artificial uridine binding motif

<400> SEQUENCE: 76

Pro Thr Ile Val Asp Ala Gly Phe Glu Gly Gln Leu Thr Ile
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Artificial uridine binding motif

<400> SEQUENCE: 77

Ala His Arg Ile Asp Pro Gly Trp Ser Gly Cys Ile Val Leu
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Artificial uridine binding motif

<400> SEQUENCE: 78

Val Gly Leu Ile Asp Ser Asp Tyr Gln Gly Gln Leu Met Ile
1               5                   10

<210> SEQ ID NO 79
<211> LENGTH: 14
```

```
<212> TYPE: PRT
<213> ORGANISM: Artificial Sequence
<220> FEATURE:
<223> OTHER INFORMATION: Artificial uridine binding motif

<400> SEQUENCE: 79

Ala Gly Val Val Asp Arg Asp Tyr Thr Gly Glu Val Lys Val
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Artificial uridine binding motif

<400> SEQUENCE: 80

Ala Gly Val Ile Asp Glu Asp Tyr Arg Gly Asn Val Gly Val
1               5                   10

<210> SEQ ID NO 81
<211> LENGTH: 14
<212> TYPE: PRT
<213> ORGANISM: Artificial Sequence
<220> FEATURE:
<223> OTHER INFORMATION: Artificial uridine binding motif

<400> SEQUENCE: 81

Thr Gly Leu Ile Asp Pro Gly Phe Gln Gly Glu Leu Lys Leu
1               5                   10

<210> SEQ ID NO 82
<211> LENGTH: 33
<212> TYPE: DNA
<213> ORGANISM: Artificial Sequence
<220> FEATURE:
<223> OTHER INFORMATION: Amplification primer

<400> SEQUENCE: 82
gacgacgaca agatgctact tccagactgg aaa                           33

<210> SEQ ID NO 83
<211> LENGTH: 35
<212> TYPE: DNA
<213> ORGANISM: Artificial Sequence
<220> FEATURE:
<223> OTHER INFORMATION: Amplification primer

<400> SEQUENCE: 83
ggaacaagac ccgtcccact ttcacagatg aagag                         35

<210> SEQ ID NO 84
<211> LENGTH: 23
<212> TYPE: DNA
<213> ORGANISM: Artificial Sequence
<220> FEATURE:
<223> OTHER INFORMATION: Amplification primer

<400> SEQUENCE: 84
gaggagagca ggaaaggtgg aac                                      23

<210> SEQ ID NO 85
<211> LENGTH: 23
<212> TYPE: DNA
<213> ORGANISM: Artificial Sequence
<220> FEATURE:
<223> OTHER INFORMATION: Amplification primer
```

-continued

```
<400> SEQUENCE: 85
ctccatgtcc caactccgat cac                                              23

<210> SEQ ID NO 86
<211> LENGTH: 38
<212> TYPE: DNA
<213> ORGANISM: Artificial Sequence
<220> FEATURE:
<223> OTHER INFORMATION: Amplification primer

<400> SEQUENCE: 86
ggttttccca gtcacgacgt tgtaaaacga cggccagt                              38

<210> SEQ ID NO 87
<211> LENGTH: 38
<212> TYPE: DNA
<213> ORGANISM: Artificial Sequence
<220> FEATURE:
<223> OTHER INFORMATION: Amplification primer

<400> SEQUENCE: 87
gguuuuccca gucacgacgu uguaaaacga cggccagu                              38

<210> SEQ ID NO 88
<211> LENGTH: 35
<212> TYPE: DNA
<213> ORGANISM: Artificial Sequence
<220> FEATURE:
<223> OTHER INFORMATION: Amplification primer

<400> SEQUENCE: 88
gacgacgaca agatgccctg ctctgaagag acacc                                 35

<210> SEQ ID NO 89
<211> LENGTH: 35
<212> TYPE: DNA
<213> ORGANISM: Artificial Sequence
<220> FEATURE:
<223> OTHER INFORMATION: Amplification primer

<400> SEQUENCE: 89
ggaacaagac ccgtttaatt ctttccagtg gaacc                                 35
```

POLYMERASE ENHANCING FACTOR (PEF) EXTRACTS, PEF PROTEIN COMPLEXES, ISOLATED PEF PROTEINS, AND METHODS FOR PURIFYING AND IDENTIFYING THEM

This application is a division of application Ser. No. 08/957,709, filed Oct. 24, 1997, which is incorporated by reference for any purpose.

This application claims priority to and is a continuation-in-part of U.S. patent application Ser. No. 08/822,774, filed Mar. 21, 1997. The entire contents of that application are specifically incorporated herein by reference and may be relied on to make and use embodiments of the claimed invention.

BACKGROUND OF THE INVENTION

1. Field of the Invention

The invention relates to the fields of nucleic acid polymerases and nucleic acid polymerization reactions.

2. Introduction

The efficiency of a nucleic acid polymerization reaction has implications for numerous assays and techniques. For example, the ability to enhance polymerase activity in a PCR process increases the sensitivity of the PCR-based assay. We have identified, produced, purified, and analyzed novel extracts, proteins, and complexes that improve the polymerization activity of nucleic acid polymerases. Included within the aspects of the present invention are methods for identifying compositions with a polymerase enhancing activity, methods for purifying and using these compositions, and specific extracts, proteins, and complexes that function to enhance polymerase activity.

3. Description of Related Art

Manipulating nucleic acids with polymerization reactions is a fundamental component of biotechnology-related research. These reactions permit researchers to replicate DNA or RNA in vitro, which in turn allows cloning or amplification of specific nucleic acids or groups of nucleic acids. Numerous other examples exist detailing the critical nature of a nucleic acid polymerization reaction or a nucleic acid polymerization enzyme in a particular technique, including sequencing nucleic acids, mutagenesis of nucleic acid sequences, and producing nucleic acid probes for hybridization. Of particular current interest are amplification reactions, such as PCR, that have greatly increased the rate at which researchers can perform nucleic acid related experimentation. Extremely rare nucleic acids can now be amplified and manipulated using these techniques, which necessarily involve nucleic acid polymerases.

Using techniques with an amplification step has driven concern for the efficiency, fidelity, and sensitivity of the polymerase used. This has resulted in efforts to both analyze and optimize polymerization conditions for a variety of applications. (Lundberg et al., Gene 108: 1-6 (1991); Eckert and Kunkel, PCR Methods Applic. 1: 17-24 (1991); Ling et al., PCR Methods Applic. 1: 63-69 (1991); Brail et al., Mutat. Res. 303: 75-82 (1994); Garrity and Wold, P.N.A.S. 89: 1021-1025 (1992); Taylor and Logan, Curr. Opin. Biotechnol. 6: 24-29 (1995)) In particular, quantitative amplification-based reactions rely upon the ability to efficiently amplify each nucleic acid species present in a sample. (See Ausubel, et al., Chapter 15, In: Current Protocols in Molecular Biology, John Wiley & Sons (1992) and supplements through 1995.) Thus, both a concern for the accuracy of and a need for new methods to enhance the performance of amplification-based nucleic acid techniques exists in the art.

One way in which these concerns and needs have been addressed is through the use of additives to the amplification reaction. Different additives act at different points in the amplification process. For example, formamide has been used to increase the specificity of PCR with GC rich target sequences, which are particularly susceptible to intramolecular hybridization that may prevent hybridization with a primer. (Sarkar, G. et al. Nucl. Acids Res. 18: 7465 (1990)). It has also been reported that tetramethylammonium chloride increases yield and specificity of PCR reactions. (Chevet, E., et. al., Nucleic Acids Res. 23:3343-3334 (1995).) Hung et al. report the reduction in multiple satellite bands from amplifying complex DNA when dimethyl sulfoxide (DMSO) is added. (Hung, T., et al. Nucl. Acids Res. 18: 4953(1990).) The multiple satellite bands often present problems in purifying the desired amplification product from the other DNA present.

Certain proteins have been used to stabilize hybridized nucleic acids during replication. For example, E. coli single-stranded DNA binding protein has been used to increase the yield and specificity of primer extension reactions and PCR reactions. (U.S. Pat. Nos. 5,449,603 and 5,534,407.) The gene 32 protein (single stranded DNA binding protein) of phage T4 apparently improves the ability to amplify larger DNA fragments (Schwartz, et al., Nucl. Acids Res. 18: 1079 (1990)) and enhances DNA polymerase fidelity (Huang, DNA Cell. Biol. 15: 589-594 (1996)). In addition, bacterial thioredoxin combined with T7 DNA polymerase (Sequenase™; Amersham-USB) has been used to increase processivity, but the combination is not active at high temperatures, such as those used in PCR.

Another way amplification-based assays and techniques have been improved is through the development of modified polymerases or the use of combinations of polymerases. (U.S. Pat. No. 5,566,772) For example, the TaKaRa long PCR kit employs two polymerases (Takara Shuzo Co., Ltd; Japan), and a number of polymerase combinations were also tested by Barnes (Proc. Nat. Acad. Sci. USA, 91:2216-2220 (1994). Truncated Taq and T. flavus DNA polymerase enzymes that apparently exhibit increased thermostability and fidelity in PCR have also been suggested. (U.S. Pat. No. 5,436,149.) Combinations of polymerases with and without 5'→3' exonuclease or 3'→5' proofreading activity have also been used. (U.S. Pat. No. 5,489,523)

Further, amplification-based assays and techniques have been improved through empirical testing of conditions, reagents, and reagent concentrations to optimize polymerization reactions with a particular enzyme. Temperature and length of amplification cycles, primer length, and pH, for example, are all conditions that can be optimized. (Barnes, Proc. Nat. Acad. Sci. USA, 91:2216-2220 (1994).)

However, accessory proteins can be even more useful in improving polymerase activity and/or the processivity of polymerases. "Processivity" in this context refers to the number of enzymatic reactions occurring each time an enzyme binds to its substrate. In the context of nucleic acid replication reactions, "processivity" means the number of bases that can be replicated when the polymerase binds to a priming site. An increase in processivity directly relates to longer replication products.

Intracellular replication has been shown to involve accessory proteins, as characterized in E. coli, human, and phage T4 systems. The accessory proteins interact with polymerases to improve activity and provide the high processivity necessary to replicate genomic DNA efficiently while avoiding unacceptable mutation rates. Since the accessory proteins can be used in combination with the other improvements noted above, the development and application of accessory proteins holds particular promise for enhancing the results of nucleic acid replication-based reactions.

Accessory proteins have been identified in eukaryotes, *E. coli,* and bacteriophage-T4 and are thought to form "sliding clamp" structures. (Kelman and O'Donnell, Nucl. Acids. Res. 23(18): 3613-3620 (1995).) These structures are thought to tether the polymerase to DNA, thereby increasing processivity. The sliding clamp structures, however, have largely been studied in in vitro model systems. Only in the case of T4 polymerase has knowledge of the activity of such accessory proteins been used to improve polymerization-based techniques employed by researchers in the art. For example, accessory proteins of the T4 holoenzyme have been reported to improve processivity when added to polymerization systems using T4 polymerase. (Young et al., Biochem. 31(37): 8675-8690 (1992); Oncor Fidelity™ Sequencing System, Oncor; Gaithersburg, Md.) However, since the T4 accessory proteins are derived from bacteriophage, they are not likely to enhance polymerases from bacteria, archae, or eukaryotes. Thus, the use of T4 accessory proteins is believed to have been limited to techniques where T4 polymerase is used.

The presence of dUTP (deoxyuracil triphosphate) in a polymerization reaction and the effect of deoxyuridine-containing DNA or DNA synthesis have also been examined. In particular, deoxyuridine in a DNA strand has been shown to inhibit polymerization by archael DNA polymerases. (Lasken, et al., (1996) *J. Biol. Chem.* 271; 17692-17696.) While Lasken et al. reported that archeal DNA polymerases, such as Vent, are inhibited by DNA containing deoxyuridine, they do not discuss the effect of removing uracil-containing nucleosides or nucleoside triphosphates from the reaction to prevent incorporation. Furthermore, they do not discuss any enzyme that acts on or turns over dUTP in a reaction. Neither do they mention any dUTPase activity or the possible effect of dUTPase activity on polymerization reactions. In addition, Lasken et al. do not appreciate the fact that dUTP is generated during the course of a normal PCR reaction by the deamination of dCTP. As a result of the deamination, dUTP will be present and be incorporated into an amplified nucleic acid, inhibiting the polymerase activity. Thus, the art has not appreciated the potential of dUTPase activities and proteins in enhancing replication reactions.

Accordingly, since present knowledge and use of accessory proteins has led to limited applications in replication-based techniques, there continues to exist a need in the art for new and more widely useful compositions for enhancing polymerase enzyme activity. The present invention meets this need.

SUMMARY OF THE INVENTION

The present invention comprises extracts, protein complexes, and related proteins that possess nucleic acid polymerase enhancing activity useful in a variety of replication reactions known in the art. Thus, the extracts, protein complexes, and related proteins of the invention function to enhance a wide spectrum of in vitro nucleic acid replication reactions by providing, inter alia, replication products of superior length, fidelity or both, and at higher yields. As used in this specification and appended claims "polymerase enhancing activity" means the ability to increase the rate, fidelity, and/or yield of a nucleic acid polymerization reaction mediated by a nucleic acid polymerase, or to expand or alter the range of conditions under which such reaction does or may proceed.

In one aspect of the invention, extracts of *Pyrococcus furiosus* (Pfu) cells are provided that enhance the activity of Pfu DNA polymerase. The extracts enhance nucleic acid replication product yields over a fairly broad range of concentrations and contain at least one polymerase enhancing factor. As used in this specification and in the appended claims, the term "PEF" includes purified naturally occurring polymerase enhancing factors and wholly or partially synthetic copies or active analogs thereof. In accordance with the invention, such extracts can be further purified by heparin affinity chromatography followed by sepharose gel purification. Additionally, PEFs can be identified and purified using the antibodies of this invention, discussed below. While Pfu cell samples were used and are specifically exemplified below, one skilled in the art will appreciate that other cell samples can be used to identify and purify PEFs. For example, other species of the archae *Pyrococcus* or *Thermococcus* can be used as well as thermophilic bacteria cells and other bacteria cells. In addition, eukaryotic cells and tissues can be used as a source for PEF, as demonstrated by the cloning and expression of human dUTPase, which also enhances polymerase activity. Thus, the invention also comprises compositions and methods wherein a dUTPase or any activity that turns-over dUTP is capable of acting to enhance a nucleic acid polymerization reaction.

In another aspect of the invention, PEF complexes are provided. The PEF complexes of the invention possess polymerase enhancing activity and generally comprise multiple protein subunits with a combined molecular weight of approximately 250 kD or above as determined by SDS-PAGE analysis and gel filtration of unheated PEF samples. An example of one PEF complex (P300) was purified from Pfu cell sample extracts. The predominant components of the complex are a 50 kD protein (P50) and a 45 kD protein (P45). Heat treating the Pfu P45 with 2% SDS and 1% TCA produces a 17-18 kD protein, which represents the fully denatured form. However, the Pfu PEF complex contains other minor components with approximate apparent molecular weights of 150, 100, 85, 60, 55, 42, and 37 kD. At least two components (150 and 100) have been shown to be dimeric or polymeric forms of P50. Thus, the PEF complexes of the invention comprise protein components and function to enhance the activity of polymerases.

In another aspect of the invention, Pfu proteins possessing polymerase enhancing activity are provided. These proteins have molecular weights between approximately 42 and 60 kD by SDS PAGE analysis under partially denaturing conditions. The 42-60 kD proteins may be used alone or in combination to enhance polymerase activity. Methods for purifying these proteins as well as the PEF extracts and PEF complexes from which they have been isolated are also provided.

The invention also involves two particular proteins, Pfu P50 and P45, which are predominant components of the PEF complex (P300). Detailed structural and functional information on the Pfu P45 and P50 proteins is disclosed. The P50 protein is similar in structure to a bacterial flavoprotein. The P45 protein is similar in structure to dCTP deaminase, functions as a dUTPase, and possesses polymerase enhancing activity. The structural information herein can be used to generate specific hybridization probes that detect the presence of nucleic acids encoding a protein that is part of a PEF complex, or related proteins from samples from other species, or possesses PEF activity. Furthermore, the structural information can be used to generate proteins from expression systems known in the art, synthetic proteins, partially synthetic proteins, or proteins made from a combination of natural proteins, expressed proteins, and synthetic proteins. Methods for detecting the presence or absence of polymerase enhancing activity and/or dUTPase activity are also included in this invention and can be used to identify the various active PEF proteins or analogs. In addition, polyclonal or monoclonal antibodies that bind to PEF components can be produced, for example from purified P45 or P50, purified PEF complexes (P300), or another PEF of the invention. These antibodies can then be employed in assays and kits, well known in the art, in order to identify the presence or absence of a PEF.

The understanding of the catalytic activity of PEF, and the P45 protein in particular, provides aspects of this invention directed to polymerase enhancing proteins, as well as methods, kits, and compositions containing a dUTPase activity or dUTPase protein as a PEF. Thus, a dUTPase activity or dUTPase protein or composition can be used to enhance nucleic acid replication, polymerization, or PCR reactions according to this invention. In fact, any activity that functions to turnover dUTP can be used as a polymerase enhancing activity of this invention. Wide-ranging sources for the dUTPase activity, protein, or composition exist, as it is demonstrated to be present from both archael and human sources, the ends of the phylogenetic possibilities. Thus, any cell or species can be used as a source for polymerase enhancing activity or PEF.

Kits for replicating nucleic acids and methods for using the PEF complexes, specific proteins of the complexes, and extracts containing PEF are also provided. In addition, the complexes, proteins, and extracts can be used in compositions comprising a polymerase. Ideally, the polymerase will be one that is enhanced by the complex, protein, or PEF. The PEF extracts, complexes and proteins of the present invention are particularly useful in mixtures with nucleic acid polymerases, such as native polymerases, those produced by recombinant DNA techniques, and kits containing such polymerases.

Also provided in the invention are methods for identifying proteins or complexes that influence nucleic acid polymerases. The source of the protein can be any bacterial, archael, or eukaryotic species. Certain embodiments involve methods for identifying proteins affecting polymerases used in amplification reactions, for example, alpha-type DNA polymerases such as DNA polymerases derived from *Pyrococcus* and *Thermophilis* species. Other embodiments involve the analysis of dUTPase activity as well as computer implemented screening methods to identify a PEF.

DESCRIPTION OF THE DRAWINGS

FIG. 1: lane 1, buffer; lanes 2, 4 column fraction diluted 1:10; lanes 3, 5 column fraction diluted 1:100. In FIG. 1, lanes 4 and 5, λAA742 DNA has been omitted from the reactions.

FIG. 2: lane 1, buffer; lanes 2, 5 column fraction undiluted; lanes 3, 6 column fraction diluted 1:10; lanes 4, 7 column fraction diluted 1:100. In FIG. 2, lanes 5-7, cloned Pfu DNA polymerase has been omitted from the PCRs.

FIG. 3 shows the PCR enhancing activity of proteins eluted from SDS-PAGE gel slices 1-7 (native Pfu DNA pol.; lanes 1-7) and 9-20 (H.S. #78; lanes 9-20 from FIG. 4). The proteins were eluted as described in Example 2. One (1) µl of each gel slice, diluted 1:100 in cloned Pfu PCR buffer, was added to cloned Pfu PCRs as described in Example 1 (6.2 kb primer-template system). In the left lanes of the gel is shown PCR product synthesis in the presence of 1 µl of buffer (−) or H.S. #78, diluted 1:1000 (0.001 µl), 1:10,000 (0.0001 µl), or 1:100,000 (0.00001 µl). DNA markers were electrophoresed in lane "m".

FIG. 4 shows a duplicate of the master SDS-PAGE gel from which gel slices were excised. The following proteins were electrophoresed on both gels: lane A, 8 µl of native Pfu DNA polymerase (lot #24); lane B, pre-stained molecular weight markers (Novex); lane C, heparin sepharose fraction SCS #36 H.S. #78 4 µl (≈160 ng PEF). The samples were not pre-heated before loading, and the duplicate gel shown here was silver-stained. Gel slices 1-7 were recovered from lane A on the master gel, while slices 8-25 were recovered from lane C of the master gel.

FIG. 28. A 1.9 kb lac-Il-lacZα target was amplified from plasmid DNA. 100 µl PCRs were conducted with 50 pg of pPRIAZ, 100 ng of primers (5'CAT AGC GAA TTC GCA AAA CCT TTC GCG GTA TGG 3' (SEQ. ID NO: 20); 5'ACT ACG GAA TTC CAC GGA AAA TGC CGC TCA 3' (SEQ ID NO: 21)), and 5U cloned Pfu DNA polymerase in the absence (duplicate samples #18) or the presence (duplicate lanes #19) of 0.5 µl of a PEF-containing heparin sepharose fraction (H.S. #75; prep. 4; ≈10 ng/µl PEF). PCR cycling was conducted on a GeneAmp PCR System 9600 (Perkin Elmer Cetus) using the following conditions: 30 s at 95° C. (1 cycle)/5 s at 95° C.; 1 min. at 55° C.; 2.5 min. at 72° C. (30 cycles). FIG. 29. A 10 kb target from lambda DNA was amplified. 100 µl PCRs were conducted with 250 ng of lambda DNA (Sigma), 250 ng of primers (F51-20 5'GGC-GTT-TCC-GTT-CTT-CTT-CG 3' (SEQ ID NO: 22) R10163-20 5'CCA-TCT-CAC-GCG-CCA-GTT-TC 3' (SEQ ID NO: 23)), and 5U cloned Pfu DNA polymerase in the absence (lane 1) or the presence of 1 µl of a S200-purified PEF (prep. 3; 550 ng/µl PEF) diluted 1:500 (lane 2), 1:50 (lane 3), or 1:5 (lane 4). PCR cycling was conducted on a Robocycler 40 (Stratagene) usingthe following conditions: 95° C. for 1 min. (1 cycle)/95° C. for 1 min.; 62° C. for 1 min.; 72° C. for 10 min. (30 cycles). FIG. 30. Lanes 1-5, a 5.2 kb portion of the human α1 antitrypsin gene was amplified from genomic DNA. 25 µl PCRs were conducted with 62.5 ng of human genomic DNA (Promega), 50 ng of primers (F91-23 5'GAG GAG AGC AGG AAA GGT GGA AC (SEQ ID NO: 24); R5271-21 5'GCT GGG AGA AGA CTT CAC TGG) (SEQ ID NO: 25), and 0.6U cloned Pfu DNA polymerase in the absence (lane 1) or the presence of 1 µl of S200 purified PEF (SCS #52; 0.7 ug/ul) diluted 1:1000 (lane 2), 1:10,000 (lane 3), 1:100,000 (lane 4) or 1:1,000,000 (lane 5). PCR cycling was conducted on a RoboCycler 96 (Stratagene) using the following conditions: 96° C. for 45 s (1 cycle)/96° C. for 45 s; 60° C. for 45 s; 72° C. for 14 min. (35 cycles)/72° C. for 10 min. (1 cycle).

In FIG. 33, 25 µl PCRs were conducted using the 6.2 kb test system (example 1) with 25U/ml Pwo DNA polymerase and 1× cloned Pfu PCR buffer. 1 µl of S200-purified *P. furiosus* PEF (prep. 1; 225 ng/µl) was added undiluted (lane 1) or diluted 1:10 (lane 2), 1:1000 (lane 3), 1:10,000 (lane 4). 1 µl of dilution buffer was added as a negative control (lane 5). In FIG. 34, a 10 kb lambda DNA target was amplified from lambda DNA (lanes 1-4; 5-7; 11-13) or mouse genomic DNA, containing 40 copies (lanes 8-10) or 1 copy (lanes 14-16) of a lambda DNA transgene. 100 µl PCRs were conducted with 250 ng of lambda DNA (Sigma) or mouse genomic DNA, and 250 ng of primers (F51-20 5'GGC-GTT-TCC-GTT-CTT-CTT-CG (SEQ ID NO: 22); R10163-20 5'CCA-TCT-CAC-GCG-CCA-GTT-TC) (SEQ ID NO: 23). PCRs were conducted in Taq PCR buffer using 5U Taq DNA polymerase (lanes 1-4) or 1U JDF3

DNA polymerase (lanes 5-16). 1 µl of the following was added to PCRs: S200-purified PEF (prep. 3; 550 ng/µl PEF) diluted 1:500 (lanes 2, 12, 15), 1:100 (lanes 6, 9), 1:50 (lane 3), 1:10 (lanes 7, 10, 13, 16) or 1:5 (lane 4). 1 µl of dilution buffer was added as a negative control (lanes 1, 5, 8, 11, 14). PCR cycling was conducted on a Robocycler40 (Stratagene) using the following conditions: 95° C. for 1 min. (1 cycle)/95° C. for 1 min.; 62° C. for 1 min.; 72° C. for 10 min. for Taq or 5 min. for JDF3 (30 cycles). In FIG. 35, the 1.9 kb ligase gene was amplified from P. furiosus genomic DNA. 100 µl PCRs were conducted with 250 ng of DNA and 250 ng of primers (5'GAG CTT GCT CAA CTT TATC (SEQ ID NO: 26); 5'GAT AGA GAT AGT TTC TGG AGA CT) (SEQ ID NO: 27). PCRs were conducted with 10U ES4 DNA polymerase in Pfu PCR buffer (lanes 1, 2), 1.5U JDF3 DNA polymerase in Taq PCR buffer (lanes 3, 4), 4U Pfu DNA polymerase in cloned Pfu PCR buffer (lanes 5, 6), 1U Vent DNA polymerase in Vent PCR buffer (lanes 7, 8), or 1U Taq DNA polymerase in Taq PCR buffer (lanes 9, 10). 1 µl of the following was added to PCRs: dilution buffer (lanes 1, 3, 5, 7, 9) or S200-purified PEF (prep. 3; 550 ng/µl PEF) diluted 1:100 (lanes 2, 4, 6, 8, 10). PCR cycling was conducted on a DNA Thermal Cycler 480 (Perkin Elmer Cetus) using the following conditions: 95° C. for 1 min.; 46° C. for 1 min.; 72° C. for 2 min. (30 cycles). In FIG. 36, a 2 kb DNA target was amplified from transgenic mouse genomic DNA. 100 µl PCRs were conducted with 250 ng of DNA and 250 ng of primers (F51-20 5'GGC GTT TCC GTT CTT CTT CG (SEQ ID NO: 22); R2092-23 5'CGG GAT ATC GAC ATT TCT GCA CC) (SEQ ID NO: 28). PCRs were conducted with 0.75U Deep Vent DNA polymerase in Deep Vent PCR buffer (lanes 1-4). 1 µl of the following was added: dilution buffer (lane 1) or S200-purified PEF (prep. 3; 550 ng/µl PEF), diluted 1:500 (lane 2), 1:100 (lane 3), 1:50 (lane 4). PCR cycling was conducted on a Robocycler40 (Stratagene) using the following conditions: 95° C. for 1 min. (1 cycle)/95° C. for 1 min.; 62° C. for 1 min.; 72° C. for 2 min. (30 cycles).

FIG. 39. Enhancement of Pfu DNA polymerase-based QuikChange mutagenesis with P. furiosus PEF. QuikChange mutagenesis was performed using the kit control primers and plasmid template, with either native or cloned Pfu DNA polymerase. To the reactions was added 1 µl of dilution buffer or 1 µl of a PEF-containing heparin sepharose fraction (SCS #36 H.S. #78; prep. 2 ≈40 ng/µl), diluted as indicated. The relative amount of linear amplification product was assessed by the intensity of ethidium bromide-stained product bands on agarose gels. Supercompetent E. coli cells were transformed with the digested amplification products. The number of amp resistant colonies and the mutation frequencies were scored.

In FIG. 40, purified PEF (225 ng/µl; prep. 1) was diluted in 1× cloned Pfu PCR buffer and 1 µl aliquots of the following were added to 24 µl PCRs—lane 1, buffer; lane 2, PEF undiluted; lanes 3-6, PEF diluted 1:10, 1:100, 1:1000, 1:10,000, respectively. In FIG. 41, the following amounts of purified PEF were added: lane 1—1 µl of buffer, lane 2—1 µl PEF neat, lanes 3-8, 1 µl PEF diluted 1:10, 1:100, 1:1000, 1:10,000, 1:100,000 and 1:1,000,000.

In FIG. 42, 1 µl aliquots of the following were added to 50 µl PCRs—lane 1, buffer; lanes 2-5, PEF diluted 1:10, 1:100, 1:1000, 1:10,000, respectively. In FIG. 43, 1 µl aliquots of the following were added to 24 µl PCRs—lane 1, buffer; lane 2, PEF undiluted; lanes 3-6, PEF diluted 1:10, 1:100, 1:1000, 1:10,000, respectively. DNA markers were electrophoresed in lane "m".

DETAILED DESCRIPTION OF SPECIFIC EMBODIMENTS OF THE INVENTION

Figure 1:
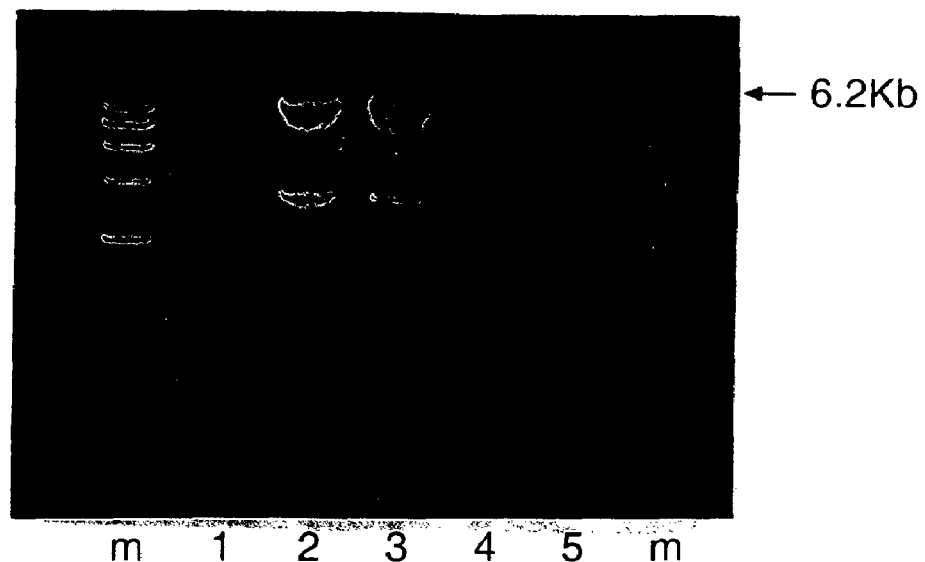
FIG. 1. PCR enhancing activity in a heparin sepharose column fraction. PCR enhancing activity was measured using the 6.2 kb system described in example 1. Column fraction SCS #36 H.S. #78 (prep. 2) was diluted in 1× cloned Pfu PCR buffer and 1 µl aliquots of the following were added to 100 µl PCRs.

The following description should not be construed to limit the scope of this invention to any specifically described embodiment. Various aspects and embodiments of this invention will be apparent from the disclosure as a whole in context with the knowledge of one skilled in the art. In addition, the description herein, in combination with information known or available to persons of ordinary skill in the art, enables the practice of the subject matter encompassed by the following claims.

For the purposes of this invention, a nucleic acid replication reaction can mean any of the numerous nucleic acid amplification, primer extension, reverse transcription, or other nucleic acid polymerization reactions known in the art. Additionally, a replication reaction of this invention includes any reaction in which the ability of an enzyme to interact with a first nucleic acid and generate a second, substantially complementary nucleic acid sequence, is involved. The amplification reactions of this invention are not limited to PCR processes or any particular PCR-based assay, although they are particularly useful herein, and specifically include RT-PCR processes. The proteins, preparations, compositions, mixtures, kits and methods of this invention can be used with any appropriately designed nucleic acid replication reaction.

As used herein, the term "PEF" refers to a naturally occurring protein derived from a bacterial, eukaryotic, or archael source (or a wholly or partially synthetic copy or analog thereof) having polymerase enhancing activity, mixtures of one or more such proteins, protein complexes containing one or more such proteins, or extracts containing one or more of such proteins, mixtures or complexes. Recombinant PEF proteins, as a wholly synthetic copy of a naturally occurring protein, and complexes with at least one recombinant PEF protein are also "PEFs" according to this invention. The Pfu P45 and P50 proteins of this invention are illustrative of PEF proteins, which exhibit an apparent molecular weight of approximately 45 kD and 50 kD and are predominant components of a PEF complex derivable from Pfu. Data relating to both the P45 and P50 proteins is presented herein and details specific structural information. On SDS-PAGE, the non-heat-treated PEF complex containing P45 and P50 as well as minor additional components migrates with an apparent molecular weight >250 kD. One species of the PEF complexes of this invention is the P300 complex from *Pyrococcus furiosus*.

The present invention is intended, however, to encompass other PEF proteins, mixtures, complexes, compositions, and extracts derived from organisms other than Pfu identified by techniques analogous to those provided by the following examples, or by use of the structural information on the PEF proteins described herein or derivable from the proteins described herein. More specifically, the invention is intended to encompass PEFs identified on the basis of sequence homology to all or part of the PEFs described herein, including nucleic acid homology to all or part of the DNA sequence encoding the proteins described herein or the DNA sequences described herein. Computer-implemented homology searches using the sequence information herein, stored on an appropriate computer-readable medium, with procedures known in the art, can generate these homologous PEFs. Also, reactivity with antibodies to the proteins, complexes, or extracts disclosed herein can be used with procedures known in the art to generate homologous PEFs.

One skilled in the art is familiar with methods of generating analogs of proteins. Various techniques from publications in the art can be used to mutate, modify, truncate, or otherwise change a protein's amino acid sequence and retain functional activity. In the case of a dUTPase activity as PEF, the known crystal structure of dUTPases, such as *E. coli* dUTPase, provides specific information on regions of a dUTPase that may be mutated in any of a number of ways while still retaining PEF activity (see Cedergren-Zeppezauer, E. S., et al., Nature 355: 740 (1992), which also notes similarities to mammalian dUTPases in Hokari, S., et al., Arch. Biochem. Biophys. 253: 350 (1987)). Similarly, wholly or partially synthetic or recombinantly expressed proteins can also be generated from the information herein by those skilled in the art. (For example, Ausubel et al. (1989) Current Protocols in Molecular Biology, and supplements through February 1997.)

Furthermore, a PEF can also be a protein exhibiting a dUTPase activity, as demonstrated herein. Specifically, human, *Pyrococcus furiosus,* and *Thermus thermophilis* dUTPase activities can be used to enhance polymerization reactions as a PEF. Other eukaryotic, bacterial, and archael sources can similarly be used to derive a PEF as a dUTPase protein. A PEF can also be any protein that functions to turn-over dUTP or lower the concentration of dUTP. Similarly, the invention comprises a method of enhancing replication or amplification reactions by reducing the dUTP concentration or preventing the incorporation of dUTP into replicated or amplified products, as well as compositions that are capable of preventing that incorporation.

The polymerase enhancing activity of the PEFs of this invention can be determined in a number of different ways. The description below details a few examples of assays and techniques one skilled in the art can use to determine if PEF activity is present. These assays and techniques can be used alone or in combination.

Example 1 specifically details screening assays and the "on/off" assay. This type of PCR assay allows one to identify the presence of a polymerase enhancing activity in a sample. More generally, any assay that shows an increase in PCR product yield, over a negative control level, when a sample suspected to contain a polymerase enhancing activity is added can be used to identify a polymerase enhancing activity. Also, any assay that shows an increase in processivity, over a control level, reflected by the increased length of PCR products being generated when a sample suspected to contain a polymerase enhancing activity is used. A combination of PCR product yield and increased processivity can also be used to determine whether or not a polymerase enhancing activity is present.

A polymerase enhancing activity can also be identified by assays that indicate a reduction in the PCR inhibitory action of incorporated dUTP. For example, PCR reactions can be conducted in the presence of dUTP and samples suspected of containing polymerase enhancing activity. Those reactions that allow polymerization in the presence of dUTP indicate a polymerase enhancing activity in the form of a dUTPase activity. Thus, a dUTPase activity can be a polymerase enhancing activity.

Also, a composition that functions to turn-over dUTP, especially under thermophilic reaction or PCR reaction conditions, can be a polymerase enhancing activity as a dUTPase. An enzyme or activity that acts on dUTP so that it is not incorporated into a newly polymerized strand functions to turn-over dUTP. The turn-over of dUTP can also be detected by an assay for the conversion of dUTP into dUMP, as detected by analyzing the reaction products by HPLC, for example. Biochemical assays that detect the conversion of dUTP into dUMP, or other nucleoside phosphate or metabolic derivatives or products, can be devised or are known in the art and can be used to identify polymerase enhancing activity as a dUTPase activity.

A polymerase enhancing activity can also be a dUTPase enzyme that possesses the consensus uridine-binding sequence motif (SEQ ID NO.: 72). A number of those enzymes are identified below. However, numerous others exist or can be identified through computer-implemented or other sequence analysis procedures known in the art. Thus, the presence of the consensus uridine-binding motif or the related sequences shown herein can also be used to define an enzyme or protein that is a PEF, such as a protein that comprises SEQ ID NO.: 72, or any one of SEQ ID NOs.: 72-81, or combinations of these sequences.

Also, proteins identified through sequence identity comparisons known in the art can be used to confirm the presence of a PEF. For example, proteins from one species possessing a sequence identity of approximately 18% or greater have been shown in the art to be related to or analogous to the known protein of another species. In the examples below, a sequence similarity of approximately 39% suffices to positively identify a dUTPase activity that can act as a PEF.

The antibodies to PEF described herein can also identify a protein with polymerase enhancing activity. For example, Western blot analysis of compositions from various archeal, bacterial, thermophilic bacterial, or eukaryotic samples can identify a protein that possess polymerase enhancing activity. Furthermore, as the PEF proteins and complexes of this invention are demonstrated as immunogenic, various other antibodies to PEF may be produced by techniques known in the art with the information herein. These other antibodies can also be used to identify a PEF.

EXAMPLE 1

Screening for PEF Activity

Protein-containing extracts from a number of different sources can be tested for PEF activity. The extracts can be prepared in a number of ways known in the art.

One method was demonstrated with Pfu DSM 3638 cells. The cells were grown, a cell paste collected by centrifugation and then frozen at −80° C. The paste was taken up with lysis buffer [50 mM Tris-HCl (pH 8.2), 1 mM EDTA, 10 mM B-mercaptoethanol, 0.5 mM PMSF, and 2 µg/ml aprotinin], and thereafter the cells were lysed in a French press and then sonicated. Following sonication, the lysate was centrifuged and the supernatant, containing potential PEFs, was collected for assays.

Extracts from any cell producing a PEF, for example, cells transfected with a recombinant vector directing the expression of a PEF, can also be assayed. Methods of making extracts of these cells are known in the art and are exemplified below.

1. Screening Assays for PCR-Enhancing Activity

One method of detecting thermostable PEFs is by screening partially-purified fractions from thermophilic archeal or bacterial extracts for PCR enhancing activity. PCR enhancing activity can be detected in samples consisting of column-purified fractions as well as homogeneous protein samples and proteins recovered by elution from SDS-PAGE gel slices (see below). Samples are added to PCR amplification reactions containing DNA polymerase, buffer, dNTPs, primers, and DNA template. PCR enhancing activity is identified by an increase in PCR product yield for amplifications conducted in the presence of a particular sample (DNA polymerase+PEF) as compared to amplifications conducted in the absence of added sample (DNA polymerase only).

When screening samples suspected of containing endogenous DNA polymerase activity, for example protein extracts, negative controls can be performed in which the exogenous DNA polymerase has been omitted from the PCR amplifications. In addition, when screening samples contaminated with DNA, negative controls can be carried out in which exogenous DNA template is omitted from the PCR amplifications.

The sensitivity of the PCR enhancing assay is dependent on the complexity of the DNA targets employed. PCR reaction parameters (target complexity, DNA template concentration, polymerase concentration, PCR cycle number or extension time) can be adjusted so that the yield of PCR product is barely detectable under normal conditions. In addition, samples for testing can be diluted appropriately so that the concentration of PEFs falls within the detectable range of the PCR A second embodiment of an assay to screen for PEF employs, for example, the 5.2 kb human α1-antitrypsin gene in a PCR amplification. PCR amplification of this prime/template system was so limited that, in the absence of PEF, it was difficult to detect any PCR product. With added PEF activity, a 5.2 kb product was easily detected. The following conditions were used for this "On/Off" assay: In 100 µl—1× Cloned Pfu DNA polymerase buffer, 200 µM each dNTP, 200 ng primer F-91-23, 200 ng primer R5271-21, 125 ng Human Genomic DNA, 2.5 units cloned Pfu DNA polymerase, +/−PEF or recombinant P45 (rP45).

```
                                          (SEQ ID NO:64)
Primer F91-23    5' GAGGAGAGCAGGAAAGGTGGAAC 3'

(SEQ ID NO:65)
Primer 5271-21   5' GCTGGGAGAAGACTTCACTGG 3'
```

The PCR cycling conditions were as follows: 95° C. for 1 minute (1 cycle), 95° C. for 1 minute—60° C. for 1 minute—72° C. for 10 minutes (30 cycles). After completion, the reactions are run out on an electrophoresis gel and the quantity of reaction products determined by any of a number of methods known in the art.

3. Screening Assays for Nucleic Acid Replication Enhancing Activity

Extracts can also be added to any nucleic acid replication reaction to determine PEF activity. Many of these reactions are known in the art, including primer extension reactions, DNA sequencing reactions, site-directed mutagenesis reactions, and a number of PCR-based reactions. (Ausubel, F. M., et al. (1989) Current Protocols in Molecular Biology, Greene Publishing Associates and Wiley-Interscience, New York, N.Y.; Sambrook, J., et al. (1989) Molecular Cloning: A Laboratory Manual, 2nd Ed., Cold Spring Harbor Laboratory Press, Cold Spring Harbor, N.Y.) By comparing the results produced in a nucleic acid replication reaction with and without the added extract, one can identify the presence of PEF.

EXAMPLE 2

Purification of PEF from P. Furiosus

Once PCR enhancing activity has been detected from, for example, archeal or bacterial sources, large amounts of purified PEF can be obtained by column chromatography. The following protocol was developed for purifying PEF from P. furiosus (Pfu). However, one skilled in the art will appreciate that other cells or species could be used as well.

1. Cell Growth and Lysis

P. furiosus DSM 3638 cells were grown in a 400 liter fermentor according to established protocol. (U.S. Pat. No. 5,545,552, specifically incorporated herein by reference.) The cell paste was collected using a Sharples in-line centrifuge after approximately 20 hours (A600≈0.5), and then immediately frozen in liquid $N_2$ and stored at −80° C. until use. Then, 500 grams of frozen cell paste was transferred to a 4 liter stainless steel beaker on ice. The cells were resuspended with 2 liters of lysis buffer, consisting of 50 mM Tris-HCl (pH 8.2), 1 mM EDTA, 10 mM B-mercaptoethanol, 0.5 mM PMSF, and 2 µg/ml aprotinin. The cells were lysed in the French press using 2 passes at 8K PSI and the lysate was then sonicated for 10 minutes. Following sonication, the lysate was transferred to 400 ml bottles, spun for 1 hour at 9K rpm in a Sorvall RC-2B centrifuge using a Sorvall GS3 rotor, and the supernatant collected.

2. Purification by Column Chromatography

The supernatant was loaded at a flow rate of 5 ml/min. onto a 10×5 cm Q-Sepharose Fast Flow™ (Pharmacia) column (≈392 mls), pre-equilibrated in buffer consisting of 50 mM Tris-HCl (pH 8.2), 1 mM EDTA, and 10 mM B-mercaptoethanol. The column was washed with 2 column volumes of buffer, and the pass-through and column washes were collected and pooled. The pooled fractions were adjusted to pH 7.5 using 1N HCl.

The Q-Sepharose pass-through was then loaded at a flow rate of 5 ml/min. onto a 5×11.5 cm (≈225 mls) SP Sepharose Big Bead™ (Pharmacia) column, equilibrated in buffer containing 50 mM Tris-HCl (pH 7.5), 1 mM EDTA, 1 mM DTT, 10% (v/v) glycerol, 0.1% (v/v) Igepal CA-630, and 0.1% (v/v) Tween 20. The column was washed with equilibration buffer until the absorbance ($OD_{280}$) approached baseline. The column was eluted with a 2 liter gradient from 0 to 250 mM KCl (in equilibration buffer). Fractions of 20 ml were collected, and aliquots removed from every third tube for SDS-PAGE analysis.

Some of the fractions analyzed by SDS-PAGE showed a band >250 kD when a sample was not heated prior to electrophoresis (≈300 kD). The fractions containing the 300 kD band were pooled and dialyzed overnight against 2×4 liters of Buffer A [50 mM Tris-HCl (pH 8.2), 1 mM EDTA, 1 mM DTT, 10% (v/v) glycerol, 0.1% (v/v) Igepal CA-630, and 0.1% (v/v) Tween 20]. The dialyzed pool was loaded at a flow rate of 2 ml/min. onto a 2.6×29 cm (≈154 mls) Heparin Sepharose CL-6B™ (Pharmacia) column, equilibrated in Buffer A. The column was washed with 1 liter of Buffer A, and then eluted with a 1.5 liter gradient from 0 to 300 mM KCl/Buffer A. Fractions of 10 ml were collected, and aliquots removed from every third tube for SDS-PAGE analysis. Fractions containing the 300 kD band were pooled and dialyzed overnight against 2×4 liters of Buffer A.

The heparin sepharose-purified pool was loaded at a flow rate of 0.5 ml/min. onto a 1.6×95 cm (≈191 mls) Sephacryl S-200 High Resolution™ (Pharmacia) column equilibrated in Buffer A containing 100 mM KCl. Then, 2 ml fractions were collected and aliquots removed from every third tube for SDS-PAGE analysis. Fractions containing the 300 kD band were pooled and dialyzed overnight against 1 liter of buffer containing 50 mM Tris-HCl (pH 8.2), 0.1 mM EDTA, 1 mM DTT, 50% (v/v) glycerol, 0.1% (v/v) Igepal CA-630, and 0.1% (v/v) Tween 20. The purified protein was stored at −20° C. The purification protocol described above yielded ≈1 mg. of relatively homogeneous P300 band from 500 g. of cell paste.

3. Purification of PEF from SDS-PAGE Gels

PEF in a heterogeneous sample can be identified by eluting purified protein from SDS-PAGE gel slices and rescreening for PCR enhancing activity. This method allows rapid assessment of the number of PEF proteins in a particular sample and identification of their apparent molecular weight.

*P. furiosus* protein samples with PCR enhancing activity were electrophoresed on 4-20% acrylamide/2.6% bis-acrylamide Tris-Glycine gels (Novex), along-side pre-stained molecular weight markers. Samples were loaded in the presence of 2% SDS, but were not boiled in order to prevent dissociation of PEF complexes. The gels were run in Tris-Glycine buffer containing 1% SDS, and after electrophoresis, were washed briefly in 20 mM Tris-HCl (pH 8.0)/1 mM EDTA. Then, 2-3 mm gel slices were excised from the lanes of interest using the pre-stained molecular weight markers as a guide. Each gel slice was cut-up with a razor blade and the pieces transferred to 50 µl of elution buffer (20 mM Tris-HCl (pH 8.0)/1 mM EDTA/0.1% Tween-20). The slurry was incubated at 72° C. for 30 minutes.

Gel slices containing PEFs are identified by testing the eluates for PCR enhancing activity. Eluates containing >0.1 ng/µl PEF are then re-analyzed on silver-stained SDS-PAGE gels to verify the apparent molecular weight of the predominant protein component. The gel slice eluates are boiled in the presence of 2% SDS before loading and the apparent molecular weights of PEF proteins determined relative to protein standards. The gel slice elution procedure described here allows recovery of 1-10% of the protein of interest.

EXAMPLE 3

Figure 2:
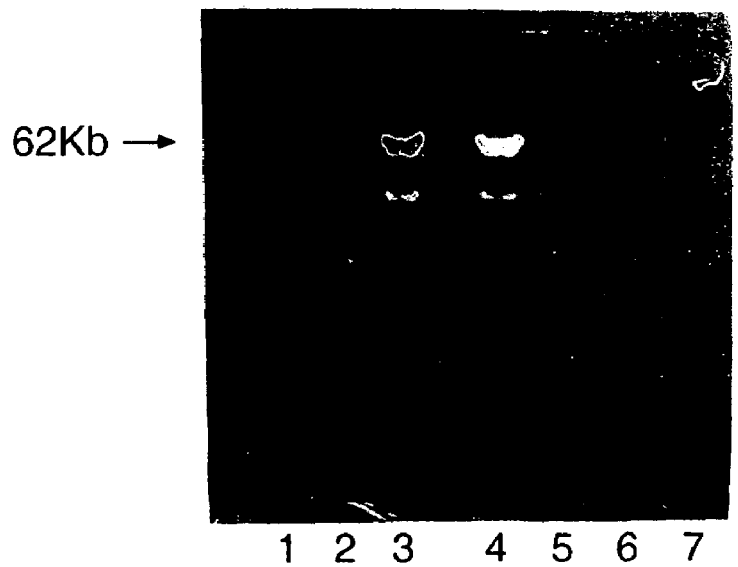
FIG. 2. PCR enhancing activity in a heparin sepharose column fraction.

Identification of the PCR Enhancing Activity in *P. Furiosus* Partially-Purified Column Fractions The fractions collected after the heparin sepharose chromatography were analyzed for PEF activity using the PCR screening assay (Example 1). The addition of diluted heparin sepharose fraction dramatically increased yields of PCR products generated with cloned Pfu DNA polymerase. The PCR enhancing activity of the fractions was shown to be dependent upon the presence of exogenous DNA template (FIG. 1) and Pfu DNA polymerase (FIG. 2). Increased PCR product yield was, therefore, not due to the presence of contaminating DNA template or native Pfu DNA polymerase, but rather to the presence of PEFs.

Figure 3:
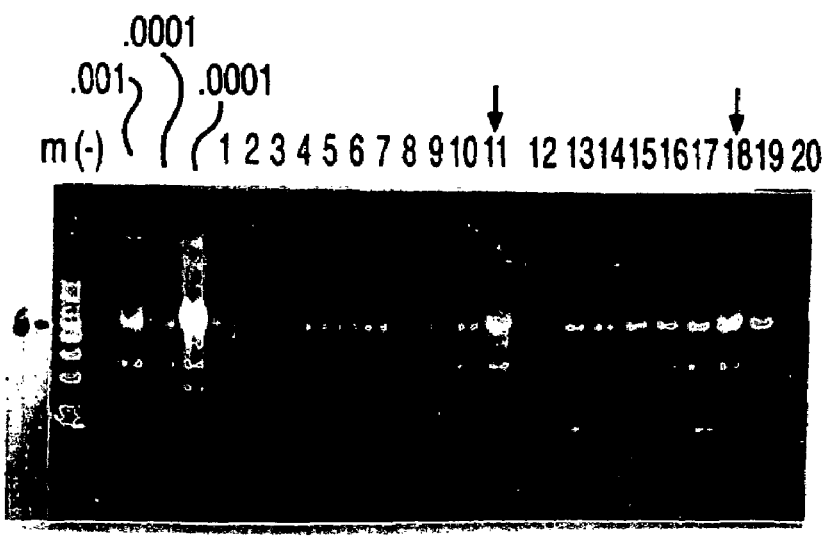
FIG. 3. PCR enhancing activity of SDS-PAGE gel-purified samples from heparin sepharose fraction SCS #36 H.S. #78 (prep. 2).
Figure 4:
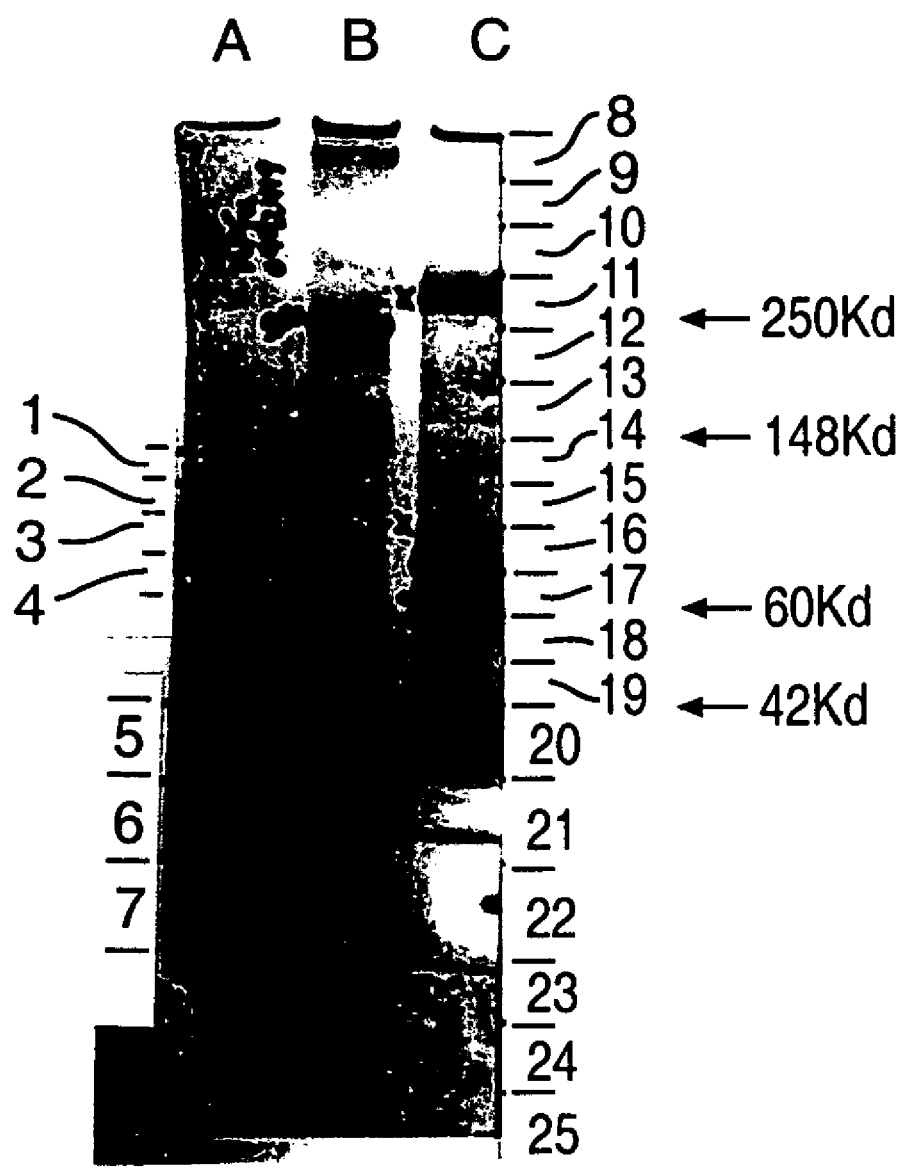
FIG. 4.

In order to further characterize the factor or factors responsible, the following was performed. PEFs after heparin sepharose chromatography were identified by screening SDS-PAGE gel-purified samples for PCR enhancing activity, as discussed above in Example 2. When the protein samples were loaded onto SDS-PAGE gels without pre-boiling, PCR enhancing activity (FIG. 3) was recovered in 2 gel slices from the gel of FIG. 4. One gel slice (gel slice #1) was excised from a position between the 42 and 60 kD markers, while the second gel slice (slice 190 2) was recovered from a site just above the 250 kD marker (FIG. 4).

Figure 5:
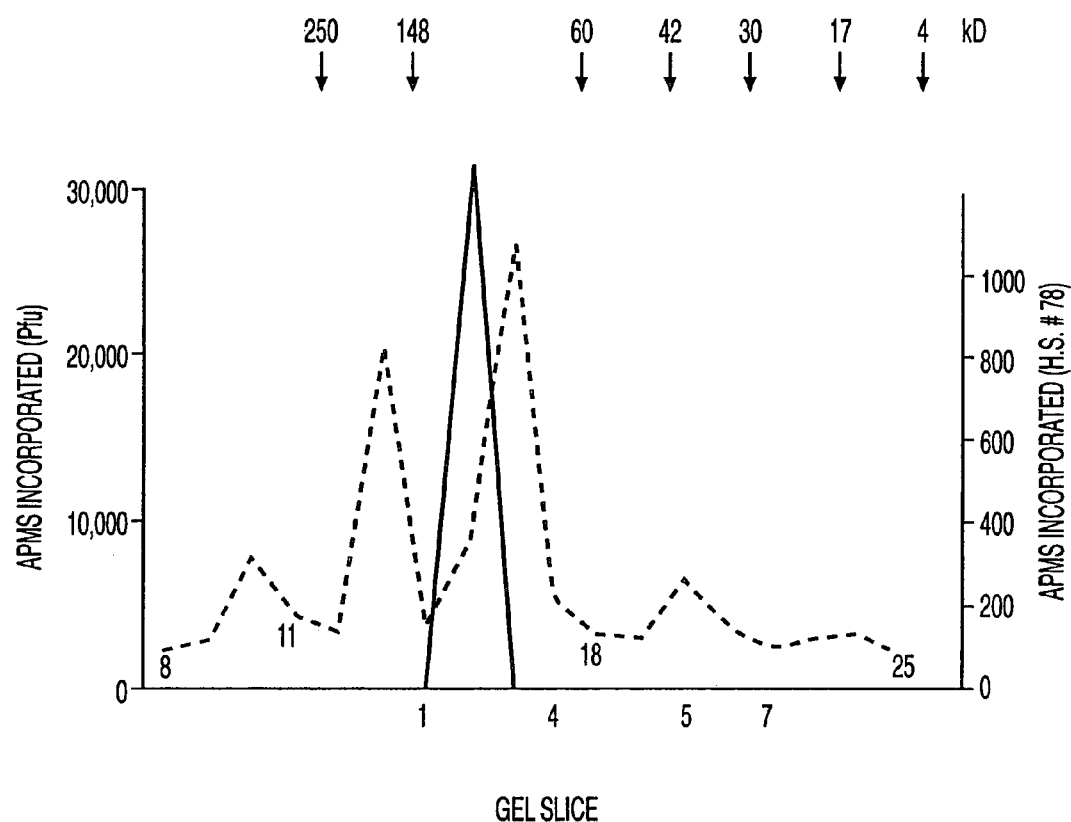
FIG. 5. DNA polymerase activity in SDS-PAGE gel purified samples. The level of DNA polymerase activity (cpms incorporated) in gel slice eluates (1 µl) was measured as described in Example 14. The polymerase activity exhibited by gel-purified proteins numbered 1-7 in the native Pfu DNA polymerase preparation (FIG. 4; lane A) is shown by the solid line (left Y axis). The polymerase activity of gel-purified proteins numbered 8-25 in fraction H.S. #78 (FIG. 4, lane C) is shown with the broken line (right-handed Y axis). The apparent molecular weights of the proteins tested are shown on the x axis (at the top) and are inferred from the position the gel slices were recovered, relative to pre-stained molecular weight markers. Gel slices #11 and 18 exhibited the highest PCR enhancing activity.

The proteins eluted from the gel slices were also screened for DNA polymerase activity to demonstrate that PCR enhancing activity was not related to contaminating DNA polymerase activity (FIG. 5). The results indicated that SDS-PAGE purified proteins with PCR enhancing activity lack significant DNA polymerase activity. Moreover, SDS-PAGE purified Pfu DNA polymerase lacks PCR enhancing activity when tested at protein concentrations comparable to or greater than those of gel-purified PEFs.

Figure 6:
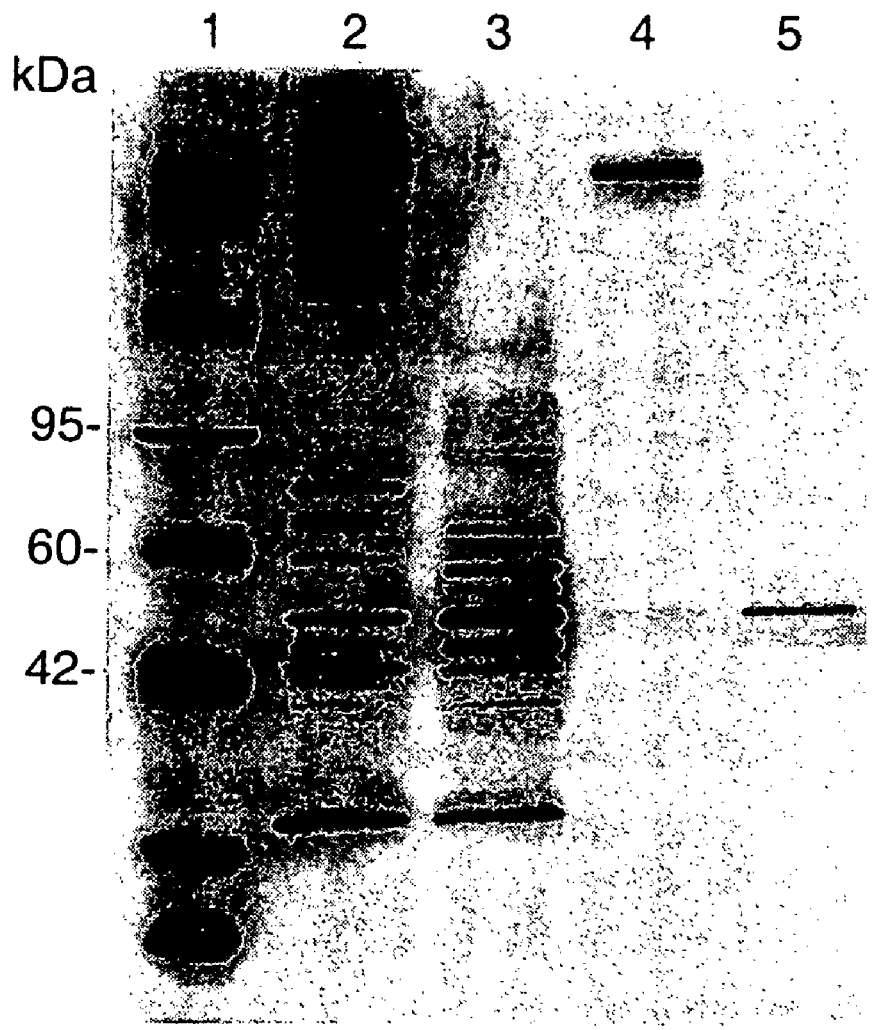
FIG. 6. SDS-PAGE analysis of gel-purified *P. furiosus* PEF. The following samples were electrophoresed on 4-20% acrylamide gels in the presence of 1% SDS: lanes 2, 3- SCS #37 H.S. fraction #75 (prep. 4; 10 µl of a Microcon 30 concentrated fraction; ≈100 ng PEF) lanes 4, 5 10 µl of SDS-PAGE gel slice eluate recovered from SCS #37 H.S. fraction #75 (migrated 0-4 mm above 250 kD protein marker). The samples in lanes 3 and 5 were boiled for 3 minutes before loading onto the SDS-PAGE gel. The completed gel was stained with silver stain. The migration of pre-stained molecular weight markers is shown in lane 1.

The *P. furiosus* PEF proteins were conclusively identified by re-analyzing gel purified samples with PCR enhancing activity on silver stained SDS-PAGE gels. In the absence of pre-boiling, the predominant band in gel slice #2 migrates somewhat slower than the 250 kD molecular weight marker, consistent with the site where the gel slice was recovered (FIG. 6). This band is called P300 or PEF complex. In addition, a minor band is evident at 50 kD, called P50. Gel slice #1 contained a major band at 50 kD and a minor band at 45 kD.

However, when the proteins eluted from gel slice #2 are boiled in SDS prior to loading, the predominant component migrates with an apparent molecular weight of 50 kD (FIG. 6). A minor or poorly staining component of ≈45 kD is also visible. These results are consistent with *P. furiosus* PEF consisting of two distinct proteins, with apparent molecular weights of 50 kD and 45 kD, which aggregate at low temperatures in presence of SDS to produce a complex which migrates as a discrete band at 300 kD.

EXAMPLE 4

Characterization of PEF Complex and Protein Components of the Complex

*P. furiosus* PEF fractions following S200 chromatography comprises a mixture of proteins. A discrete band in SDS-PAGE migrates above the 250 kD marker when the sample is not heated prior to electrophoresis. This protein is called P300 or PEF complex. When the conditions are changed to substantially dissociate the PEF complex, the subunit protein components of the PEF complex are visualized in SDS-PAGE.

1. Temperature-dependent Dissociation of dUTP Complex

Figure 7:
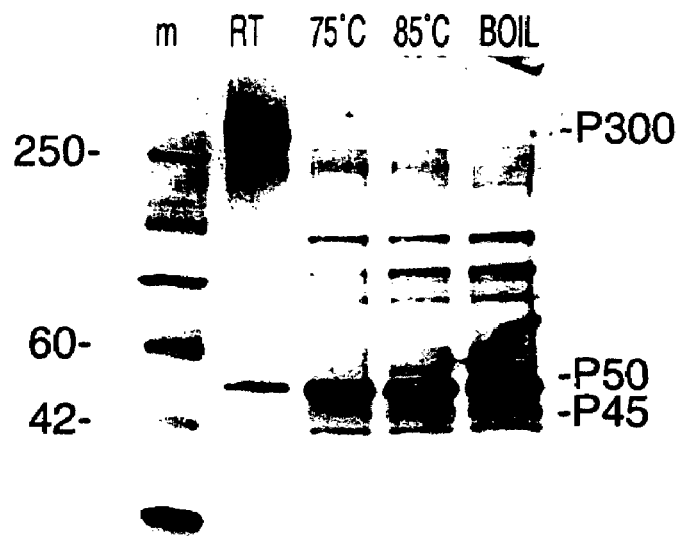
FIG. 7. SDS-PAGE analysis of S200-purified *P. furiosus* PEF. 10 µl (2.25 µg) of S200-purified PEF (prep. 1) was incubated in the presence of 2% SDS for 3 minutes at room temperature (RT), 75° C., 85° C., or 100° C. (boil), as indicated on the lanes, and then subject to electrophoresis as described in Example 2. Proteins were detected by silver-staining. Protein molecular weight markers were run in lane "m".

One method of dissociating PEF complex into its component proteins is heat treatment. In the absence of heating, the majority of PEF migrates as a complex, running slightly slower than the 250 kD molecular weight marker. Minor amounts of dissociated P50 and P45 are visible in the unheated sample. However, after heat treatment at temperatures of about 85° C. or higher, the PEF complex is completely dissociated as indicated by the absence of the 300 kD band by SDS-PAGE. The predominant protein component of PEF complex, as visualized by silver-staining, exhibits an apparent molecular weight of approximately 50 kD in SDS-PAGE. The P50 band is shown in the gel of FIG. 7, where the protein was heated to ≧85° C. in the presence of 2% SDS and BME prior to loading. In addition, the P45 protein shown to be present in the gel-purified PEF complex (FIG. 6) is also evident in the heat-treated, S200-purified PEF sample (FIG. 7). Furthermore, minor components with apparent molecular weights of approximately 37, 42, 55, 60, 85, 100, and 150 kD were also detected in SDS-PAGE analyses of PEF complex treated at temperatures of 85-100° C. These minor components may represent additional forms of P50 and P45 generated by heat treatment (e.g. dimers, trimers, fragments) or minor unrelated species.

Figure 8:
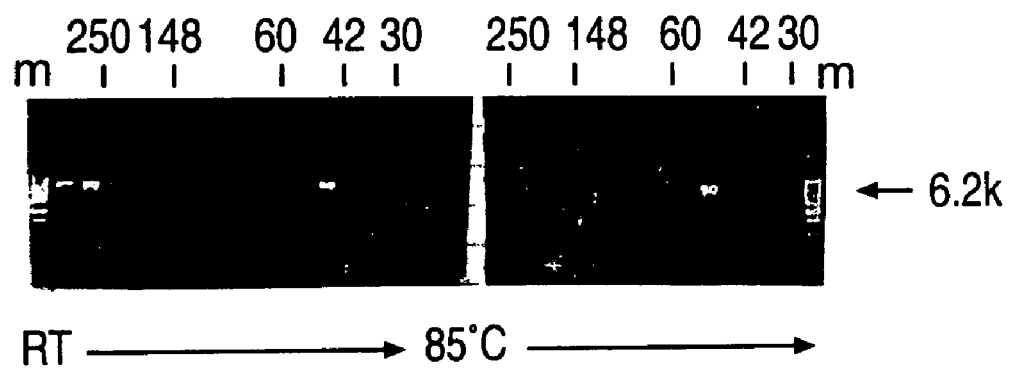
FIG. 8. PCR enhancing activity of SDS-PAGE gel-purified samples from an S200-purified *P. furiosus* PEF preparation (prep 1). Purified PEF (≈4.5 µg) was pre-incubated in 2% SDS for 3 minutes at room temperature (RT) or at 85° C. (85° C.) before electrophoresis. Proteins were eluted from SDS-PAGE gel slices 1-13 (gel RT) and 14-26 (gel 85° C.) as described in Example 2. One (1) µl of each gel slice, diluted 1:100 in cloned Pfu PCR buffer, was added to cloned Pfu PCRs as described in Example 1 (6.2 kb primer-template system). The approximate molecular weights of the SDS-PAGE gel-purified proteins is indicated at the top of the gel. DNA size markers were run in lanes "m".

2. Polymerase Enhancing Activity of PEF Complex and Component Proteins and Mixtures Protein components of S200-purified PEF were purified by SDS-PAGE and the PCR enhancing titer was determined by adding serial dilutions of each gel slice eluate to PCR reactions with cloned Pfu DNA polymerase PCR reactions. The protein or protein mixtures which exhibited the highest levels of polymerase enhancing activity were identified by running the eluates on silver stained SDS-PAGE gels. Analysis of SDS-PAGE gel slice eluates indicates that PCR enhancing activity of S200-purified *P. furiosus* PEF can be attributed solely to the 45 kD species plus the 50 kD species. When an S200-purified preparation was loaded in the absence of heating (FIG. 7, prep. 1), PCR enhancing activity was present in gel slices recovered just above the 250 kD marker and between the 42 and 60 kD markers. When heated to 85° C. before loading, PCR enhancing activity migrated between the 42 and 60 kD markers (FIG. 8).

Titration experiments showed that the PCR enhancing titer of gel purified proteins migrating with apparent mass between 42 kD and 60 kD was not significantly different from that of the gel-purified PEF complex (300 kD band). The levels of PCR enhancing activity migrating between the 148 and 60 kD markers were insignificant, thereby indicating that the 85 kD, 100 kD, and 150 kD bands do not contribute substantially to full PCR enhancing activity of the PEF complex (P300). Moreover, these components do not appear to further enhance the activity of PEF.

Figure 9:
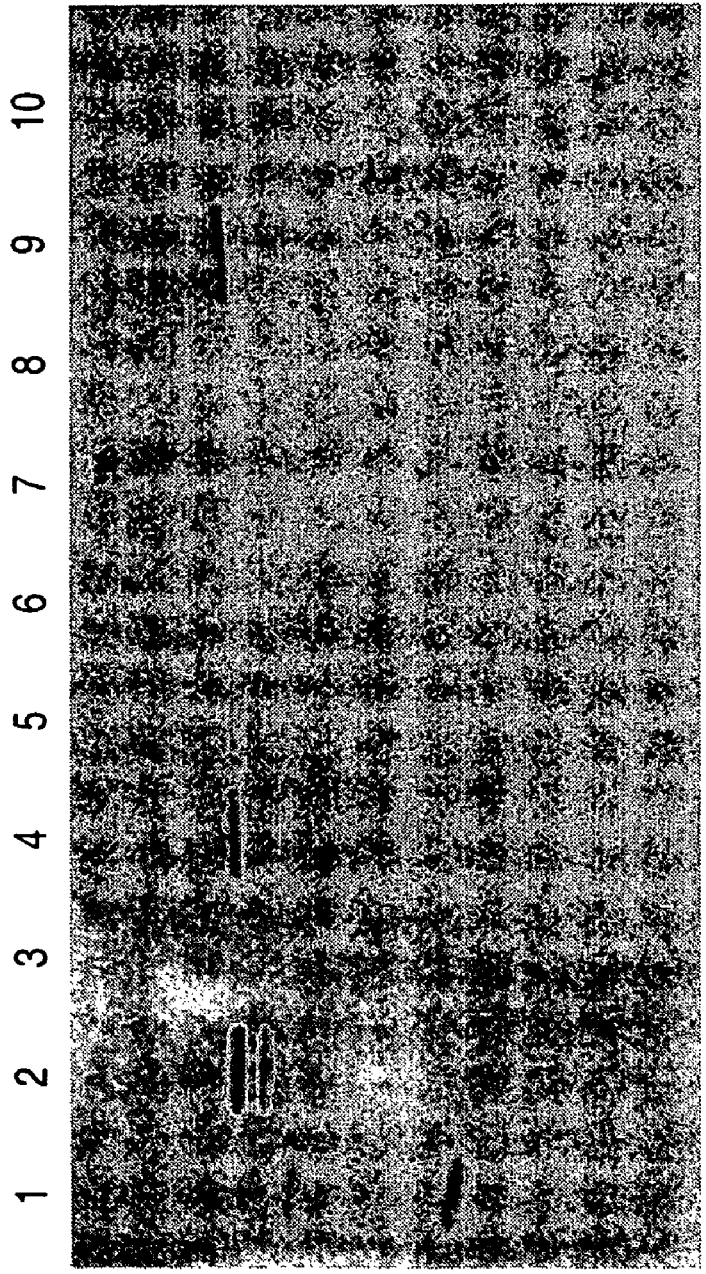
FIG. 9. S200-purified PEF (1.4 µg total protein) was heated at 85 or 100° C. prior to electrophoresis. Four slices were excised from the gel between the 60 kD (slice 1) and 42 kD (slice 4) markers. The proteins were eluted in 50 µl of buffer and 10 µl aliquots were boiled in the presence of SDS-BME loading dye and run out on 4-20% PAGE gels. Lane 1: Novex pre-stained markers; lane 2: 0.28 ng PEF; lanes 3-6: gel purified proteins isolated from S200-purified PEF heated at 85° C.-slice 1 (lane 3), slice 2 (lane 4), slice 3 (lane 5), and slice 4 (lane 6); lanes 7-10; gel purified proteins isolated from S200-purified PEF heated at 100° C.: slice 1 (lane 7), slice 2 (lane 8), slice 3 (lane 9), and slice 4 (lane 10).

FIG. 9 shows the proteins recovered from 4 gel slices between the 42 and 60 kD markers from 2 heated treated PEF samples. The greatest PCR enhancements were observed for protein samples run in lanes 5, 9, and 10. These lanes contained the highest amounts of P45, in addition to low but detectable amounts of P50. Relative P50 concentration did not necessarily correlate with highest PCR enhancing titer, as the proteins run in lane 4 (where only P50 is visible) exhibited a lower titer than the protein mixture in lane 5 (same amount of P50, plus P45). Moreover, samples in lanes 9 and 10 exhibited similarly high PCR enhancing titers and levels of P45, but the sample in lane 9 contained 10 to 1000-fold more P50 than the sample in lane 10. These results are consistent with P45 being the most active component of the PEF complex. Since all samples of gel purified P45 isolated contain varying concentrations of P50, the exact biochemical role a low concentration of P50 has on attaining full PEF activity or stability could not be determined by this method.

EXAMPLE 5

Amino Acid Analysis of PEF Complex and P50 and P45 Components

The complex and the predominate 50 kD component (P50) and 45 kD (P45) component from Pfu were sequenced at the N-terminus. In addition, N-terminal sequence analysis was performed on the minor 100 and 150 kD components generated upon heat dissociation. Two analyses were performed. In the first study, heparin sepharose-purified PEF samples (≈20% homogeneous; prep. 4 in FIG. 10) were electrophoresed and electroblotted onto PDVF filters. Samples were loaded onto 4-20% SDS-PAGE gels at room temperature or after heat treatment, to allow recovery of both the 50 kD protein and the >250 kD complex (FIG. 11). Blots were sent to Wistar Sequencing Facility (Philadelphia, Pa.) for analysis. N-terminal sequence analysis was performed on both the 50 kD (P50) protein (heated SDS-PAGE sample) and the >250 kD PEF complex (unheated SDS-PAGE sample).

The N-terminal amino acid sequences of the PEF complex (P300) and the 50 kD component (Pfu P50) were found to be substantially identical (Table A). This data confirmed that Pfu P50 is the predominant component of the PEF complex. Two distinct sequences were found for both P300 and P50 (1° and 2°), suggesting that Pfu PEF may contain 2 different 50 kD species which co-migrate, or that the PVDF strip containing the 50 kD species was contaminated with the 45 kD species or other species visible by SDS-PAGE.

In addition to the N-terminal sequencing, the 50 kD protein was also subject to in situ trypsin digestion and microbore reverse HPLC. A subset of tryptic peptides was analyzed by mass spec. Two peptides with single masses (#107, #112) and one peptide with two masses (#108) were chosen for sequence analysis. Two internal peptide sequences from Pfu P50 were recovered (Table A; Tryptic Peptides). Peptide #112 was 24 amino acids in length and the calculated mass of the Edman sequence (2530.8) was in very good agreement with the observed peptide mass (2531.7). Peptides #107 and #108 contained multiple sequences which could not be sorted by Edman sequencing alone. However these peptide fractions eluted very close together on microbore HPLC and contained several residues in common. Based upon shared sequence and mass analysis, a tentative sequence was assigned (107/108; Table A).

TABLE A

Analysis 1.
N-terminal Sequencing

| Protein Sample | Mass (Da) Obs. | | Sequence/(SEQ ID NO:) | |
|---|---|---|---|---|
| PEF complex | ≈50,000 | 1° | XLLHH VKLIY ATXXR | (1) |
| | | 2° | XXXPD WXXRX EXLXX | (2) |
| P50 | ≈50,000 | 1° | MLLHH VKLIY ATKSR RLVGK KIVLA IPGXI AAVEP | (3) |
| | | 2° | XXXPD WSXRX EXLGE KFY | (4) |

Tryptic Peptides

| Peptide | Mass (Da) Obs. | Calc. | Sequence/(SEQ ID NO:) | | Comments |
|---|---|---|---|---|---|
| 107 | 1389.59 | N/A | | | multiple sequences |
| 108 | 1659.1, 1910.63 | N/A | | | multiple sequences |
| 107/108 | — | 1910.3 | KYDAV IMAAA VVDFR PK | (5) | AAs common to 107/108 |
| 112 | 2531.73 | 2530.8 | ADLVV GNTLE AFGSE ENQVV LIGR | (6) | |

"X" represents any amino acid
underlined residues represent amino acids that may be deleted or substituted with any amino acid but are tentatively assigned as indicated The 35 amino acid sequence recovered from the N-terminus of Pfu P50 (SEQ ID NO.: 3), and the two internal peptides of 17 and 24 amino acids (SEQ ID NO.:s 5 and 6), represent approximately 16% of the total amino acid sequence of Pfu P50, assuming an apparent molecular weight of 50 kD and a length of approximately 454 amino acids.

Figure 12:
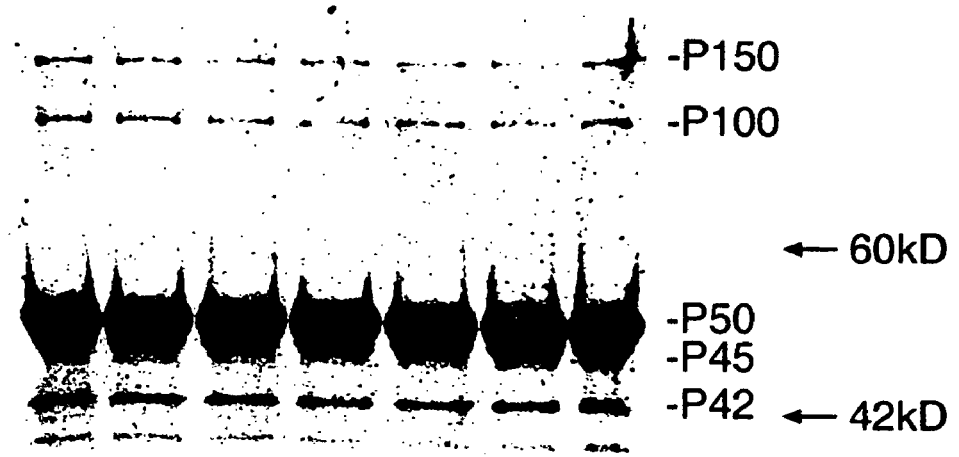
FIG. 12. PVDF blot of S200-purified *P. furiosus* PEF. Approximately 20 μg of total protein was electrophoresed in each of 7 lanes on a 12% PAGE gel. The samples were heated at 85° C. for 5 minutes prior to loading. The proteins were transferred to PVDF filters and stained as in the FIG. 11 legend.

In the second round of analyses, the N-terminal sequences of the 150, 100, 50, 45, and 42 kD species were determined from a PVDF blot of heated S200-purified PEF (FIG. 12 and Table B). This analysis was performed by the Beckman Research Institute of the City of Hope (Duarte, Calif.). The N-terminal sequences of the 150 and 100 kD species were the same and identical to the major sequence in the 50 kD band (except for ambiguity at the N-terminus) and similar to the minor sequence in the 45 kD band. In addition, the sequence was very similar to the major sequence in the PEF complex and the 50 kD band determined in the Wistar sequence analysis. The data are consistent with the 150 and 100 kD species being alternative forms of the 50 kD species (e.g., dimers, trimers, or aggregates). The major N-terminal sequence of the 45 kD band (2 blot sections analyzed; "upper" and "lower") was distinct from the P50 sequence and very similar to the minor sequence found in the 50 kD bands analyzed by both Wistar and Beckman and in the PEF complex analyzed by Wistar. No N-terminal sequence was recovered for the 42 kD species. In total, these data are consistent with the PEF complex consisting of 2 distinct protein components, P50 and P45.

TABLE B

Analysis 2.

| Protein sample (MW) | | Sequence | (SEQ ID NO) |
|---|---|---|---|
| 150 kD | | (GAM) LHHV KLIYA TKLRK | (7) |
| 100 kD | | (GAM) LHHV KLIYA TK (KL) RK | (8) |
| 50 | 1° | M LHHV KLIYA TKL | (9) |
| | 2° | GL (KL) PD W (WK) (KF) RK EES | (10) |
| 45 (upper) | 1° | (GAI) LLPD WKIRK EILIE | (11) |
| | 2° | XMHH (VI) KLXYA TXSRK | (12) |
| 45 (lower) | 1° | M (LY) (LV) (RP) D WKRRK EILIE | (13) |
| 42 | no sequence | | |

X represents any amino acid;
underlined residues represent amino acids that may be substituted with any amino acid but are assigned as indicated;
amino acids within parenthesis ( ) indicate that one of the enclosed amino acids is present at that site.

Using sequence information stored in a computer readable medium, one skilled in the art can perform computer-implemented homology searches. Here, the nonredundant GenBankCDS translations+PDB+SwissProt+SPupdate+PIR protein databases, using BLASTp, indicated that the partial amino acid sequence of Pfu P50 and P45 do not exhibit identity to any protein in those databases.

EXAMPLE 6

Nucleotide and Predicted Amino Acid Sequence of P50

The nucleotide sequence of the P50 protein component was obtained by cloning the Pfu P50 using standard techniques.

1. Library Screening

A *Pyrococcus furiosus* genomic library was plated on XL1-Blue MRF' *E. coli* at a density of approximately 2000 plaques per plate. Duralose filters (nitrocellulose on a nylon backing) were used to take replicate lifts from each plate. While the first filter was on the plate, orientation marks were made by stabbing a needle through the filter and into the plate. The orientation marks were marked in pen on the back of the plate before the filter was removed. The filter lifts were treated as follows:

| | |
|---|---|
| 1.5-2.0 minutes | 1.5 M NaCl, 0.5 M NaOH |
| 2 minutes | 0.5 M Tris (pH 8.0), 1.5 M NaCl |
| 30 seconds | 2xSSC, 0.2 M Tris (pH 7.5) |

After treatment, the filters were partially dried until they were still damp, but no standing waer was visible. The DNA on the filters was fixed by UV crosslinking with the Stratalinker set to the "Autolink" format.

The filters were prehybridized in 15 ml of:
5×SSC
40 mM NaPO₄ pH (6.5)
5× Denhardt's
5% Dextran Sulfate
50% Formamide
0.1 mg/ml Salmon sperm DNA (Boiled separately and added immediately prior to use) Prehybridization was carried out at 42° C. for approximately 2 hours.

Probe was generated from the 900 bp PCR product amplified from Pfu genomic DNA with the following degenerate primers:

```
                                        (SEQ ID NO:14)
Oligo #50:   CAT CAT GAA AAA CTA ATT TAC GC
              C   C   C       G T C
                              T       T (SEQ ID NO:15)
Oligo #61:   GC CAT AAT TAC TGC ATC GTA TTT
                 G   C   G   G
                 T   G   A
                     A
```

Oligo #50 was designed to hybridize to DNA encoding the HHVKLIYA (SEQ ID NO.: 66) peptide in SEQ ID NO.: 1, at the N-terminus of P50, while oligo #61 was designed to hybridize to the antisense DNA strand encoding the peptide KYDAVIMA (SEQ ID NO.: 67) in SEQ ID NO.: 5.

The PCR product was purified from free primers, buffer and nucleotides and 50 ng was labeled with ³²P-αdATP using the Stratagene Prime-It II Random Primer Labelling kit. The probe was purified from free nucleotides before being boiled for five minutes and added to the prehybridization reaction. The total probe was roughly calculated to be 80 million cpm.

Hybridization was allowed to continue overnight at 42° C. before the hybridization solution was removed and the filters were washed four times with 0.1×SSC, 0.1% SDS at 60° C. (stringent conditions).

The filters were exposed to X-ray film overnight and 20 primary isolates, with strong signals on both replicate filters, were picked.

Six primary isolates were diluted, plated, and screened again using the same method described above. Of the six, three filters produced isolated lambda clones. The clones were confirmed by PCR amplification using the degenerate primers. All clones were able to produce the 900 bp amplified by product with oligos #50 and #61, which was used as probe. Clones 6A and 3B produced a 1200 bp amplified fragment with oligos #54 and #58. Oligo #54 was designed to hybridize to DNA encoding the HHVKLIYA (SEQ ID NO: 66) peptide in SEQ ID NO: 1, and oligo #58 was designed to hybridize to the antisense DNA strand encoding with EENQVVL (SEQ ID NO.: 68) peptide to SEQ ID NO.: 6. Clone 6D only produced a 900 bp amplified product.

```
                                        (SEQ ID NO:16)
Oligo #54:   CAT CAT GAA AAA CTA ATA TAC GC
              C   C   C       G T C
                              T       T (SEQ ID NO:17)
Oligo #58:   AG TAC TAC TTG ATT TTC TTC
              A G   G   C   G
                A   A
```

Bluescript plasmid was excised from the lambda clones in SOLR cells and the presence of inserts confirmed again by PCR amplification of the 1200 or 900 bp product.

2. DNA Sequencing

Sequencing was carried out on purified PCR products and plasmid mini-preps made from the excised cells. The nucleotide sequence is listed below with the predicted protein translation. The peptide sequences used to generate the probes are indicated by underlining. "N" represents any base and "X" represents any amino acid.

(SEQ ID NO: 18)
ATGCTTCACCACGTCAAGCTAATCTACGCCACAAAAAGTCGAAAGCTAGT

TGGAAAAAAGATAGTCNNNNNNNNNNCCAGGGAGTATTGCGGCTTTGGATG

TGAAAGCTTGTGAGGGACTAATTAGGCATGGGGCCGAAGTTCATGCAGTG

ATGAGTGAGGCAGCCACCAAGATAATTCATCCTTATGCATGGAATTTGCC

CACGGGAAATCCAGTCATAACTGAGATCACTGGATTTATCGAGCATGTTG

AGTTAGCAGGGGAACATGAGAATAAAGCAGATTTAATTTTGGTTTGTCCT

GCCACTGCCAACACAATTAGTAAGATTGCATGTGGAATAGATGATACTCC

AGTAACTACAGTCGTGACCACAGCATTTCCCCACATTCCAATTATGATAG

CCCCAGCAATGCATGAGACAATGTACAGGCATCCCATAGTAAGGGAGAAC

ATTGAAAGGTTAAAGAAGCTTGGCGTTGAGTTTATAGGACCAAGAATTGA

GGAGGGAAAGGCAAAAGTTGCAAGCATTGATGAAATAGTTTACAGAGTTA

TTAAAAAGCTCCACAAAAAAACATTGGAAGGGAAGAGAGTCCTAGTAACG

GCGGGAGCAACAAGAGAGTACATAGATCCAATAAGATTCATAACAAATGC

CAGCAGTGGAAAAATGGGAGTAGCGTTGGCTGAAGAAGCAGATTTTAGAG

GAGCTGTTACCCTCATAAGAACAAAGGGAAGTGTAAAGGCTTTTAGAATC

AGAAAAATCAAATTGAAGGTTGAGACAGTGGAAGAAATGCTTTCAGCGAT

TGAAAATGAGTTGAGGAGTAAAAAGTATGACGTAGTTATTATGGCAGCTG

CTGTAAGCGATTTTAGGCCAAAAATTAAAGCAGAGGGAAAAATTAAAAGC

GGAAGATCAATAACGATAGAGCTCGTTCCNNNNNAATCCCAAAATCATTGA

TAGAATAAAGGAAATTCAACCAAATGTCTTTCTTGTTGGATTTAAAGCAG

AAACTTCAAAAGAAAAGCTTATAGAAGAAGGTAAAAGGCAGATTGAGAGG

GCCAAGGCTGACTTAGTCGTTGGTAACACATTGGAAGCCTTTGGAAGCGA

GGAAAACCAAGTAGTATTAATTGGCAGAGATTTCACAAAAGAACTTCCAA

AAATGAAAAAGAGAGAGTTAGCAGAGAGAATTTGGGATGAGATAGAGAAA

TTNCTGTCC

*Pyrococcus furiosus* P50 predicted amino acid sequence:

```
                                            (SEQ ID NO: 19)
MLHHVKLIYATKSRKLVGKKIVXXXPGSIAALDVKACEGLIRHGAEVHAV

MSEAATKIIHPYAWNLPTGNPVITEITGFIEHVELAGEHENKADLILVCP

ATANTISKIACGIDDTPVTTVVTTAFPHIPIMIAPAMHETMYRHPIVREN

IERLKKLGVEFIGPRIEEGKAKVASIDEIVYRVIKKLHKKTLEGKRVLVT
AGATREYIDPIRFITNASSGKMGVALAEEADFRGAVTLIRTKGSVKAFRI
```

-continued

```
RKIKLKVETVEEMLSAIENELRSKKYDVVIMAAAVSDFRPKIKAEGKIKS

GRSITIELVPXNPKIIDRIKEIQPNVFLVGFKAETSKEKLIEEGKRQIER

AKADLVVGNTLEAFGSEENQVVLIGRDFTKELPKMKKRELAERIWDEIEK

XLS
```

Translated sequence corresponding to chemically-determined N-terminal sequence (SEQ ID NO.: 3):

```
MLHHVKLIYATKSRKLVGKKIVXXXPGSIAA    (SEQ ID NO: 46)
```

Translated sequences corresponding chemically-determined internal peptide sequences

```
    KYDVVIMAAAVSDFRPK              (SEQ ID NO: 47)

ADLVVGNTLEAFGSEENQVVLIGR       (SEQ ID NO: 48)
```

The protein has a theoretical pI of 9.36 and a theoretical MW of 44801.29.

There are inconsistencies between the chemically-determined AA sequence of P50 and the AA sequence derived from the *P. furiosus* P50 genomic clone. One skilled in the art is familiar with many reasons for this type of inconsistency. For example, the inconsistencies below can, largely, be explained by known limitations common to the procedures used. These limitations do not operate to limit the structural knowledge of proteins or nucleic acids. Instead, they merely indicate possible variations in the sequences of amino acids or nucleic acids by a finite number.

Some of the inconsistencies and explanations are:

```
MLLHHVKLIYA TKSRR LVGKK IVLAI PGXIA AVEP    (Table A; SEQ ID NO:s 1 and 3)

MLHHV KLIYA TKL                             (Table B; SEQ ID NO: 9)

MLHHV KLIYA TKSRK LVGKK IVLAI PGSIA ALDV    (predicted sequence from SEQ ID NO.: 19)
```

The inconsistency in Table A sequence at cycle 2 (extra AA between AA1 and 2) may be due to contamination with P45, which appears to have L's at positions 2 and 3. Moreover, L at cycle 2 in SEQ ID NO: 1 was assigned tentatively. Other inconsistencies between the Table A sequence and the predicted sequence occur at AA 15 (R vs. K) and AA 32-34 (VEP vs. LDV).

An inconsistency between the Table B sequence and the predicted sequence was found at AA13. The identification of AA13 as L instead of S is explained by the poor recovery of S in chemical sequencing and the contamination of P50 with low amounts of P45, which has a L at that position.

```
ADLVV GNTLE AFGSE ENQVV LIGR    (Table A; SEQ ID NO: 6)
ADLVV GNTLE AFGSE ENQVV LIGR    (predicted sequence from SEQ ID NO.: 19)

KYDAV IMAAA VVDFR PK             (Table A; SEQ ID NO: 5)
KYDVV IMAAA VSDFR PK (predicted sequence from SEQ ID NO.: 19)
```

SEQ ID NO: 6, determined chemically from a P50 tryptic peptide, was identical to a 24 AA sequence translated from the P50 DNA sequence. For SEQ ID NO: 5, there were 2 inconsistencies found between the chemical and DNA sequences. An A was recovered at cycle 4 instead of a V, and a V was recovered at cycle 12 instead of a S. The inconsistencies may be due to the difficulties associated with interpreting sequences from a sample that is not absolutely pure.

EXAMPLE 7

Identification of Proteins Related to P50: Similarity to *E. Coli* DFP Flavoprotein 1. DNA Sequence Similarity of Pfu P50 Protein to Archael and Bacterial Proteins The DNA sequence of a P50 clone exhibits very strong homology to the flavoprotein DFP, a protein identified in *E. coli* as playing a role in DNA synthesis and pantothenate metabolism (Spitzer and Weiss, J. Bacteriol. 164:994-1003 (1985) and Spitzer, Jimenez-Billini, and Weiss, J. Bacteriol. 170:872-876 (1988)). Although DFP was found to be an essential gene for DNA replication, these authors were not able to elucidate its role in DNA replication. The sequences in Table 1 (N-terminal 1° sequence, tryptic peptides 107/108 and 112) are all found in the translated P50 clone, which exhibits very high similarity to DFP. Accordingly, the P50 amino acid and DNA sequence information can be used to identify related proteins associated with PEF complexes from other sources such as bacteria, eukaryotes, and archae.

The amino acid sequences of *Methanococcus jannaschii* (Mja) and *E. coli* dfp proteins support the identification of the protein designated P50 (Pfu) as a member of the dfp family of proteins. The three protein sequences were compared using ClustalW 1.6, with the comparison data represented below.

```
1 Pfu      1    ---------MLHH VKLIYATKSRKLVGK KIVXXXPGSIAALDV -KACEGLIRHGAEVH AVMSEAATKIIHPYA WNLPTGNPVITEITG      78
2 Mja      1    ------MISEIMHP TKLLKGTKSKLLENK KIILVAVTSSIAAIET PKLMRELIRHGAEVY CIITEETKKIIGKEA LKFGCGNEVYEITG         83
3 E. coli  1    MKARQQKYCDKIANF WCHPTGKIIMSLAGK KIVLGVSGSGIAAYKT PELVRRLRDRGADVR VAMTEAAKAFITPLS LQAVSGYPVSDSLLD        90
                              15    16                30 31               45 46              60 61              75 76               90

Page 2.1

1 Pfu      91   ----FIEHVELAGE HENKADLILVCPATA NTISKIACGIDDTPV TTVVTTAPPHIPIMI APAMHETMYRHPIVR ENIERLK-KLGVEFI      162
2 Mja      91   ----DIEHILLY-- --NECDCLLIYPATA NIISKINLGIADNIV NTTALMFGNKPIFI VPAMHENMFN--AIK RHIDKLKEKDKIYII         162
3 E. coli  91   --KWADLVILAPATA DLIARVAAGMANDLV STICLATP--APVAV LPAMNQQMYRAAATQ HNLEVLA-SRGLLIW                     173
                              105   106               120 121             135 136             150 151             165 166              180

Page 3.1

1 Pfu      181  GPRIEE------GKA KVASIDEIVRVIKK LHKKTLE-GKRVLVT AGATREYIDPIRFIT NASSGKMGVALAEEA DFRGAVTLIRTKGSV         245
2 Mja      181  SPKFEE------GKA KVANIEDVVKAVIEK IGNNLKKEGNRVLIL NGGTVEFIDKVRVIS NLSSGKMGVALAEAF CKEGFVVEVITAMGL         246
3 E. coli  181  GPDSGSQACGDIGPG RXXDPLTIVDMAVAH FSPVNDLKHLNIMIT AGPFPVRYIS NHSSGKMGFAIAAAA ARRGANVTLVSGPVS                 263
                              195   196               210 211             225 226             240 241             255 256              270

Page 4.1

1 Pfu      271  KAFRIRKIKLKVETV EEMLSAIENELRSKK YDVVIMAAAVSDFRP KIKAEGKIKSGRS-- --ITIELVPXNPKII DRIKEIQPN-VFLVG         330
2 Mja      271  EPPYYIKNHKVLTAK EMLNKAIE-L-AKD FDIIISSAAISDFTV ES-FEGKLSSEEE-- --LILKLKR-NPKVL EELRRIYKD-KVIIG         326
3 E. coli  271  LPTPPFVKRVDVMTA LEMEAAVN--ASVQQ QNIFIGCAAVADYRA ATVAPEKIKKQATQG DELTIKMVK-NPDIV AGVAALKDHRPYVVG         350
                              285   286               300 301             315 316             330 331             345 346              360

Page 5.1

1 Pfu      361  PKAETSK-EK-LIEE GKRQIERAKADLIVVG NTL----EAFGSEEN QVVLIGRDFTKELPK MKKRELAERIWDEIE KXLS----                450
2 Mja      361  FKAEYNLDEKELINR AKERLNKYNLNMIIA NDLSK--HYFGDDYI EVYIITKYEVEKISG SKK-EISERIVEKVK KLVKS----               403
3 E. coli  361  FAAETNN---VEEY ARQKRIRKNLLLDICA NDVSQPTQGFNSDNN ALHLFWQDGDKVLPL ERKELLGQLLLDEIV TRYDEKNRR               430
                              375   376               390 391             405 406             420 421             435 436
```

From the above comparison, it would be apparent to one of skill in the art that related proteins from other species can be identified and isolated by methods known in the art. The example above employed stringent screening conditions. Less stringent conditions, varying the concentration of salts, detergent, or the temperature during hybridization or washing, as known in the art, would lead to related clones from libraries containing sequences of any of a number of species. For example, in addition to the conditions described above, any of the following hybridization conditions can be used, in any combination, in methods to isolate DNA sequences related to the P50 or P45 sequences herein:

- low stringency wash in a solution comprising approx. 0.45 M NaCl, approx. 0.045 M trisodium citrate, and approx. 0.1% SDS, at approx. 37° to approx. 42° C.;
- hybridization buffer comprising approx. 0.75M NaCl, approx. 0.15 M Tris, approx. 10 mM sodium pyrophosphate, approx. 0.075 M trisodium citrate, and approx. 50% formamide;
- hybridization buffer comprising approx. 5×SSC, approx. 5× Denhardt's, approx. 5% Dextran Sulfate, approx. 50% formamide, and approx. 0.1 mg/ml ssDNA;
- hybridization wash comprising approx. 0.1 M phosphate, approx. 0.1×SET, approx. 0.1% sodium pyrophosphate, and approx. 0.1% SDS at approx. 45° C.

2. Absorbance Spectrum of Purified P. Furiosus PEF Complex

Figure 13:
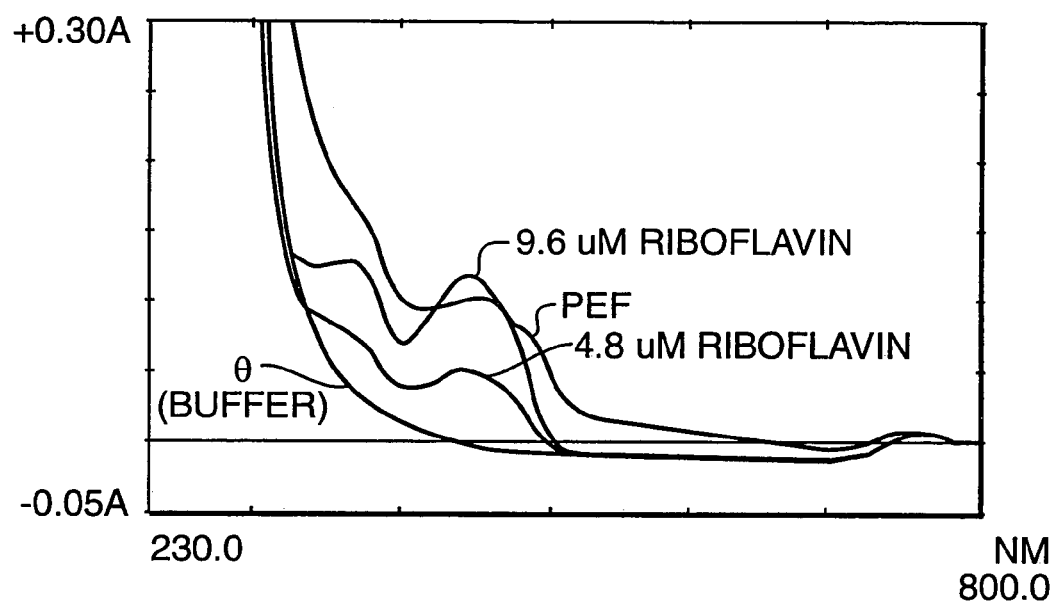
FIG. 13. Absorbance spectrum of S-200 purified *P. furiosus* PEF. The spectra of the following were obtained on a Shimadzu UV160U spectrophotometer: 0.7 mg/ml *P. furiosus* PEF, 9.6 μM and 4.8 μM riboflavin, and PEF final storage buffer (blank).

The absorbance spectrum of purified P. furiosus PEF complex reveals two peaks of absorbance at 370 and 450 nm. FIG. 13 depicts the absorbance spectrum of S-200 purified P. furiosus PEF. These data indicate and are consistent with the PEF complex comprising at least one flavoprotein. Sequencing data also verifies the identification of P. furiosus P50 as a homolog of the E. coli DFP protein. E. coli DFP is a flavoprotein containing a non-covalently associated FMN moiety.

Up to this point, flavoproteins have not been directly implicated as part of the replication machinery. The potential involvement of a flavoprotein in PCR enhancement suggests a role for redox reactions. The only redox reaction involved in DNA synthesis is the formation of deoxyribonucleotides from ribonucleotides, which is catalyzed by ribonucleoside diphosphate reductase. In vitro, the ribonucleoside diphosphate reductase enzyme can be coupled to NADPH via two known pathways involving FAD-containing oxidoreductases (Pigiet and Conley, J. Biol. Chem. 252:6367-72 (1977); Thelander and Reichard, Ann. Rev. Biochem. 48:133-158 (1979)). One pathway involves thioredoxin and thioredoxin reductase. Interestingly, E. coli thioredoxin has been shown to act as an accessory protein and confer processivity on T7 DNA polymerase. An alternate hypothesis for the potential role of a flavoprotein in PCR enhancement is that a flavoprotein may be required for the continuous processing or activation of other proteins or cofactors needed for nucleic acid replication.

EXAMPLE 8

Nucleotide and Amino Acid Sequence of P45

The nucleotide sequence of the Pfu P45 protein component was obtained as described below.

1. Synthesis of P45 Sequence

Amino terminal peptide sequencing of purified P45 protein allowed the generation of four degenerate oligonucleotides designed to hybridize to DNA encoding the PDWKIRKE (SEQ ID NO.: 69) peptide of SEQ ID NO.: 11, as follows:

```
#743:
CCA GAC TGG AAA ATA AGG AAA GA      (SEQ ID NO: 32)
    T       G   TGG
                            C
                            T

#744:
CCA GAC TGG AAA ATA AGA AAA GA      (SEQ ID NO: 33)
    T       G   TGG
                            C
                            T

#745:
CCA GAC TGG AAA ATA AGG AAG GA      (SEQ ID NO: 34)
    T       G   TGG
                            C
                            T

#746:
CCA GAC TGG AAA ATA AGA AAG GA      (SEQ ID NO: 35)
    T       G   TGG
                            C
                            T
```

A lambda phage P. furiosus genomic library was used as template for PCR amplification of the P45 sequence. The four degenerate oligonucleotides were used in separate reactions to prime template in one direction, in combination with one of the primers that border the genomic insertion of the lambda vector (−20 primer and reverse primer). The PCR reaction was carried out as specified below:

10 µl 10× Stratagene cloned Pfu buffer
5 µl degenerate P45 primer (either #743, 744, 745 or 746) at 100 ng/µl
2.0 µl either reverse or −20 primer (100 ng/µl)
0.8 µl 100 mM dNTP (total dNTPs)
0.5 µl Taq DNA polymerase (Stratagene, 5 u/µl)
0.5 µl Taq Extender (Stratagene, 5 u/µl)
3.0 µl Pfu genomic library (~1.2×10$^{10}$ plaque forming units/ml)
78.2 µl H$_2$O PCR cycling was carried out in a RoboGradient temperature cycler as follows: One cycle at 95° C. for 3 minutes, followed by 30 cycles of: 95° C. for 1 minute; 51° C. to 65° C. gradient for 2 minutes; 72° C. for 6 minutes.

The PCR products were separated on a 1% agarose, 1×TBE gel. All primer combinations produced multiple bands. A pattern of four bands was consistently seen with primers 743, 744, and 746 in conjunction with the −20 primer. The three degenerate primers that formed consistent four band patterns with the −20 primer were able to generate the pattern at 56° C. Only primer 743 could generate the pattern at 58° C. The band pattern produced with the degenerate primers in combination with the reverse primers was less distinct and formed only at lower annealing temperatures than the products generated with the −20 primer.

2. Cloning Strategies

Two strategies were used to isolate the P45 clone. One procedure was to make simplified sub-libraries of the original highly complex library and screen for an insert with the −20 and 743 primers. Positive sub-libraries could be diluted and rescreened until individual plaques containing the appropriate insert were identified. The other technique was to make use of Vectorette™ technology (Genosys Biotechnologies), which allows PCR amplification when the sequence of only one end of a DNA fragment is known. In the vectorette system, genomic DNA is digested with a selection of specific restriction endonucleases. After digestion, the ends of the genomic DNA are ligated to specific vectorette units, which have the same cohesive termini as the genomic DNA digestion. The ligated vectorette unit contains a sequence complimentary to a provided vectorette PCR primer. (Arnold and Hodgson, PCR Methods and Applications 1: 39-42 (1991).)

3. The Vectorette Reaction

Fifty µl reactions containing 100 ng of *P. furiosus* genomic DNA were digested with Eco RI, Hind III and Bsp 106I (an isoschizomer for Cla I) in their recommended buffers for one hour at 37° C. Without any post-reaction treatment, 1 µl of the appropriate vectorette unit (Hind III, Cla I or Eco RI at 3 pmole/µl) was added with 6 µl of 10 mM ATP, 1 µl of 100 mM DTT and 1 unit of T4 DNA ligase (Stratagene 4 u/µl). The reaction was cycled at the following temperatures: 20° C. for 60 minute followed by 37° C. for 30 minutes for 3 cycles.

The ligated DNA was amplified according to the following:

10 µl cloned 10× Stratagene Pfu buffer
8.3 µl degenerate P45 primer at 100 ng/µl
2.0 µl 50 pmol/µl vectorette primer
0.8 µl 100 mM (total) dNTP
0.5 µl Taq DNA polymerase (Stratagene, 5 u/µl)
0.5 µl Taq Extender (Stratagene, 5 u/µl)
1.0 µl vectorette library
76.9 µl $H_2O$ PCR cycling was carried out as follows: One cylce at 95° C. for 1 minute followed by 30 cycles of: 95° C. for 1 minute; 56° C. for 2 minutes; and 72° C. for 3 minutes.

Ten µl were loaded on an 1% agarose, 1×TBE gel. Multiple bands were produced by all primers except 745. To determine if all three vectorette library products had been correctly primed off the same target DNA (P45 sequence) rather than having been produced by a non-specific PCR reaction, the products were digested with Mnl I. Mnl I cleaves at a frequent four base pair recognition sequence and produces a useful pattern of bands specific to the template digested. The pattern generated by electrophoresis of the Mnl I digestion fragments of the Cla I/743, Hind III/744 and Eco RI/744 PCR products on a 6% acrylamide gel showed some variation, but the majority of bands could be identified in all three samples, indicating that they share large segments of identical sequence.

4. Screening

The PCR products from the Cla I/743 and Hind III/744 combinations were mixed and purified from free nucleotides and unused primers before being used as template for the generation of a 52 million cpm $^{32}P$ labeled probe. Details on probe synthesis and library screening are cited in Example 6.

More than 60 positive clones resulted from screening with the mixed vectorette probe. Several positive were well situated for collection without significant contamination from adjoining plaques. Twelve of these plaques were subjected to PCR amplification with the 743 and −20 primer as described previously except that an annealing temperature of 56° C. was used instead of a temperature gradient. In the same amplification assay, 11 sub-libraries were assayed in the same manner.

Three of the twelve clones recovered from the primary radioactive label screen produced strong, single bands. Clone 1 produced a band of approximately 5 kb, clone 3 produced a band of approximately 3.5 kb, and clone 9 generated a band of approximately 2.7 kb. One of the sub-libraries also produced a clone of approximately 6.5 kb.

5. Sequencing

Sequencing of the P45 clones was carried out on purified PCR products and plasmid mini-preps made from excised cells. The nucleotide sequence of P45 is listed below with the predicted amino acid translation. The chemically-determined N-terminal sequence of P45 (SEQ ID NO.: 11), used to generate the degenerate PCR primers (SEQ ID NO.: 32-35), is indicated by underlining.

```
P45 nucleotide sequence                                              (SEQ ID NO.: 70)
ATGCTACTTC CAGACTGGAA AATCAGAAAA GAAATACTTA TAGAGCCATT

TTCTGAAGAA TCGCTCCAAC CAGCAGGTTA TGACCTCAGA GTGGGCAGAG

AGGCTTTTGT TAAGGGGAAA TTAATCGACG TGGAAAAGGA AGGAAAAGTC

GTTATTCCTC CAAGGGAATA CGCCTTAATC CTAACCCTCG AGAGGATAAA

GTTGCCCGAC GATGTTATGG GGGATATGAA GATAAGGAGC AGTTTAGCAA

GAGAAGGGGT TATTGGTTCT TTTGCTTGGG TTGACCCAGG ATGGGATGGA

AACTTAACAC TAATGCTCTA CAATGCCTCA AATGAACCTG TCGAATTAAG

ATATGGAGAG AGATTTGTGC AGATCGCATT TATAAGGCTA GAGGGTCCGG

CAAGAAACCC TTACGAGGA AACTATCAGG GGAGCACAAG GTTAGCGTTT

TCAAAGAGAA AGAAACTCTA G

P45 amino acid sequence                                              (SEQ ID NO.: 71)
MLLPDWKIRK EILIEPFSEE SLQPAGYDLR VGREAFVKGK LIDVEKEGKV

VIPPREYALI LTLERIKLPD DVMGDMKIRS SLAREGVIGS FAWVDPGWDG

NLTLMLYNAS NEPVELRYGE RFVQIAFIRL EGPARNPYRG NYQGSTRLAF

SKRKKL*
```

The translated P45 protein has a theoretical pI of 9.12 and a calculated molecular weight of 17868.76. The translated N-terminal sequence (underlined) of P45 corresponds to the experimentally-determined sequence (SEQ ID NO.: 11) and matches the exact sequence (SEQ ID NO.: 60) used to design the degenerate PCR primers.

When the P45 DNA sequence is translated in all six frames and compared to multiple sequence databases using the computer-implemented program Blastx, the dCTP deaminase gene of *Desulfurolobus ambivalens* was found to have similarities. Another entirely different gene encoding polyprotein from Visna and Maeda/Visna virus was also identified, but at a less significant level of sequence similarity. Each of these similar genes, as well as those discussed below, may represent sequences related to P45. Thus, sequence information stored on computer readable medium may be used with computer based methods to search for homologous, similar, or identical sequences in a database to develop further P45 and PEF-encoding DNA sequences in accordance with this invention, as shown in example 9 below.

EXAMPLE 9

Identification of Proteins Related to P45

1. DNA Sequence Homology of *P. Furiosus* P45 Protein to dCTP Deaminase and dUTPases When the P45 DNA sequence was compared to multiple databases using the program BlastX, the probable deoxycytidine triphosphate deaminase (dCTP deaminase) gene (dcd) of *Desulfurolobus ambivalens* was found to exhibit the highest degree of similarity. The biochemical properties and physiological role of dCTP deaminase has been studied in *E. coli,* where dCTP deaminase is a homotetramer, which catalyzes the formation of dUTP and $NH_3$ drom dCTP. DNA sequences with similarity to the *E. coli* dcd gene have been discovered in other bacteria (*Salmonella typhimurium, Haemophilus influenzae*) and in archea (Ouzounis, C., Kyrpides, N., and Sander, C. Nucl. Acids Res. 23:565-570 (1995); Bult, C. J. et al. Science 273:1058-1073 (1996); Beck, C. J., Eisenhardt, A. R. and Neuhard, J., J. Biol. Chem. 250:609-616 (1975); Fleischmann, R. D. et al., Science 269:496-512 (1995)). Amino acid sequence comparisons between *P. furiosus* P45 and the dCTP deaminases from *Desulfurolobus ambivalens* ("A") (also known as *Acidianus ambivalens, Sulfolobus ambivalens*), *E. coli* ("E"), and *Haemophilus influenza* are shown below, demonstrating sequence similarity ranges from about 39.1 to about 71.2%.

MAP Multiple Sequence Alignment Results

Page 1.1

```
                15 16                        30 31                        45 46                        60 61                        75 76                        90
1 p45     MLLPDWKIRKE----  -ILIEPPSE-EWLQP AGYDLRVGXX XRVQR ----- -EAXVKGK--- -LIDVEK------- --EGKVXIPPREYAL          65
2 A.      MLIGDRDLKYYLEKG  WIVISPLTQ-DTIRE NGVDLRVGG--EIAR FKKTDEIYEDGKDPR SFYEIEK------- --GDEFIIYPNEHVL          77
3 E.      MRLCCDRDIEAWLDEG RLSINPRPPVERING ATVDVRLGNKFRTFR GHTAAFIDLSGPKDE VSAALDRVMSDEIVL DEGEAFYLHPGELAL          90
4 HAEIN   MRLCDTDIERYLDDG  IISLTPRPNNDKING ATIDVRLGNSFPVFR EHSAPFIDLSGPKEE VSAQLESVMSDEIII PEGEAFLHPGTLAL           90
```

Page 2.1

```
          91           105 106           120 121           135 136           150 151           165 166           180
1 p45     ILTLERIKLPDDVMG DMKIRSSLAREGVIG SFAW--VDPGWDGNL TLMLYNASNEPVELR YGERFVQIAFIRLEG PARNPYR----GNYQ         149
2 A.      LVTEEYVKLPNDVMA PVNLRSSFARLGLFV PPTI--VDAGPEGQL TIEVLG-SAFPVKIK RGTRFLHLIFARTLT PVENPYH----GKYQ         160
3 E.      AVTLESVTLIPADLVG WLDGRSSLARIGLMV HVTAHRIDPGWSGCI VLEFYNSGKLPLALR PGMLIGALSFEPLSG PAVRPYNRREDAKYR         180
4 HAEIN   ATTLESVKLPANIIG  WLDGRSSLARLGLMV HVTAHRIDPGWEGKI VLEFYNSGKLPLALR PNMVIGALSFRVLSG EXKRPYSSRKDAKYK         180
```

Page 3.1

```
          181          195 196          210 211          225 226          240 241          255 256          270
1 p45     GSTRLAFSKRKKL--                                                                                    162
2 A.      GQQGVTLPKFKFR--                                                                                    173
3 E.      NQQGAVASRIDKD--                                                                                    193
4 HAEIN   NQQSAVASRIDEDKE                                                                                    195
```

*E. coli* DCD exhibits an apparent molecular weight of 21.2 kD (Wang, L. and Weiss, B. J. Bacteriol. 174:5647-5653 (1992)), while the predicted molecular weight of *M. jannaschii* DCD is approximately 22 kD (204 amino acids). These molecular weights are approximately half the apparent molecular weight of *P. furiosus* P45 and suggest that the heat-dissociated form of P45 (apparent mol. weight of 45 kD) may actually be a dimer.

In addition to dCTP deaminase, *P. furiosus* P45 exhibits a significant, but lower degree of sequence similarity to uridine triphosphatase (dUTPase). dUTPase, an enzyme encoded by the dut gene, converts dUTP to pyrophosphate and dUMP. An amino sequence alignment comparing the sequence of P45 to several dUTPases is shown below. Regions of identity are shown in black boxes, while regions of similarity are shown in grey boxes.

```
p45           1                                                          ----MLPDWKIRKEILIEPFSEEWLQP
phage rI      1                                                          MTRGFKKINENATIPEAL-------EHS---
ECOLi         1                                                          ----MKKIDVMLDPYGKEFPLPLYAL-SGS---
HAEIN         1                                                          ----MKKIDVMLDSLGNEFPLPLYAT-EGS---
Scerevisiae   1                                                          ---MTATSDKVINIQLRSASATVPTKGS-ATA-
swine         1                                                          ------MSLYMKCVLSNNALIPNPSM--SGS--
tomato        1                                                          ---------TEPSPKVQKLDHPENGNVPFRVKEENPVTPSPAS-SLA-
variola       1                          MAENQINSPEI---------------------------------------PYA--
ORFN2         1                                                          ------MFNMNINSPVFVKENRAKSPTPS-PGA--
Rat           1                                                          ----------MPCSEET----PAISPSKRARPAEVGGMQKRFARMSEHATAPLGS-ARA--
EIAV          1                                                          ----MEFCHTETLQVVRSQNAT-PAPGS-PGA--
consensus     1       MPVLCALPRPTPTFSAPLAYAHVRAKPKLRRKQ-RSPDLERADRTRSADPAVSVSKRARAED--DASLFVPLSEHATAPTLPGS-ARA-
                                                                         ICGNQLADEAAKREEIMAYOGN--QIKEKRDED
                                                                         m   i       k  s   a  lptras          a p45          25     AGYDIRVCXXXRVGREAXVKGKLIDVEKGKVXLIRPYALILERKIDDVMCDNKI-PSLWREGVL-----CSFAWVLPGWDGN-LFLMYVASNEP
phage rI     23     AGYDLISAS------------ETVEICPDFIKMSIGLAVQGDDEVLKIYD-RSNPVFGIALINSVGLIDSDYPCEFKGLEMVISKP
ECOLi        28     ACDLDIRCL------------IDAVELAFGDTIIVPFSAILIPCIISHYTADPSLIAAMLPRSGFEH-IGIVLENLVGLIDSDYQCP-IMSWANRCPS
HAEIN        28     ACDLDIRALI-----------DESFEIQFGFTKLLIQFSFIVGTYGDL-IADPNLAAVILPRSGICHPEGIVICNLVGLIDSDYQGP-IMVSMNRCNEP
Scerevisiae  29     AGYDLYASQ------------G--ILKAMGOGMISIISFIVQKRDDICMIFSHVMPQGTVARIA-PRSGLSNYNNIDGG--IGIVFLNPCSD
swine        25     AGYDLYSAA------------GD-YEMVPYNRIVRDICTMLIFTSHVMPQGTVARIA-PRSGLAVKYSIDVGA--GVIDSDHGE-VKVLFEHSQRD
tomato       52     AGYDLYSAA------------GS-TKMFARGKALVPDILSHAVMPQGTVARIA-PRSGLAWKYSIDVGA--GVIDAYRGP-VGVIFLHSEVD
variola      30     ACDLDICSAY------------E-YEIPBGRQLLSQSMEKFCVGRVA-PRSGLACFCYGRIA-PRSGLAVHH-IDIGE--VGVIFLINECYT
ORFN2        29     AGYDLYSAY------------E-CVIFSHCSRWFTDLLHKPFSGCYGRIA-PRSGLACFCYGRVA-PRSGLAVHH-IDVGA--GVVDLFYGN-VGVVLFNFCNSD
Human        46     ACDLDICSAY------------E-YEIPEMKAWVKDPIHTALPSGCYGRVA-PRSGLACYCYGRVA-PRSGLAVAFH-IDVGA--GVIDEDYPGN-VGVVLFNFCBK
Rat          85     AGYDLYSAY------------E-YEISMRKAWVKDPIHTPDVKLQMPNSFCWVIG-KSSMAKQGLING--GINNECTGE--IQVVICNICKGN
EIAV         34     AGEDICVPY------------E-IMLVSDTKIHAPDVKLQIOMPNSFCWVIG-KSSMAKQGLING--GINNECTGE--IQVVICNICKGN
consensus   101     AGyDl say             d  tipp e  lv Tdl i lp  ygrma prsglavkr idgg gvid dyrgn lgvvlyN g e p45         120     VELEYGEEFVQLAHIKL-----NDDLANCKTCGFGSTGCEV-------
phage rI    101     VTHSKCRIMGQVEVKTIT-----FNLIEDNATDCEGFGHSGR-------
ECOLi       108     ITHIQCBHTAQLMIFVPWVQAEB-FNLIEDFOQITERGECGFGHSCK-------
HAEIN       108     IKLEVCDRIAQLNVFVPWVQALB-VDDAQLIVMDSIFESTFCAGGFGSTGN-------
Scerevisiae 100     FAHKCDRVAQLNLEKSAFNIHVCDRIAQLIEPVEHVI-XEEVKCLEDFERNSGFGSSGM-------
swine       127     FNHKCDRIAQLIQMIGFNVICDRIAQLIEPVEYI-XEEVKCLEDHERNSGFGSSGM-------
tomato      104     FENVICDRIAQLMQRYPE-HKEMQSESIDRCDQGFGSTGL------R-
variola     104     FEVKCDRIAQLICRYSCA-VQEVNCLENTDRCDSGFGSTCS------- GACCGRDTAWYIS-
ORFN2       121     FEVBKCDRIAQLICERLYPD-LBMQAHIDFPCSGFGSTCK--------N-
Human       160     FEVKCDRTIOELICER-FYPD-LEEMQTLENEPCSGGFGSTGK-------N-
Rat         108     IKLITECKFAQLIIIQ-HHSNSRQPWDENKISQPCDKGFGSTGVFWVENIQEAQDEHENWHTSPKILARNYKIPLTVAKQITQECPHCTKQGSGPAGCVM
EIAV        201
consensus           f  lk GdriaQlif ril pe i  v  ld  tdrg  ggfgstg
```

One of the regions of sequence similarity between P45 and dUTPase is the putative uridine-binding motif. This motif is conserved in the translated amino acid sequence of *P. furiosus* P45, which reveals the presence of a putative uridine-binding sequence conserved in ψ synthetases, dCTP deaminases, and dUTPases (Koonin, E. V. Nucl. Acids Res. 24:2411-2415 (1996)). In the following comparisons, U represents a bulky hydrophobic residue such as I, L, V, M, F, Y, or W, and the bolded residues match the G, D or U residues of the consensus sequence.

```
Consensus uridine- .GUUD..U.G.U.U    (SEQ ID NO.: 72)
binding motif:

P. fur. P45:       FAWVDPGWDGNTLM    (SEQ ID NO.: 73)

M. jann. DCD:      AGWIDAGFKGKITL    (SEQ ID NO.: 74)

M. jann put. DCD:  SAVHDPGYEGRPEY    (SEQ ID NO.: 75)

D. sulf. DCD:      PTIVDAGFEGQLTI    (SEQ ID NO.: 76)

E. coli DCD:       AHRIDPGWSGCIVL    (SEQ ID NO.: 77)

E. coli DUT:       VGLIDSDYQGQLMI    (SEQ ID NO.: 78)

Yeast DUT:         AGVVDRDYTGEVKV    (SEQ ID NO.: 79)

Human DUT:         AGVIDEDYRGNVGV    (SEQ ID NO.: 80)

Herpes virus DUT:  TGLIDPGFQGELKL    (SEQ ID NO.: 81)
```

Each of these proteins represent activities, such as dUTPase, that may be used as a polymerase enhancing activity or PEF. One skilled in the art can identify numerous other proteins using stored sequence information, in the appropriate computer readable medium, from this disclosure and analogous searching procedures in other databases. Database information on each of the following species can specifically be used to identify PEF using one or more of the sequences, or parts thereof, identified herein: *Pyrococcus furiosus*; *Pyrococcus horikoshii*; *Pyrobaculum aerophilum*; *Sulfolobus solfataricus*; *Archaeoglobus fulgidus*; *Aquifex pyrophilus*; *Methanococcus jannaschii*; *Thermotoga maritima*; *Methanobacterium thermoautotrophicum*; and *Thermus thermophilis*.

The physiological function of dCTP deaminase has only been studied in *E. coli*, where it plays an essential role in deoxyribonucleotide metabolism. dCTP deaminase converts dCTP to dUTP, which is an obligatory step in the de novo synthesis of thymidylate in bacteria (Taylor, A. F., and Weiss, B. J. Bacteriol. 151:351-357 (1982)). In turn, uridine triphosphatase (dUTPase encoded by the dut gene), a ubiquitous enzyme found in bacteria, eukaryotes, and eukaryotic viruses, degrades dUTP to pyrophosphate and dUMP, the thymidylate synthetase substrate. Thus, dCTP deaminase and dUTPase are functionally linked, with mutations in the dcd gene suppressing dut mutations (Wang, L. and Weiss, B. J. Bacteriol. 174: 5647-5653 (1992)).

uUTPase has shown to be an essential gene in *E. coli* and in yeast (El-Hajj, H. H., Zhang, H., and Weiss, B. J. Bacteriol. 170: 1069-1075 (1988); Gadsden, M. H., et al. EMBO J. 12:4425-4431 (1993)) because it functions in vivo to prevent dUTP incorporation into DNA. In *E. coli* dut mutants, the dUTP pool is greatly enhanced, resulting in an increased substitution of uracil for thymine in DNA during replication. Uracil-DNA glycosylase and exonuclease III play an essential role in repairing uracil-containing DNA in *E. coli* dut mutants (Taylor, A. F. and Weiss, B., J. Bacteriol. 151:351-357 (1982)).

The substrate specificities, enzyme activities, and physiological role of dCTP deaminase and dUTPase had not been characterized in archea prior to this disclosure.

EXAMPLE 10

Expression Cloning and Characterization of Recombinant P45

1. Expression Cloning of P45 by the Method of Ligation Independent Cloning (LIC)

Recombinant P45 was produced by PCR amplification of a portion of a P45 genomic clone (clone #9). The primers (oligos #1 and 2 below) were designed to function with the Affinity Protein Expression and Purification System (Stratagene; La Jolla, Calif.), which uses Ligation Independent Cloning (LIC).

```
oligo # 1.                                   (SEQ ID NO: 82)
5' GACGACGACAAGATGCTACTTCCAGACTGGAAA 3' oligo # 2.                                   (SEQ ID NO: 83)
5' GGAACAAGACCCGTCCCACTTTCACAGATGAAGAG 3'
```

The bold letter segments represent sequences specific to the cloning vector while the adjoining sequence is specific to the clone #9 sequence. The ATG underlined in oligo #1 corresponds precisely to the 5' end of the P45 gene, while the sequence after the bold letters in oligo #2 corresponds to the end of the genomic insert.

The PCR amplification was carried out in a volume of 100 µl containing: 1× Cloned Pfu Polymerase Buffer; 0.2 mM dNTPs (each); 200 ng of Primer oligo #1; 200 ng of Primer oligo #2; 3 µl Genomic clone #9 plaque core in 500 µl SM buffer (~2000 Lambda particles); 2.5 units Cloned Pfu DNA Polymerase; and 7 ng Native PEF (where 10× Cloned Pfu Polymerase Buffer is: 100 mM KCl; 100 mM (NH$_4$)$_2$SO$_4$; 200 mM Tris-Cl (pH 8.75); 20 mM MgSO$_4$; 1% Triton® X-100; and 1000 µg/ml BSA).

The thermocycling parameters were: 95° C. for 1 minute (1 cycle); 95° C. for 1 minute—56° C. for 1 minute—72° C. for 5 minutes (30 cycles).

The 2.5 kb amplified product was purified and then subjected to limited nucleotide excision in the presence of dATP. This protocol promotes removal of nucleotides at the 3' termini of the PCR product until an adenine residue is reached. The excision mixture (consisting of: 1× Cloned Pfu Polymerase Buffer; 0.5 mM dATP; 43.5 µl PCR product (8.7 ng/µl); 1.25 units Cloned Pfu DNA polymerase) was incubated at 72° C. for 10 minutes.

20 µl of the exonuclease treated PCR product was annealed with 40 ng of digested pCAL-n-EK vector (exonuclease treated to produce ends complimentary to the sequence exposed in the PCR product) for 45 minutes at room temperature. The amount of insert molar excess, relative to vector, was approximately 9 fold. The pCAL-n-EK vector contains an upstream, in-frame calmodulin binding peptide tag, which allows the N-terminal fusion protein to be easily purified on calmodulin agarose (CAM agarose). Various other expression vectors, which may or may not produce fusion proteins, are known in the art and can be used to express P45 protein or fragments thereof or to produce DNA constructs with a sequence encoding P45 protein or fragments thereof. An expression vector need only contain DNA sequences operating to permit or control transcription from an appropriately linked nucleic acid. The type of control, the degree of transcription permitted, and the manor in which the vector and nucleic acid are appropriately linked may vary. Generally, an expression vector also contains a replication control sequence to allow the vector to replicate in a host. However, replication control sequences are not required where replication of the host is not crucial to expression.

2. Purification of Recombinant P45

Five microliters of the annealed vector/insert DNA was transformed into XL2-Blue competent cells. Ten of the resultant colonies were screened by PCR for the 2.5 kb insert and 9 were found to contain the correct size insert. Plasmid DNA was prepared from three clones and then used to transform BL21 (DE3) cells. Six BL21 (DE3) colonies were grown for approximately 10 hours in 5 ml of 1×LB, 125 µg/ml ampicillin at 37° C. These cultures were used to inoculate six flasks containing 250 ml 1×LB and 125 µg/ml ampicillin. When the optical density ($OD_{600}$ values) of the cultures reached 1.1 to 1.3, IPTG was added to a final concentration of about 1 mM. The cells were grown overnight at 37° C. Cells were collected by centrifugation and the pellet estimated (visually) to be in the range 0.4-0.5 gm. The pellet was resuspended in 2.5 ml of calcium binding buffer: 50 mM Tris-HCl (pH 8.0); 150 mM NaCl; 10 mM β-ME; 10 magnesium acetate; 2 mM $CaCl_2$.

250 µl of 10 mg/ml lysozyme was added to the cells and the reaction was allowed to incubate on ice for one hour. The slightly lysed samples were sonicated twice with the Branson Sonifier 250, the microtip at a duty cycle of 50% and a setting of 4. The lysate was cleared by superspeed centrifugation. Cleared lysate was added to 700 µl of washed Stratagene Calmodulin agarose (50% CAM agarose by volume) and allowed to bind with gentle rocking at 4° C. for 1 hour. The resin was washed 3 times with 10 ml of $CaCl_2$ binding buffer and twice with 5 ml of the same solution except that the $CaCl_2$ concentration was reduced to 0.1 mM. Washing was accomplished by centrifugation, removal of the supernatant, and resuspension in fresh buffer. 5 µl of the CAM resin was collected to examine on SDS-PAGE electrophoresis. The washed matrix was resuspended in 900 µl of elution buffer [50 mM Tris-HCl (pH 8.0); 150 mM NaCl; 10 mM β-ME; 2 mM EGTA] and allowed to sit for one minute prior to pelleting of the agarose resin. The elution buffer containing P45 was removed to a separate tube and the CAM agarose was resuspended again in 900 µl of elution buffer. Next, a high salt elution buffer [50 mM Tris-HCl (pH 8.0); 1000 mM NaCl; 10 mM β-ME; 10 mM magnesium acetate; 2 mM EGTA] was used to elute remaining P45 protein from the CAM agarose:

Subsequent SDS-PAGE analyses showed that the high salt elution buffer released a majority of the recombinant *P. furiosus* P45 protein from the column matrices. Some residual protein remained bound to the calmodulin agarose.

The method described here to produce P45 protein can be modified in numerous ways by methods known in the art. (Ausubel, F. M., et al. (1989) Current Protocols in Molecular Biology, Greene Publishing Associates and Wiley-Interscience, New York, N.Y.; Sambrook, J., et al. (1989) Molecular Cloning: A Laboratory Manual, 2nd Ed., Cold Spring Harbor Laboratory Press, Cold Spring Harbor, N.Y.) In one possible modification, a P45 analog protein can be produced. For example, a mutation can be introduced into the P45 coding region. Any type of mutation can be used including site-specific point mutation, deletion mutation, insertion mutation, and multiples or combinations of these mutations. This mutant coding region is inserted into an appropriate vector, which is transferred into a host cell. The host cell then expresses the P45 analog. A P45 analog protein substantially retains one or more of the PEF activity or dUTP or dCTP metabolic activities described herein. Thus, the fusion protein and affinity tag expression and purification system described here is only one of many ways to produce a recombinant PEF protein such as recombinant P45.

3. Comparison of Recombinant P45 and Native PEF PCR Enhancing Activity

Figure 14:
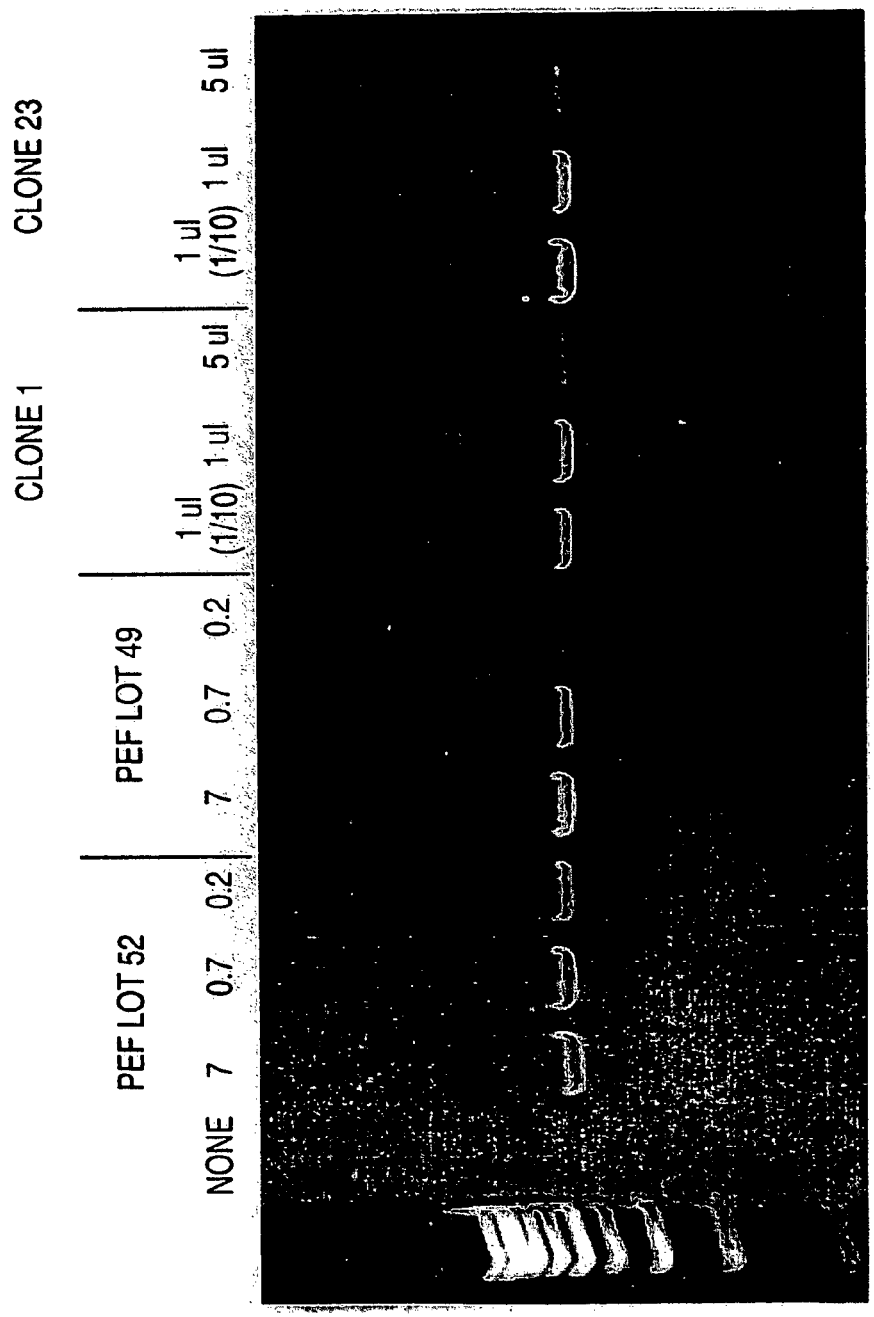
FIG. 14. Recombinant P45 (rP45) amplification enhancement of 5.2 kb fragment. In the 5.2 kb "On/Off" assay with PEF and rP45 samples, 7, 0.7 or 0.2 ng of the native PEF protein or 5 μl, 1 μl, or 1 μl of a 1/10 dilution of the rP45 protein (20 ng/ul) was added to the on/off assay.

The 5.2 kb "On/Off" assay, described in example 1, was used to demonstrate that recombinant P45 (rP45) possesses PEF activity comparable to a natural PEF. The results are shown in FIG. 14. When no PEF activity is added, the 5.2 kb amplification product is not generated as shown in the lane labeled "none" of FIG. 14. When proteins produced from the recombinant clones of P45 (called "1" or "23" from their plasmid delineation) were added to the On/Off assay in amounts of 5 µl, 1 µl, or 1 µl of a 1/10 dilution (approximately 100, 20 and 2 ng, respectively), they all showed enhancement of PCR product yield comparable to the two native PEF preps. Interestingly, 5 µl worked less well than 1 µl. An "overdose" phenomenon was also noted with native PEF (example 16).

Figure 15:
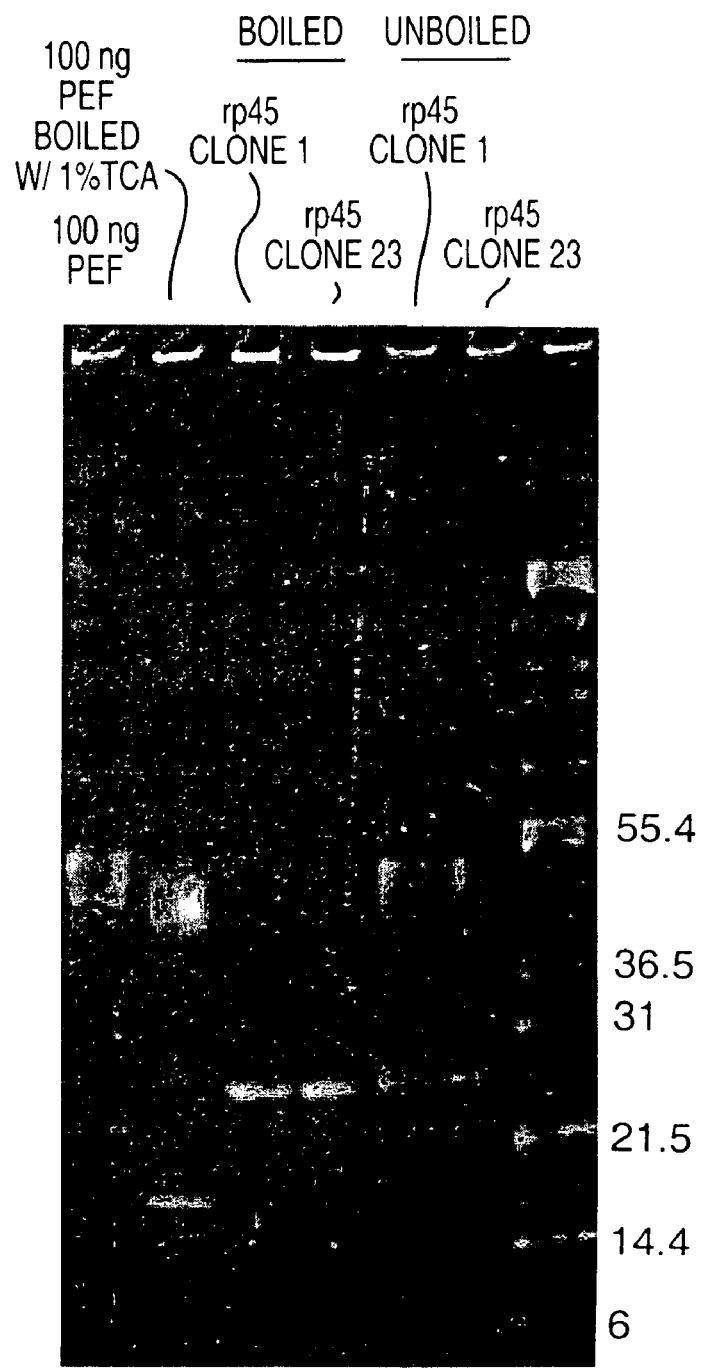
FIG. 15. SDS-PAGE analysis of fully denatured native PEF and rP45. The following protein samples were electrophoresed on 4-20% SDS-PAGE gels as described in the text: 100 ng native PEF, boiled in 2% SDS without (lane 1) or with 1% TCA (lane 2); 200 ng recombinant P45 clone 1, boiled in 2% SDS (lane 3) or loaded in the absence of heat-treatment (lane 5); 200 ng recombinant P45 clone 23, boiled in 2% SDS (lane 4) or loaded in the absence of heat-treatment (lane 6). The migration of molecular weight markers is shown in lane 7 (far right). The gel was stained with SYPRO orange dye (Molecular Probes), diluted 1:5000 in 5% acetic acid.
Figure 16A:
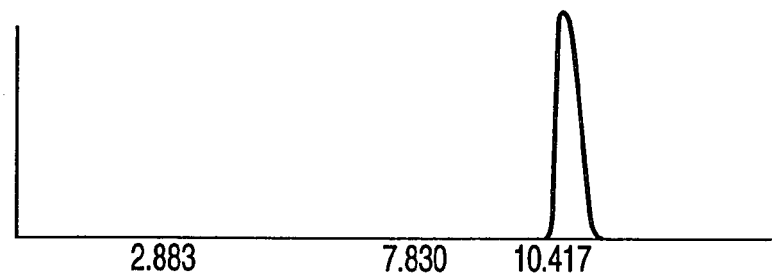
FIG. 16. Reverse Phase HPLC Analysis of dUTP Conversion by PEF and rP45. Panel A, dUTP heated at 72° C. in 1× cloned Pfu polymerase buffer (negative control). Panel B, dUTP heated in 1× cloned Pfu polymerase buffer with 700 ng native PEF. Panel C, dUTP heated in 1× cloned Pfu polymerase buffer with 5 μl of rP45 (clone 1), Panel D, dUMP standard heated in 1× cloned Pfu buffer, Panel E, the products shown in panel B and panel D were mixed and injected simultaneously to demonstrate, through the production of a single peak, that dUMP migrates identically to the PEF byproduct.
Figure 16B:
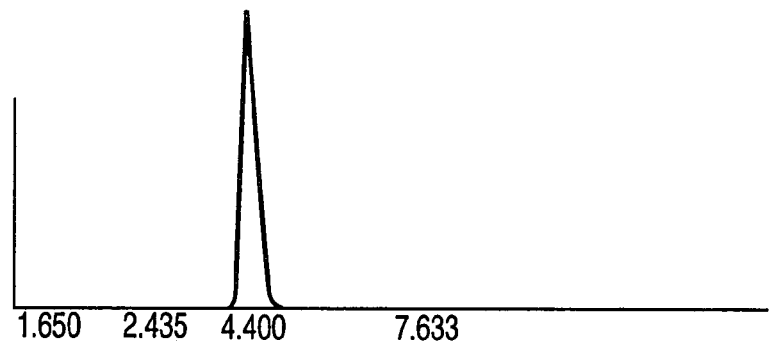
Figure 16C:
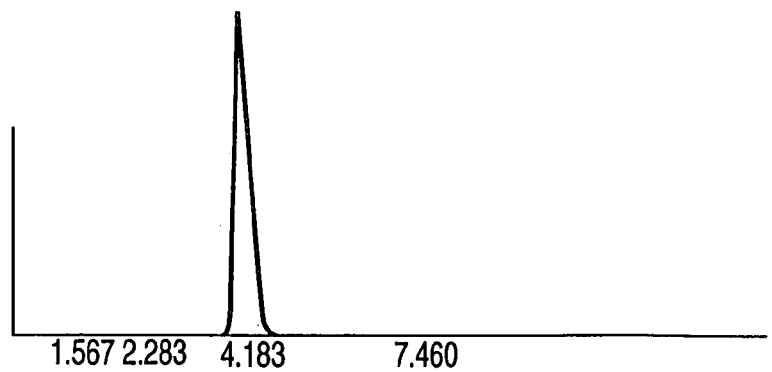
Figure 16D:
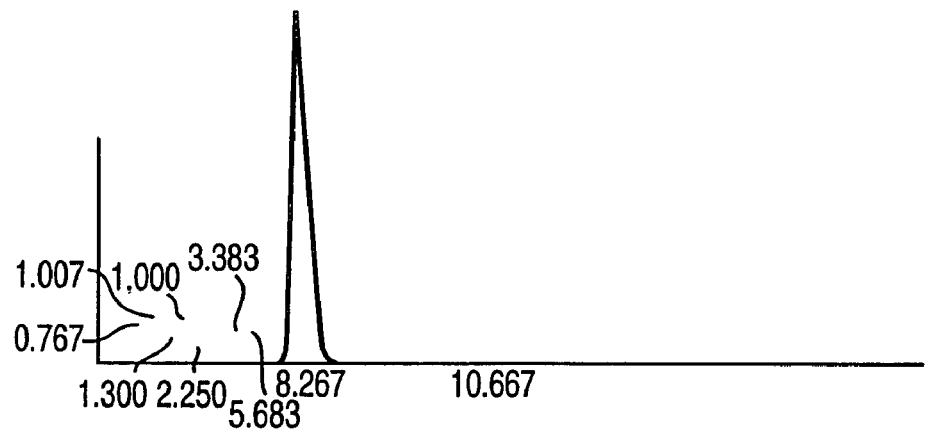
Figure 16E:
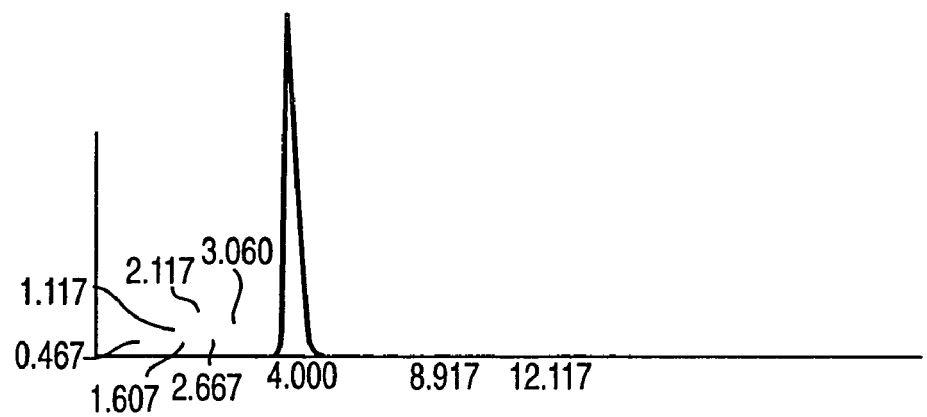

4. Molecular Weight of Recombinant P45 Compared to Native PEF Complex and Protein Components of the Complex The predicted molecular weight of the translated rP45 DNA sequence was 18.6 kDa. However, the native P45 component migrates as part of the PEF complex at 300 kDa without heat denaturation, and at 45 kDa with heat denaturation (99° C. for 5 minutes, partially denatured). Protein complexes in hyperthermophiles are unusually stable and sometimes require extreme conditions before disassociation occurs. We have found that P45 migrates at approximately 18 kD, or approximately 17-18 kD, instead of 45 kD when the native PEF complex is boiled in the presence of 2% SDS and 1% trichloroacetic acid (TCA) (fully denaturing conditions) (FIG. 15). Without heat denaturation, more than half of the recombinant P45 migrated at approximately 50 kDa (45+4 kDa calmodulin binding tag), while the remaining sample migrated close to 26 kDa (FIG. 15). With heat denaturation all of the sample migrated at approximately 26 kDa, suggesting that the recombinant is a dimer in its undenatured state. Trichloroacetic acid heat treatment failed to produce any additional bands in the recombinant sample.

The migration differences between the fully denatured forms of the native (18 kD) and recombinant P45 (26 kD) might be explained by differences in post-translational modifications between *P. furiosus* and the *E. coli* host or by the effects of the 4 kD CBP (calmodulin binding protein) tag on the folding or migration of the rP45 fusion protein.

EXAMPLE 11

Potential Mechanisms of PCR Enhancement by P45

1. Identification of the Reaction Catalyzed by PEF/P45

The similarity of P45 to dCTP deaminases prompted us to test whether dCTP or other nucleotide triphosphates were substrates of PEF/P45. PEF was incubated with dCTP or dUTP and the reaction products were separated by reverse phase HPLC. Reaction mixtures (50 µl) containing 1× cloned Pfu polymerase buffer, 10 mM dCTP or dUTP, and 700 ng PEF (or 5 µl of cloned p45 (~100 ng) or nothing (neg. control) were incubated at 72° C. for 1 hour. The samples were injected on a 3.9×250 cm Waters Delta-pak C-18 column (300 angstrom/15 µm), equilibrated in 50 mM triethylammonium acetate, pH (7.0) (A). Products were eluted with acetonitrile (B) at 2 ml/min. using the following gradient: 0% B for 5 minutes, 0-10% B over 20 minutes. Absorbence of the eluate was monitored with a photodiode array detector, and peak areas were integrated at 260 nm.

The data in FIG. 16 show that both the native PEF complex and purified recombinant p45 utilize dUTP as a substrate. In the presence of cloned Pfu DNA polymerase PCR buffer, dUTP migrates at 10.517 minutes. After a one hour incubation with PEF or recombinant P45 (purified from clone 1 or 23), the dUTP peak disappeared (0.1% total peak area) and a new peak appeared eluting at 4.400 minutes (98% total peak area). The product of the PEF+dUTP reaction migrated with the same retention time as a dUMP standard, which was different from the retention times of dUDP, dCMP, dCDP, and dCTP. To confirm that the product was dUMP, a dUMP standard and the PEF+dUTP product were mixed together and re-injected. The mixed sample produced only one peak.

Figure 17:
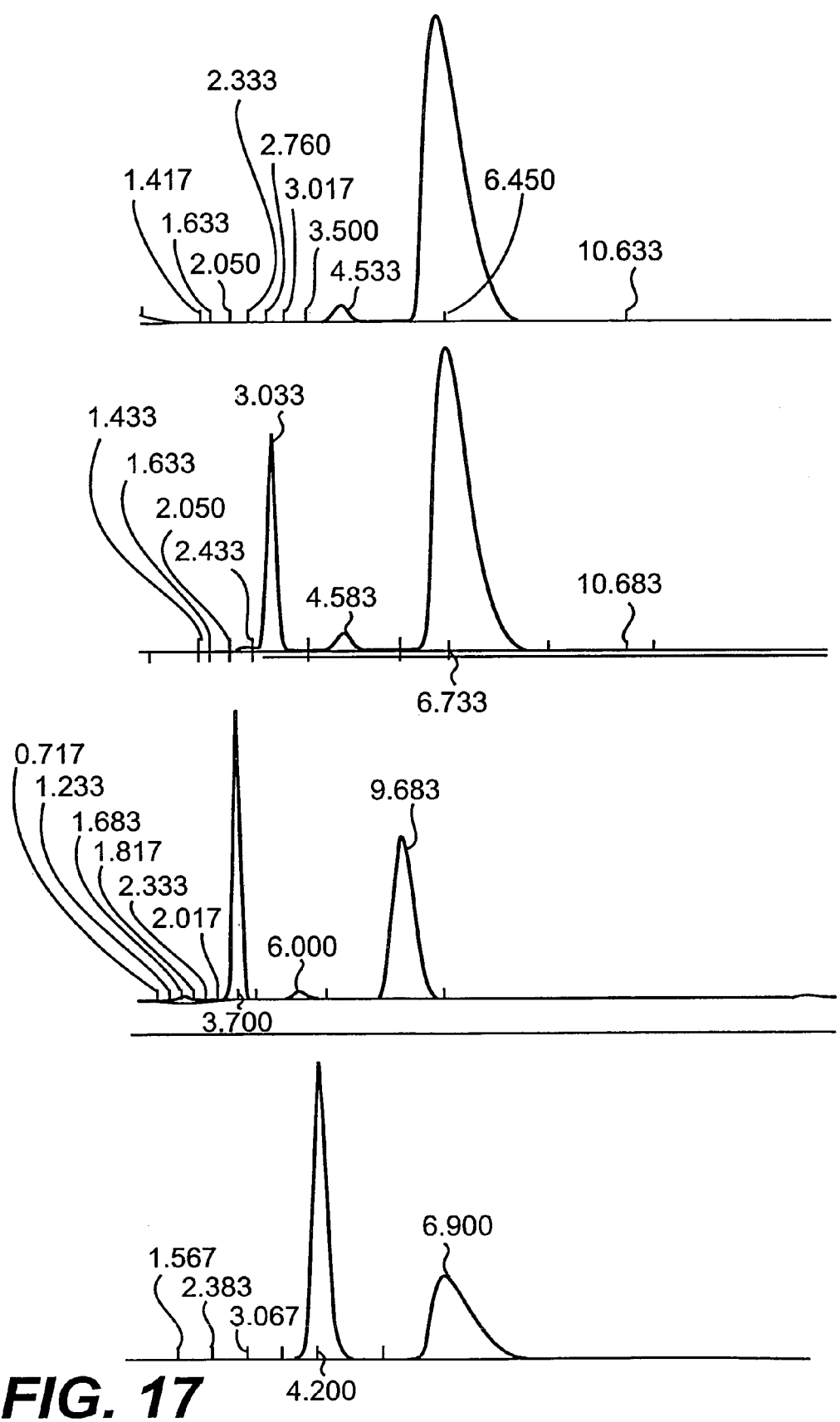
FIG. 17. Reverse Phase HPLC Analysis of dCTP Conversion by PEF and rP45. Panel A, dCTP heated in 1× cloned Pfu polymerase buffer without additive (negative control), Panel B, dCTP heated in 1× cloned Pfu polymerase buffer with 700 ng of PEF. Panel C, dCTP heated in 1× cloned Pfu polymerase buffer with 5 μl of rP45. Panel D, dUTP and dCTP heated in 1× cloned Pfu polymerase buffer with 700 ng of PEF. Chromatograms in panels A, B and D, were performed in the same series, while chromatogram C was performed in a different experiment, using a different C-18 column. In the second experiment a dCTP standard was shown to elute at 9.6 minutes (data not shown).
Figure 18A:
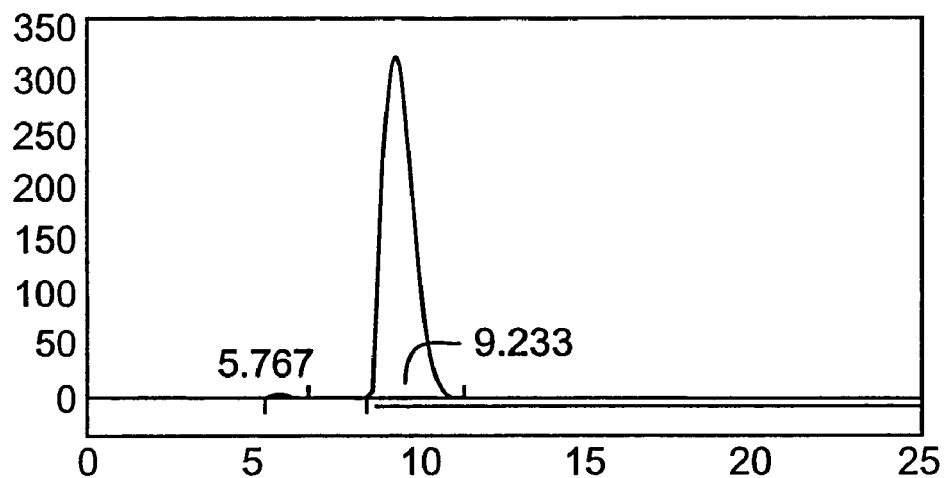
FIG. 18. Reverse phase HPLC analysis of the products generated by heat-treatment of dCTP. dCTP (10 mM in cloned Pfu DNA polymerase PCR buffer) was heated at 95° C. in thin-walled tubes in a RoboCycler 40 temperature gradient block. Incubations were carried out for the following length of time: 0 (panel A), 1 hour (panel B), or 4 hours (panel C). 10 μl of the reaction mixtures were loaded onto a Waters Delta-pak C-18 column (300 angstrom/15 μm), equilibrated in 50 mM triethylammonium acetate, pH(7.0) (A). Products were eluted with acetonitrile (B) at 2 ml/min., using the following gradient: 0% B for 5 minutes, 0-10% B over 20 minutes. Absorbence of the eluate was monitored with a photodiode array detector, and peak areas were integrated at 260 nm. To the right of panels A and C are shown the same chromatograms re-integrated at a higher sensitivity. In panel D, 10 μl of 10 mM dUTP (in cloned Pfu DNA polymerase PCR buffer) was chromatographed.
Figure 18B:
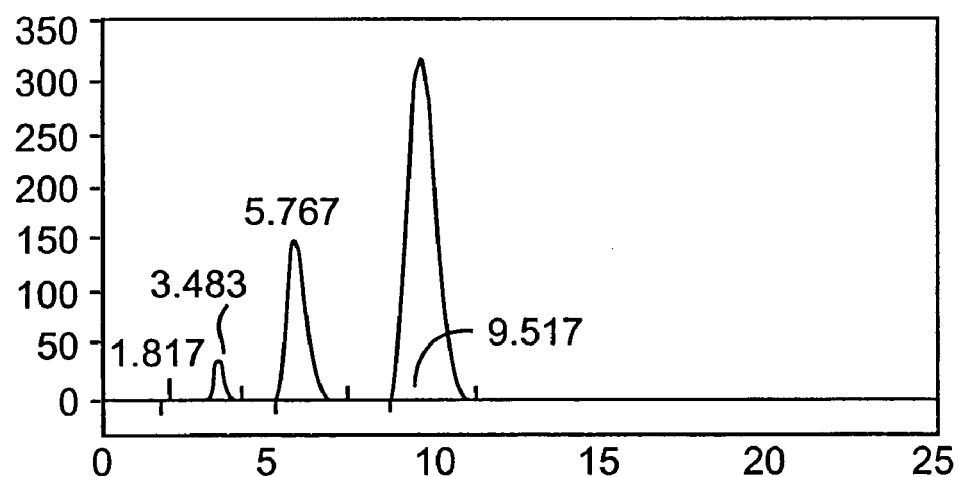
Figure 18C:
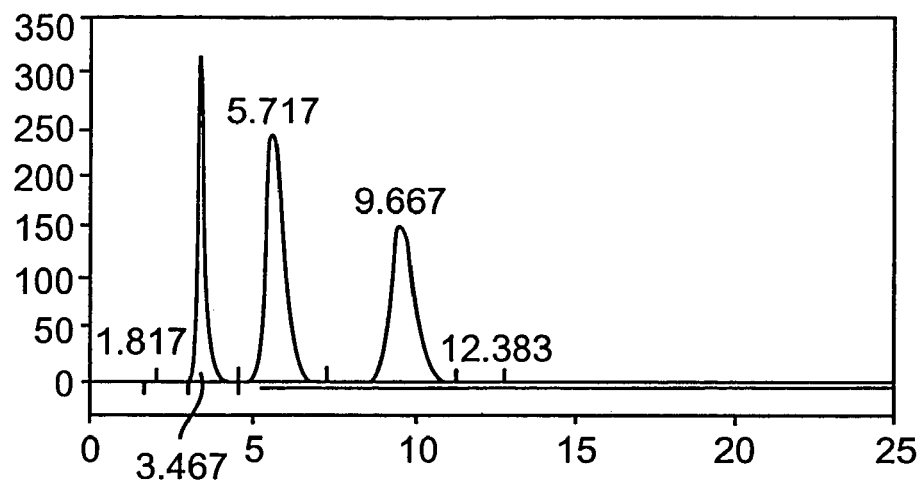
Figure 18D:
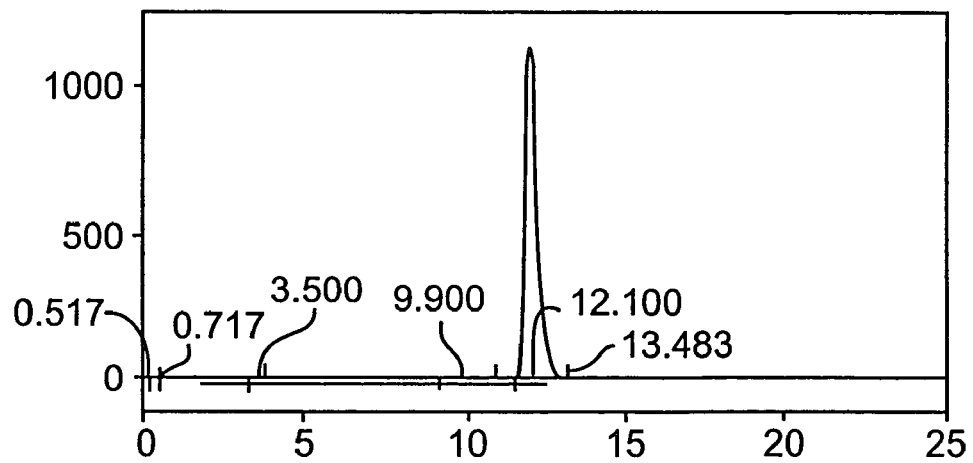

In addition to dUTP, dCTP was also found to serve as a substrate for PEF (FIG. 17). The product of the PEF+dCTP reaction appeared to be dCMP, based upon its retention time and absorbence maxima. Although PEF utilizes dCTP, dUTP is the preferred substrate of PEF/P45. In the example shown, only 16.6% of the dCTP was converted in 1 hour under the same conditions which converted 100% dUTP (FIG. 17, panel B). Moreover, when dCTP and dUTP were incubated together with PEF, only dUMP (4.2 minute peak in panel C) was generated. No reactivity with PEF was detected for the following nucleotides: dGTP, dATP, dTTP, dCMP, dUMP, and rUTP under the conditions used.

The substrate preference and reaction catalyzed by PEF/P45 was significantly different from that predicted based upon the amino acid similarity to dCTP deaminases. Although both enzymes bind dCTP and dUTP, the forward reaction catalyzed by dCTP deaminase is the deamination of dCTP to produce dUTP+$NH_3$. PEF/P45, on the other hand, preferentially utilizes dUTP, and catalyzes the release of pyrophosphate (PPi). No deamination of dCTP by *P. furiosus* PEF or P45 was observed under the conditions used.

2. Enzymatic Detection of Inorganic Pyrophosphate ($PP_i$) Produced by PEF from dUTP We tested whether inorganic pyrophosphate ($PP_i$) or inorganic phosphate ($P_i$) was generated during the PEF-catalyzed conversion of dUTP to dUMP (FIG. 16). To assess whether $P_i$ was produced, 900 or 1800 ng of PEF was incubated in the presence of 5 mM dUTP in 1× cloned Pfu polymerase buffer for 1 hour at 72° C. The reaction mixture was subsequently analyzed for the presence of $P_i$ using the method of Heinonen and Lahti (Heinonen, J. K. and Lahti, R. J. (1981) Anal. Biochem. 113: 313-317). Previous results (HPLC) demonstrated that under the above reaction conditions, 100% of the dUTP should be converted to product. One hundred percent (100%) conversion corresponds to the production of 500 nmol of $P_i$, if $P_i$ is a product of the reaction. However, no $P_i$ was detected in these assays. The assay for $P_i$ was sensitive enough to detect as little asabout 50 nmoles of $P_i$. These observations show that $P_i$ is not formed during the reaction of PEF with dUTP.

In experiments to investigate whether $PP_i$ is formed during the reaction, 900 or 1800 ng of PEF was incubated with 10 mM dUTP in 1× cloned Pfu polymerase buffer for 1 hour at 72° C. The presence of $PP_i$ in the reaction mixture was then quantified using Sigma's "Enzymatic Determination of Pyrophosphate" kit (Sigma Product No. P7275). The kit utilizes a coupled enzyme system whereby two moles of NADH are oxidized to $NAD^+$ for each mole of $PP_i$ present in the reaction mixture. The oxidation of NADH is monitored spectrophotometrically at 340 nm. Using this assay system, the production of $PP_i$ was clearly established in reactions that contained PEF and dUTP. No $PP_i$ was detected in control reactions that lacked PEF or that contained PEF and dATP (in place of dUTP). The reactions that contained 1800 ng of PEF produced twice as much $PP_i$ as those that contained 900 ng of PEF.

The temperature optimum ($T_{opt}$) for the generation of PPi from dUTP was measured by incubating mixtures of dUTP and native PEF at temperatures ranging from 73° C. to 99° C. PPi production by native PEF increased steadily over this temperature range and was highest at 99° C. While the $T_{opt}$ for native PEF was found to >99° C., recombinant P45 exhibited maximal activity between 85° C. and 93° C. when tested at the same enzyme concentration (dUTP turn-over), but at a lower total protein concentration. Accordingly, specific temperature ranges, such as from about 70° C. to about 100° C., from about 85° C. to about 93° C., or temperatures above about 70° C., can be used with a PEF or polymerase enhancing activity of the invention.

The enzyme activity of three different preparations of S200-purified native PEF was measured at 85° C. Protein concentrations were determined by both Bradford and by amino acid analysis. Shown below is a summary of the enzyme activity and specific activity (protein concentration determined by Bradford or AAA as indicated) of S200-purified native PEF. These activities were compared to the minimum amount of purified PEF required to amplify the 5.2 kb target in the "on/off" assay described in example 1 (100 µl PCR).

| Prep | PPi production (µ mole PPi/hr/µl) | Specific activity (µ mole PPi/hr/µg) (Bradford) | Specific activity (µ mole PPi/hr/µg) (AAA) | Minimum amount of dUTPase required for 5.2 kb PCR (nmole PPi/hr) |
|---|---|---|---|---|
| 1 | 1.23 | 1.76 | 4.03 | 0.11 |
| 2 | 0.27 | 0.59 | 3.13 | 0.11 |
| 3 | 0.14 | na | 1.37 | 0.22-0.44 |

The data indicate that for purified PEF preps 1 and 2, there is an excellent agreement between dUTPase activity and PCR enhancing activity. However, native PEF prep 3 exhibited 2-4 times less PCR enhancing activity, possibly due to its lower specific activity. Prep 3 may contain contaminants, which interfere with PCR enhancement.

PPi formation from dCTP was also measured by substituting dCTP for dUTP. For native PEF prep 1, the level of dCTPase activity was found to 0.097 (µmole PPi/hr/µl) at 85° C., which is 12-fold lower than the rate of PPi production from dUTP. In addition, recombinant P45 preparations were also tested and found to produce PPi from both dUTP and dCTP. Native PEF and recombinant P45 exhibited a similar degree of preference for dUTP, as compared to dCTP.

Therefore, recombinant P45 and structurally similar P45 proteins catalyze this reaction in the absence of any of the other components of the PEF complex. The methods described here for the $PP_i$ detection are, thus, a useful tool for analyzing the activity of or determining the presence of native PEF, PEF analog proteins, recombinant or synthetic PEF proteins, PEF complexes, and rP45.

3. PEF/dUTP Product Characterization with Mass Spectrometry

Electrospray mass spectral analysis was performed to characterize the byproduct of reactions employing PEF and dUTP. Analysis in the negative ionization mode produced a relatively clean spectrum exhibiting peaks at 307 and 615 m/e. These masses are consistent with those of dUMP [M—H]⁻ and its non-covalent dimer [2M—H]⁻. Analysis in the positive mode gave a complex array of peaks.

4. Role of PEF/P45 in Eliminating dUTP Accumulation During PCR

An understanding of the catalytic activity of PEF/P45 has provided insight into the mechanism by which PCR enhancement occurs. Lasken et al. have reported that archeal DNA polymerases, such as Vent, incorporate dUTP at approximately 40% the rate of TTP (Roger S. Lasken, David M. Schuster, and Ayoub Rashtchian, (1996) J. Biol. Chem. 271; 17692-17696). However, further DNA synthesis by archeal DNA polymerases appears to be inhibited by dU-containing DNA. Inhibition appears related to the 6500-fold greater affinity of Vent for dU-containing sites, as compared to dT-containing DNA. Based upon these observations, Lasken has proposed that archeal DNA polymerases may play a role in repairing dU-containing DNA in vivo.

Figure 19:
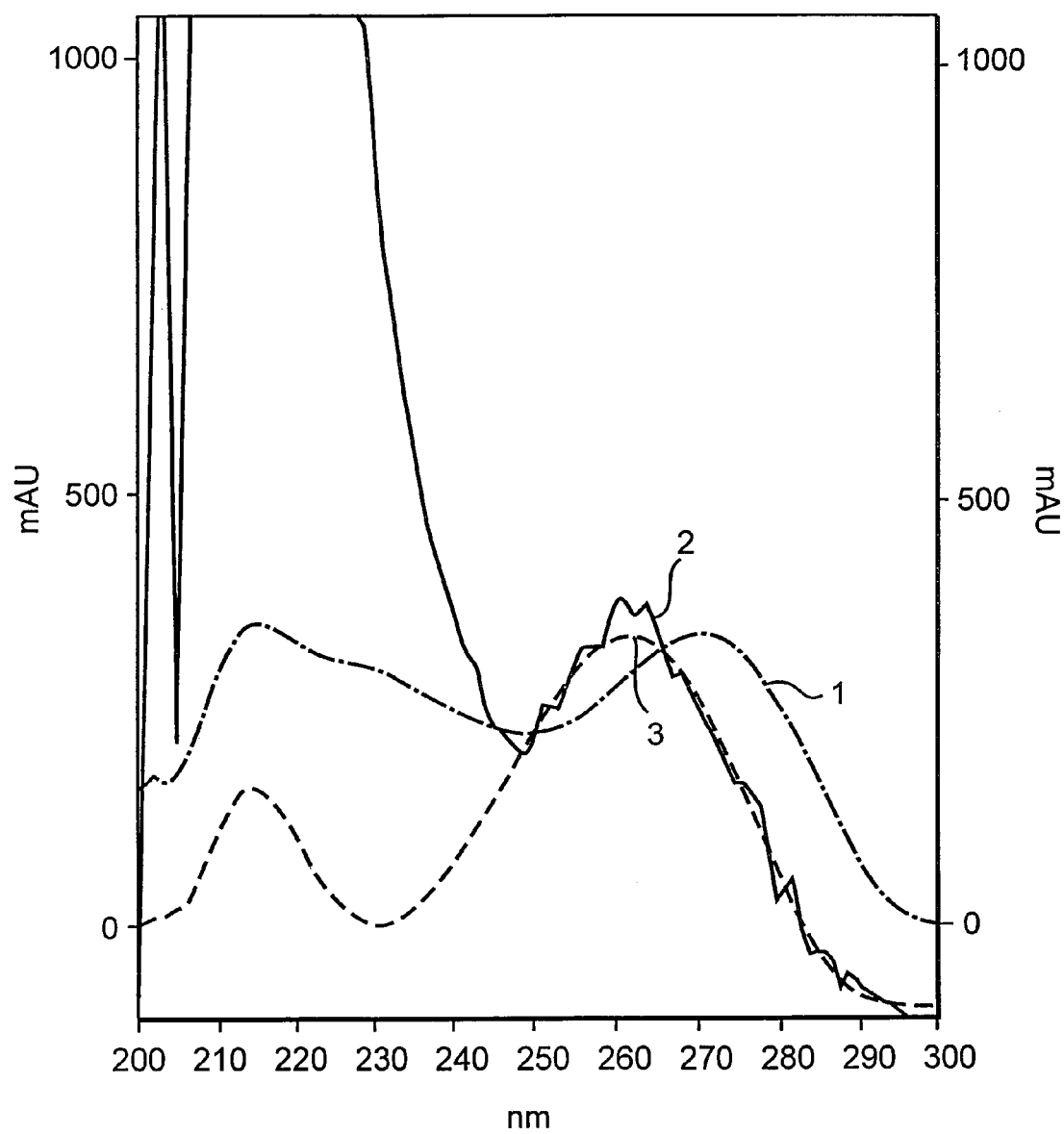
FIG. 19. Comparison of the absorbance spectrum of dCTP, dUTP, and the product generated from heating dCTP. The absorbence spectra (200-300 nm) of the following were superimposed: (1) peak 9.283 from chromatogram A in FIG. 18 (dCTP unheated); (2) peak 12.383 from chromatogram C in FIG. 18 (heated dCTP product); (3) peak 12.100 from chromatogram D in FIG. 18 (dUTP unheated) The three spectra were normalized such that heights of the maximally absorbing peaks (λmax) are equivalent.
Figure 20A:
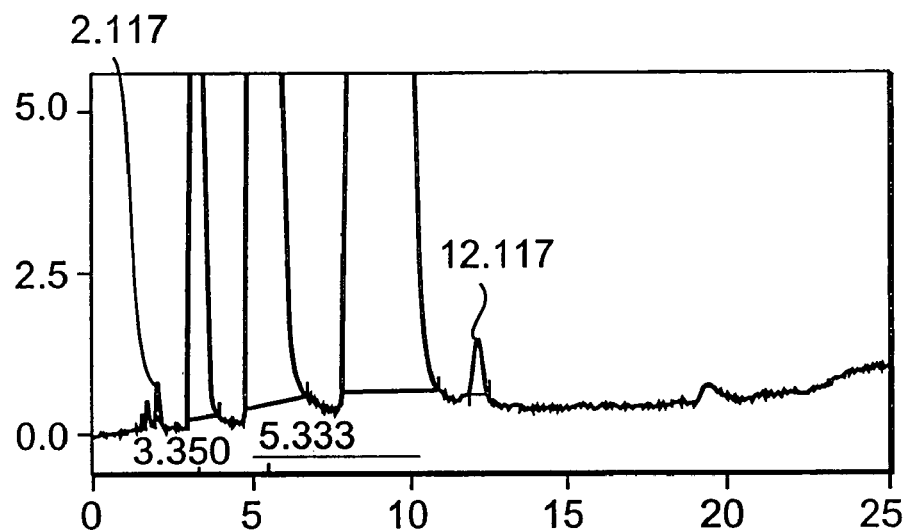
FIG. 20. Reverse phase HPLC analysis of the products generated by PCR cycling dCTP. dCTP (10 mM in cloned Pfu DNA polymerase PCR buffer) was cycled alone (Panel A) or in the presence of 0.5 ng/μl PEF (Panel B) or 1.25U/μl Pfu DNA polymerase (Panel C). Cycling was carried out in a RoboCycler 40 using the following conditions: 95° C. 1 min./30 cycles of: 95° C. 1 min., 60° C. 1 min., 72° C. 10:24 min./72° C. 10 min. 10 μl of the reaction mixtures were chromatographed as described in the FIG. 18 legend. In panel D, the absorbence spectra of dCTP, dUTP, and the product generated from PCR cycling dCTP are compared. The absorbence spectra (200-300 nm) of the following were superimposed: (1) major peak at 8.3-8.8 min. from chromatogram of dCTP+Pfu unheated; (2) peak at 11.867 min. from chromatogram of dUTP in buffer unheated; (3) peak 12.150 from chromatogram C (FIG. 20) showing dCTP+Pfu cycled.
Figure 20B:
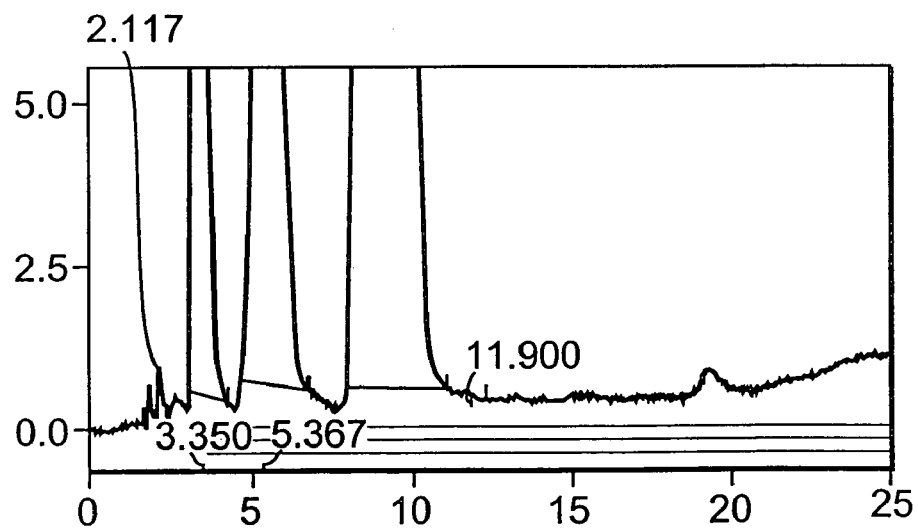
Figure 20C:
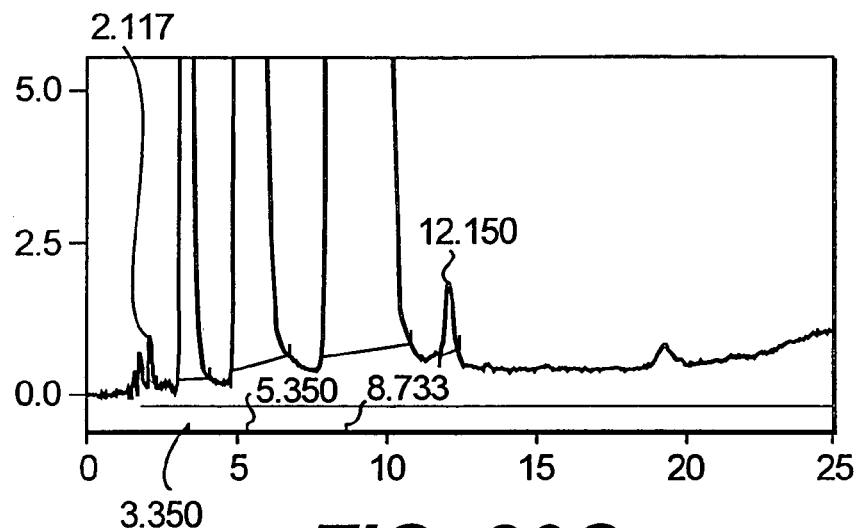
Figure 20D:
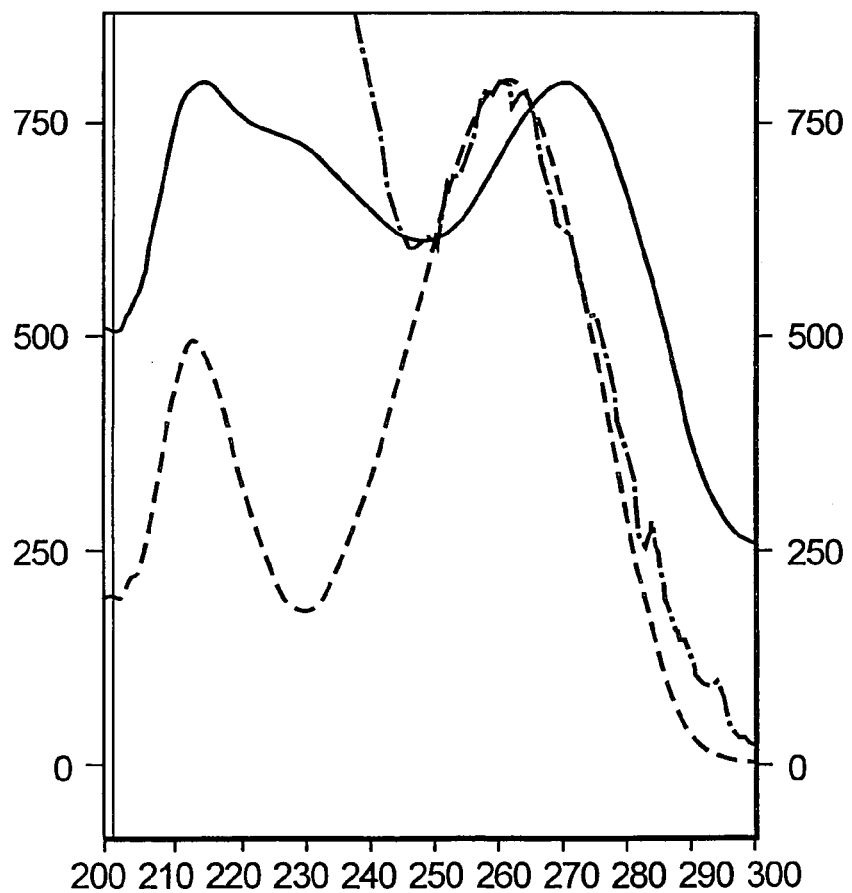

One possible mechanism for the PCR enhancing activity of PEF/P45 is that its associated dUTPase activity may convert any dUTP present during PCR to dUMP, a side-product which should not interfere with DNA polymerase activity. By so doing, dUTP would not be available for incorporation into the PCR product, and hence dU-DNA inhibition of the DNA polymerase would not occur. Such a mechanism is consistent with the increased PCR product yields generated by archeal DNA polymerase in the presence of PEF/P45.

dUTP, however, is not intentionally added to PCR reactions but may be generated by spontaneous deamination of dCTP during the high temperatures used in PCR cycling (Jens-Peter Horst and Hans-Joachim Fritz, (1996) *The EMBO Journal* 15; 5459-5469). To assess the extent of dCTP deamination to dUTP during PCR, we incubated dCTP (10 mM) at 95° C. (PCR denaturation temperature) in the presence of cloned Pfu DNA polymerase PCR buffer. The products of heat treatment were analyzed by reverse phase HPLC (as described above) and peak assignments were made by comparing retention times to those of standards. FIG. 18 shows the results obtained when dCTP is heated for 1 hour (panel B) or 4 hours (panel C) at 95° C. dCTP breaks down into 2 predominate species, dCDP (22%/1 hr; 41%/4 hr.) and dCMP (2.8%/1 hr.; 25%/4 hr.). A minor peak at 12.38 minutes was also produced (0.049%/1 hr.; 0.116%/4 hr.), which was identified as dUTP, based upon its retention time (dUTP standard=12.10 minutes; panel D) and absorbance maximum. As shown in FIG. 19, the 12.38 minute peak generated by heating dCTP (spectrum 2) exhibits maximal absorbence at approximately 260 nm, as does the dUTP standard (spectrum 3), while dCTP absorbs maximally at approximately 270 nm (spectrum 1).

dUTP production was also measured during PCR cycling. A dCTP solution (10 mM dCTP in cloned Pfu DNA polymerase PCR buffer) was subject to PCR cycling in a RoboCycler 40 using the cycling conditions described for the 5.2 kb "on/off" system (example 1). Products generated during PCR were analyzed by HPLC as described above. After 30 cycles, the following products were evident: 79% dCTP, 19% dCDP, 1.8% dCMP, and 0.064% dUTP (FIG. 20, panel A). The dUTP generated during PCR cycling of dCTP exhibited a retention time (12.1 min.) and absorbance maxima (263 nm) which were very close to those of the dUTP standard (11.9 min.; 263 nm) (FIG. 20, panel D). When dCTP was cycled in the presence of Pfu DNA polymerase (50×PCR conditions, 10 mM dCTP and 1.25U Pfu/μl reaction mix) there was no difference in the amount of dCDP, dCMP, or dUTP produced (FIG. 20, panel C). However, when dCTP was cycled in the presence of PEF (50×PCR conditions, 10 mM dCTP and 0.5 ng PEF/μl reaction mix), the following products were produced: 73% dCTP, 19% dCDP, and 8% dCMP (FIG. 20, panel B). There was no detectable dUTP generated when dCTP was cycled in the presence of PEF, consistent with an associated dUTPase activity of PEF.

The increase in dCMP production in dCTP+PEF samples (8%) as compared to dCTP±Pfu samples (1.7-1.8%) shows that in addition to eliminating the minor dUTP deamination product during PCR, PEF will also convert dCTP to dCMP. In this experiment (50×PCR conditions), the final dCTP concentration post-PCR was 73% in PEF-containing reactions and 79% in those lacking PEF. This slight drop in the dCTP pool is not anticipated to affect PCR product yield or DNA polymerase replication fidelity significantly. However, it is anticipated that the use of higher amounts of PEF in PCR (>>1 ng per 100 μl reaction) will be deleterious due to dCTP reactivity. If high amounts of PEF are used, it is possible that the dCTP pool could fall below levels required for maximal yields and lowest misinsertion rates. As described elsewhere, we have observed inhibition of replication or amplification and/or smearing of products with the use of excessive amounts of PEF.

5. PEF Reverses Inhibitory Action of dUTP in Amplification Reactions

Although Lasken reported that the incorporation of dUTP in the nascent DNA strand only inhibited archeal polymerases by 40% (Lasken, et al. (1996) J. Biol. Chem. 271; 17692-17696), we unexpectedly found that the presence or addition of small amounts of dUTP into PCR reactions had more dramatic inhibitory consequences, as demonstrated below.

A relatively small (0.9 kb) fragment of the human α1-antitrypsin gene was amplified in the absence or presence of dUTP. PCR reaction mixtures contained the following (in a 100 μl volume): 1× Cloned Pfu polymerase buffer; 200 μM each, dCTP, dGTP, dATP; 200 ng oligo F91-23 (100 ng/μl); 200 ng oligo R980-23 (100 ng/μl); 125 ng Human genomic DNA; 2.5 units Pfu DNA polymerase; 200 μM total of (dTTP and dUTP) or (dTTP+PEF generated dUMP).

```
F91-23
5' GAGGAGAGCAGGAAAGGTGGAAC 3'      (SEQ ID NO: 84)

R980-23
5' CTCCATGTCCCAACTCCGATCAC 3'      (SEQ ID NO: 85)
```

PEF generated dUMP was prepared as described in Example 11, section 1, and purified by reverse phase HPLC.

PCR cycling was carried out as follows: 95° C. for 1 minute (1 cycle); 95° C. for 1 minute—58° C. for 1 minute—72° C. for 2 minutes (30 cycles).

Figure 21:
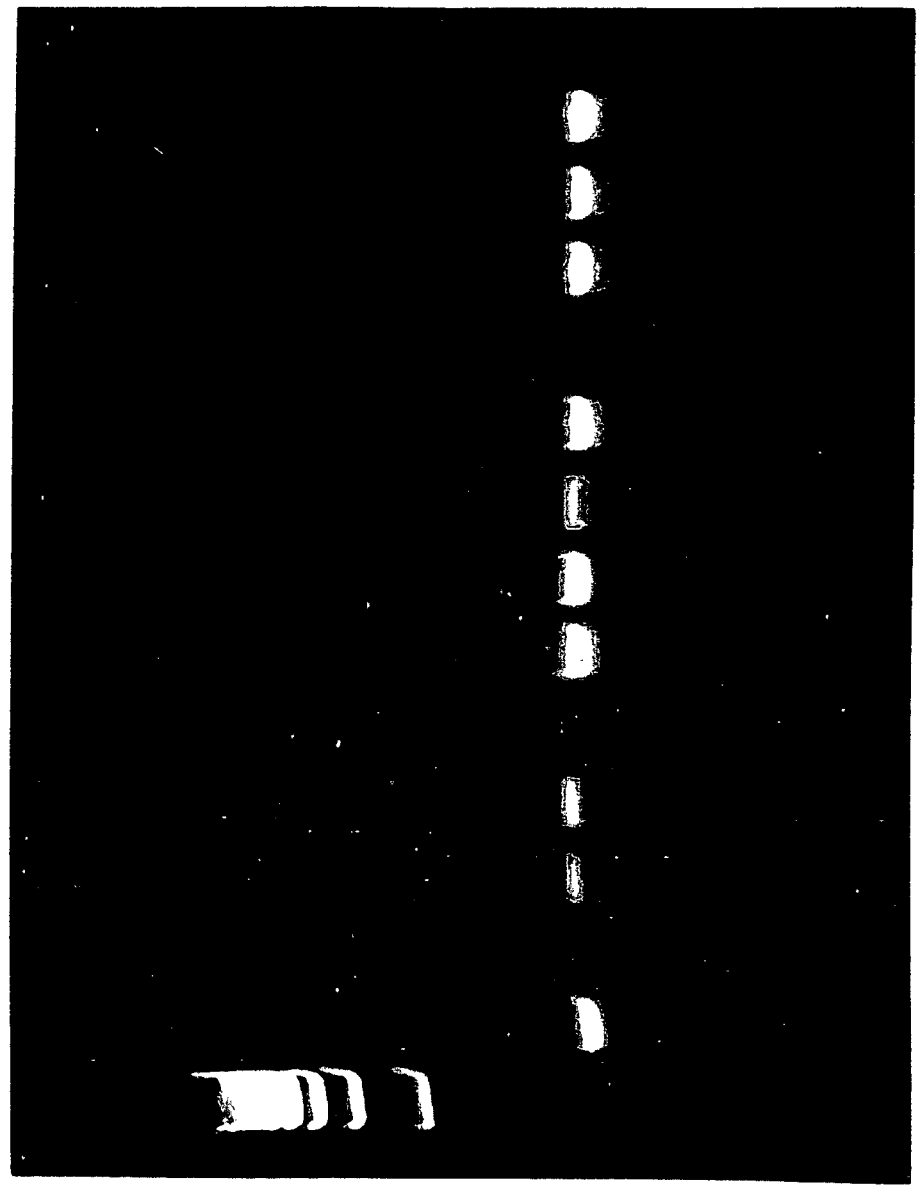
FIG. 21. dUTP Inhibition and Reversible Inhibition with PEF and rP45. The following components were added to cloned Pfu DNA Polymerase PCR reactions (5.2 kb "on/off" assay of example 1): Lane 1, 2 μM dUTP+7 ng native PEF. Lane 2, 2 μM dUTP. Lane 3, 2 μM PEF generated dUMP. Lane 4, 20 μM PEF generated dUMP. Lane 5, 2 μM dUTP+ 180 ng rP45 clone 1. Lane 6, 2 μM dUTP+20 ng rP45 clone 1. Lane 7, 2 μM dUTP+2 ng rP45 clone 1. Lane 8, 2 μM dUTP+ 180 ng rP45 clone 23. Lane 9, 2 μM dUTP+20 ng rP45 clone 23. Lane 10, 0.2 μM dUTP. Lane 11, 0.2 μM dUTP+7 ng native PEF. Lane 12, 0.2 μM dUTP+20 ng rP45 clone 1. Lane 13, 0.2 μM dUTP+20 ng rP45 clone 23. In the right Lane M, 1 Kb DNA markers were run.

The PCR products were examined on a 1% agarose, 1×TBE gel as shown in FIG. 21. The amplification of the 900 bp product from human genomic DNA was completely inhibited with dUTP concentrations as low as 2 μM (1% of the dTTP+dUTP pool) and partially inhibited at 0.2 μM (0.1%). The concentration of individual nucleotides in a standard PCR reaction is about 200 μM. dUTP inhibition can be completely prevented when PEF or the recombinant P45 protein (rP45) is added to PCR reactions containing dUTP. Seven ng of PEF can reverse the inhibition caused by as much as 20 μM dUTP (data not shown). The preferred amount of PEF or P45 used in a particular reaction can be optimized according to the principles provided here or by methods for quantifying amplification reactions known in the art.

Unlike dUTP, the PEF generated byproduct, dUMP, was not inhibitory in Pfu polymerase-based PCR reactions, even when present at concentrations of 20 μM. In FIG. 21, amplifications containing purified dUMP appear less robust than other bands on the gel. It should be noted that the other PCR products on this gel were generated by Pfu in the presence of PEF or rP45, which has been demonstrated to enhance PCR product yields as compared to amplifications conducted in the absence of PEF/rP45. These results are consistent with the enhancing activity of PEF and rP45 being a result of dUTPase activity. The dUTPase activity may hydrolyze dUTP and thereby prevent the incorporation of dUTP into DNA. As demonstrated in FIG. 21, dUTP incorporation by Pfu DNA polymerase during PCR can significantly decrease PCR product yields. Accordingly, the invention comprises a method of enhancing nucleic acid replication or amplification reactions by reducing the dUTP concentration or preventing the incorporation of dUTP into replicated or amplified products, as well as compositions that are capable of preventing that incorporation.

We also tested whether PEF/rP45 could reverse the inhibition caused by uracil-containing DNA. PCR amplification was carried out in the presence of a third unrelated primer, which contains 9 dUs instead of dTs (dU oligo). Primers complementary to M13 DNA were synthesized.

```
Control Oligo                              (SEQ ID NO: 86)
5'GGTTTTCCCAGTCACGACGTTGTAAAACGACGGCCAGT 3' dU Oligo                                   (SEQ ID NO: 87)
5'GGUUUUCCCAGUCACGACGUUGUAAAACGACGGCCAGU 3'
```

Figure 22:
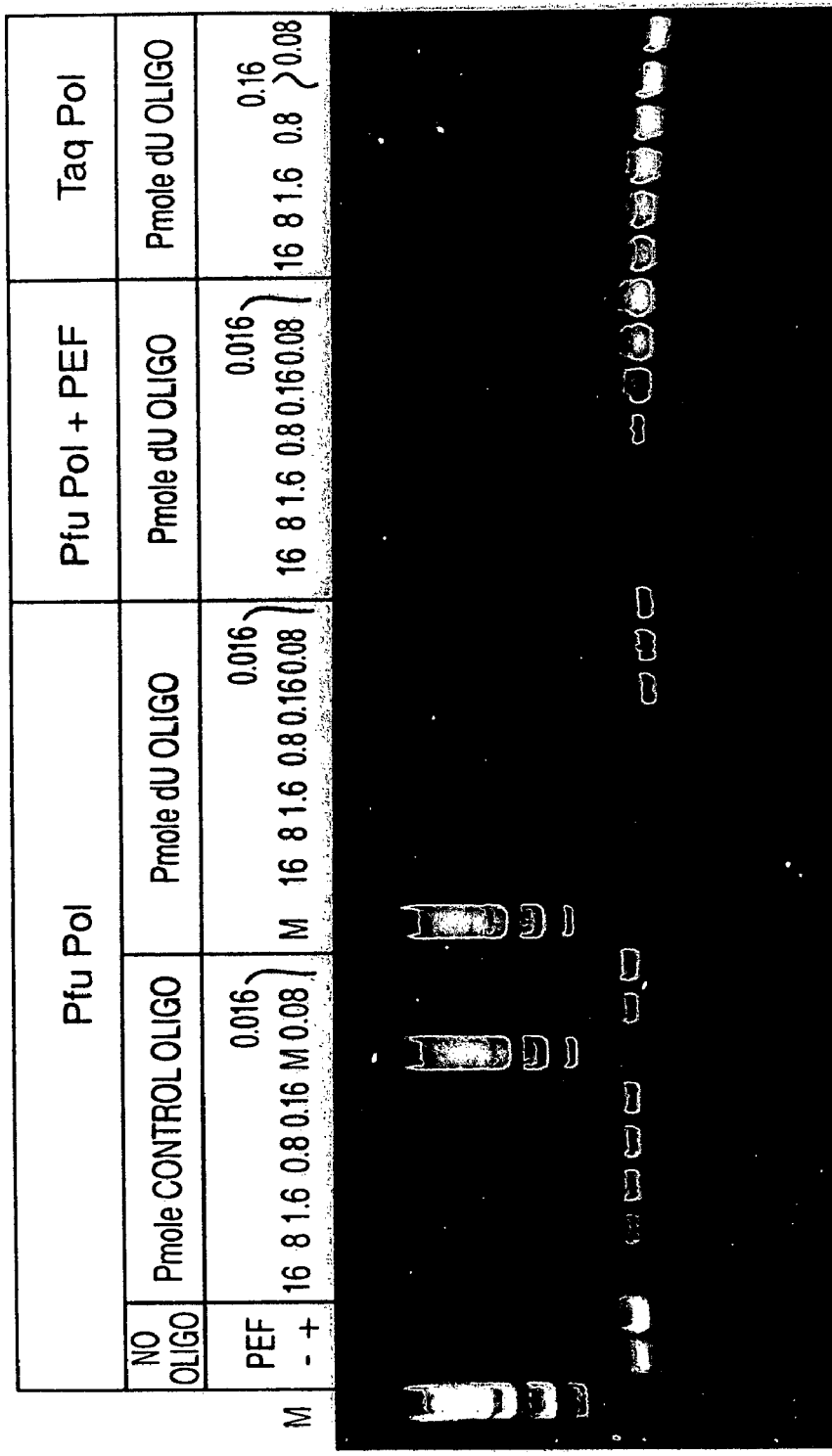
FIG. 22. Inhibition of PCR with unrelated dU Containing Oligonucleotides. A 0.9 kb target was amplified from human genomic DNA. Lanes 2 and 3 represent the PCR amplification without the addition of a third oligo. The sample in lane 3 was amplified in the presence of 7 ng of PEF. Lanes 4-8 and 10-11 represent the titration of the control (dT rather than dU) oligonucleotide (40mer). Lanes 13 through 32 represent samples amplified in the presence of the dU oligonucleotide (40mer). Lanes 13-19 were amplified with Pfu DNA polymerase alone. Lanes 14 through 26 were amplified with Pfu DNA polymerase in the presence of 7 ng of PEF. Lanes 27 through 32 were amplified with Taq DNA polymerase.

The 900 bp α1-antitrypsin fragment was amplified in the presence of the oligos, added at levels ranging from 200 ng (16 pmole) to 0.2 ng (0.016 pmole) per 100 ul reaction. In addition, similar reactions were performed with Taq DNA polymerase instead of Pfu DNA polymerase. In FIG. 22, the control oligonucleotide shows inhibition of the Pfu-based PCR reaction at high concentrations (16 and 8 pmole). In contrast, inhibition by the dU oligo was readily observed at concentrations as low as 0.8 pmole. It seems likely that both oligonucleotides sequester Pfu DNA polymerase away from the PCR primers and genomic DNA, but the dU oligo can inhibit at lower concentrations. These results show that Pfu DNA polymerase may be more tightly bound to a dU containing substrate. With the addition of PEF, a small amount of amplification product is observed in reactions containing 0.8 pmole of dU containing primer.

The enhancement by PEF in the dU oligo-inhibited reaction could be achieved through at least two possible pathways. The most likely explanation is that PEF is having no effect on the dU containing oligonucleotides and is simply increasing the activity of Pfu DNA polymerase by scavenging dUTP generated during PCR by heat- or chemically-induced deamination of dCTP (eg., lanes 2 and 3 of FIG. 22). Or, PEF may work with Pfu DNA polymerase to remove the uracil moieties from the oligonucleotides through a repair pathway. Thus, PEF may also be used in repair reactions employing appropriate polymerase activities. Repair reactions are known in the art and methods to adopt the use of PEF into those reactions can be devised by those skilled in the art.

The knowledge of potential PEF mechanisms of action described here allows those skilled in the art to employ other dUTP modifying enzymes in enhancing polymerase reactions. A definition or one of these other modifying enzymes can be an enzyme that diminishes the capacity to incorporate dUTP by polymerases or at least partially inhibits dUTP incorporation. Assays used to identify and characterize PEF as described herein can also show other dUTP modifying enzymes. These other modifying enzymes could also mimic the enhancing attributes of PEF or a particular protein, such as P45 or rP45. An example of this class of enzyme would be dUTP pyrophosphatases (EC 3.6.1.23), such as deoxyuridine 5'-triphosphate nucleotide hydrolase, as well as other enzymes involved in dUTP metabolism, catabolism, or synthesis. These other enzymes may be used alone or in combination with PEF or other proteins or enhancing additives.

Furthermore, the presence of the consensus uridine-binding motif or the related sequences shown herein can also be used to define an enzyme or protein that is a PEF. Thus, a protein the comprises SEQ ID NO.: 72, or any one of SEQ ID NOs.: 72-81, or combinations of these sequences, may be a PEF according to this invention.

EXAMPLE 12

Identification of Other Proteins for Enhancing Polymerase Activity

The structural information, in the amino acid and nucleotide sequences, as well as the functional information described here allow one skilled in the art to identify polymerase enhancing and/or dUTPase activities from a variety of sources. For example, we have shown above how degenerate probes made from the amino acid sequences of P50 and P45 can be used to clone nucleotide sequences encoding polymerase enhancing and dUTPase activities, or PEF. Since we have identified the importance of dUTPase activity in controlling and enhancing polymerase reactions, such as PCR, structural information available for any dUTPase can be put to a new and advantageous use in identifying and producing proteins for enhancing polymerization reactions. Furthermore, the assays described can be used to identify the presence of dUTPase activity from any source.

1. Cloning Human dUTPase as a Representative Eukaryotic Protein for Enhancing Polymerization Reactions To determine if other enzymes with dUTPase activity could also produce polymerase enhancing activity, we cloned a representative eukaryotic protein, human dUTPase. Total RNA was isolated from human placenta and converted to cDNA as follows: 5 µl total human RNA, 5 µl oligo dT (0.1 µg/µl), 1 µl Moloney murine leukemia virus reverse transcriptase (40 u/µl), 1 µl 100 mM dNTPs, 5 µl 10× first strand buffer, 33 µl DEPC-treated water (where 1× first strand buffer is 50 mM Tris-HCL (pH 8.3), 75 mM KCl, 10 mM DTT, and 3 mM MgCl$_2$). The reaction was incubated at 37° C. for one hour. A negative control was run in parallel without reverse transcriptase.

Primers containing a sequence specific to the 5' and 3' termini of one of the human dUTPase genes were synthesized and are shown below. The accession numbers for the cDNA sequence of Human deoxyuridine triphosphatase (DUT) and gi|1421817|gb|U62891|HSU62891. These primers also shared sequence with the vector pCAL-n-EK (in bold print below), which allowed ligation independent cloning (LIC) of the amplified product, as described in Example 10.

```
                                           (SEQ ID NO.: 88)
Primer 285    GACGACGACAAGATGCCCTGCTCTGAAGAGACACC (SEQ ID NO.: 89)
Primer 286    GGAACAAGACCCGTTTAATTCTTTCCAGTGGAACC
```

Prior to PCR, the reverse transcriptase was heat inactivated by incubating the reaction at 80° C. for 5 minutes. The dUTPase sequence was amplified in a 100 µl reaction containing 1× cloned Pfu polymerase buffer, 200 ng of each primer, 200 µM dNTPs, 2.5 units of Pfu DNA polymerase, 3 ng of PEF complex and 3 µl of human placenta cDNA from the previous section.

The reactions were amplified under the following conditions: 95° C. for 3 minutes (1 cycle); 95° C. for 1 minute—50° C. for 1 minute—72° C. for 2 minutes (30 cycles). The amplified reaction was examined on a 1% agarose gel to confirm that the product exhibited the correct size before purification. The purified product was cloned into the expression vector pCAL-n-EK, as described in Example 10, and transformed into XL1-Blue cells. Three clones were confirmed to contain human dUTPase by sequencing of the first 500 bases. After the transformants were shown to contain the dUTPase sequence by PCR amplification, their plasmids were harvested and used to transform the E. coli strain BL21 (DE3).

2. Human dUTPase Expression and Activity Analysis

The BL21/dUTPase clones were induced with IPTG and the expressed protein was purified by means of the calmodulin binding peptide (CBP) tag expressed as a fusion protein at the amino terminus of the dUTPase sequence. The fusion protein was purified on calmodulin agarose, as described in example 10. The protein products were analyzed by SDS-PAGE and found to be of the correct molecular weight.

To confirm that the dUTPase clones were active, the Sigma pyrophosphatate assay (see Example 11) was utilized. The assay demonstrated that all of the clones tested could convert dUTP to dUMP+pyrophosphate. The human dUTPase enzyme was thermolabile and became completely inactive after a one minute pre-incubation at 70° C.

Polymerase enhancement was also detected with the 5.2 kb on/off assay. The assay was modified from the protocol described in Example 1 to allow detection of the thermolabile PEF activity. A PCR cocktail was mixed to provide an identical starting point for all samples. Ninety-nine microliters of the cocktail was aliquoted into six thin-walled, 0.5 ml tubes. The reactions contained 278 ng of human genomic DNA, 200 ng of each primer (see Example 1), 200 µM each dNTP, 2.5 units of Pfu DNA polymerase in 1× cloned Pfu polymerase buffer. At each 60° C. annealing step, 0.5 µl of one the following were added: human dUTPase preparation, a 1/10th dilution of the human dUTPase preparation, 2 ng/µl rP45 (positive control), or dUTPase storage buffer (negative control). Both human dUTPase reactions were run in duplicate. The samples were cycled as follows: 95° C. for 1 minute (1 cycle); 95° C. for 1 minute—60° C. for 1 minute—72° C. for 5.2 minutes (30 cycles).

10 µl of each PCR reaction was visualized on a 1% agarose, 1×TBE gel by ethidium bromide staining. (See FIG. 23). The undiluted human dUTPase preparation was able to enhance the polymerase activity to produce the 5.2 Kb band. As demonstrated by the negative control, lack of any enhancing factor results in a failed PCR. The positive control for this experiment, rP45, did not work in this experiment, presumably because an excessive quantity (30 ng total) was added.

EXAMPLE 13

Production of Antibodies to PEF and Western Blot Analysis

1. Production of anti-PEF and anti-rP45 IgG

Figure 24:
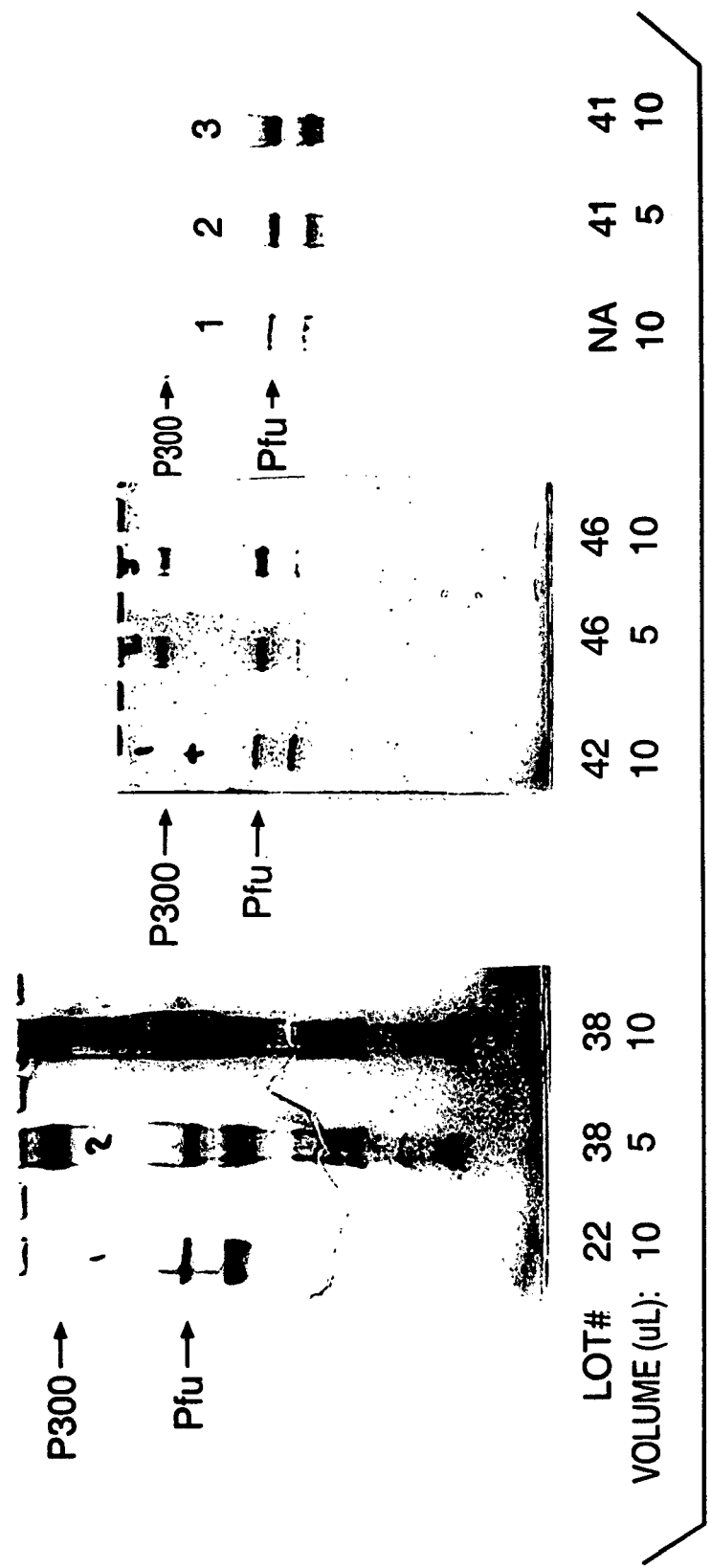
FIG. 24. Presence of PEF(P300) in *P. furiosus* DNA polymerase preparations. SDS-PAGE analysis is shown for six preparations of native Pfu DNA polymerase with varying levels of PEF present. The volumes of each lot loaded is indicated (µl). The protein samples were not boiled prior to electrophoresis and the gels were silver-stained.

PEF-specific IgG was purified by immunoaffinity chromatography from the sera of rabbits previously immunized against a lot of native Pfu DNA polymerase containing PEF (see FIG. 24 showing gel of purified native Pfu polymerase preps). The S-200-purified Pfu PEF was covalently coupled to AffiGel 10 (BioRad: Hercules, Calif.) in the presence of 20 mM HEPES, 1 mM DTT, 50 mM KCl, 0.05% Tween 20, 1 mM EDTA, and 10% glycerol, following the manufacturer's recommended protocol. Rabbit sera (2.4 ml) was loaded onto a 0.2 ml column in the presence of 10 mM Tris (pH 7.5). The column was washed extensively and the specific IgG was eluded with 0.1M glycine-HCl (pH 2.5) followed by 0.1M triethylamine (pH 11.5). Using a Centricon-30, the IgG was concentrated and the elution buffer replaced with PBS.

In addition, sera containing rP45-specific IgG was obtained by immunizing rabbits with recombinant P45, which was prepared as a tagged fusion protein, as described in example 10, section 2. The purified enzyme (0.177 mg/ml) was used to immunize two New Zealand white rabbits using the following immunization schedule: 90 µg/rabbit in Complete Freund's Adjuvant (CFA); 18 days later, boost with 45 µg/rabbit in incomplete Freund's adjuvant (IFA); 39 days later, second boost; 45 days later, obtained serum sample for Western blot.

2. Western Blot Analysis Using Anti-PEF Antibodies

Cell extracts were prepared by suspending cells in 4×50 mM Tris, pH 8.2, 10 mM BME, 1 mM EDTA, and 10% glycerol, followed by sonication. Then, 2.5 mM PMSF was added and the cellular debris removed by centrifugation for 15 minutes at 14,000 rpm. PEI was added to the supernatant to a final concentration of 0.9% and the mixture centrifuged again. The supernatants (10 µl) were electrophoresed on 4-20% SDS-PAGE gels and the proteins transferred to nitrocellulose by electroblotting. The blots were blocked with 1% Blotto/PBS for 1 hour at room temperature and then incubated with PEF-specific IgG overnight at 4° C. The blots were washed in PBS-0.05% Tween 20, and then incubated with alkaline phosphatase-conjugated goat anti-rabbit IgG. The blot was washed and then incubated in color development solution (100 mM Tris-HCl, pH 9.5, 100 mM NaCl, 5 mM $MgCl_2$, 0.3 mg/ml NBT, and 0.15 mg/ml BCIP) for approximately 1-2 minutes. The enzyme reaction was stopped and the membrane was washed five times with deionized water.

Figure 25:
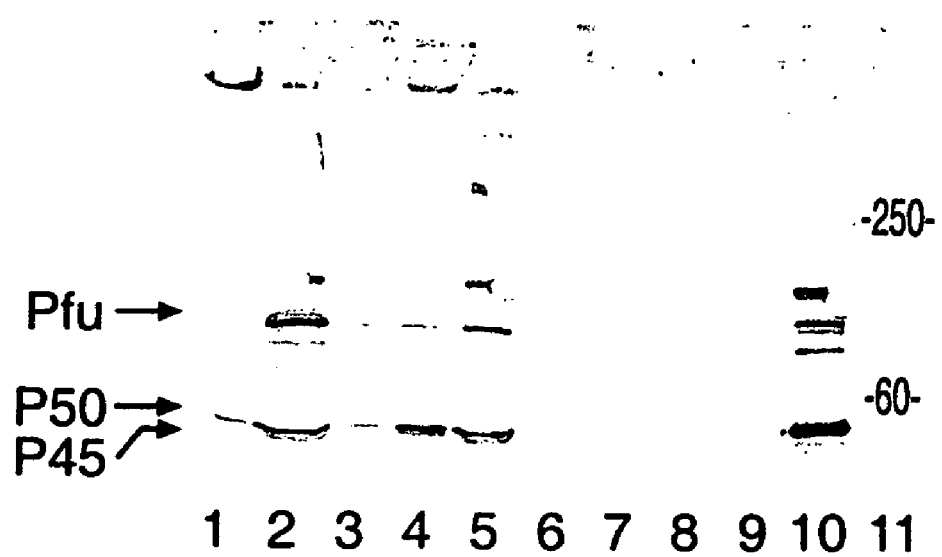
FIG. 25. Western blot analysis of crude extracts using *P. furiosus* PEF-specific IgG. Extracts were prepared from 5 different fermentations of *P. furiosus* (lanes 1-5), 3 partially purified fractions from *T. aquaticus* (lanes 6-8), and 1 extract from *E. coli* (lane 9). Purified PEF (550 ng) and pre-stained molecular weight markers were run in lanes 10 and 11, respectively. With the exception of the markers, all samples were boiled in SDS/BME dye prior to loading.

FIG. 25 depicts the results of the Western Blot. Extracts were prepared from 5 different fermentations of P. furiosus (lanes 1-5). In addition, three extracts or partially purified column fractions from T. aquaticus (lanes 6-8) and one extract from E. coli (lane 9) were also run. Purified PEF (550 ng) and pre-stained molecular weight markers were run in lanes 10 and 11, respectively. With the exception of the markers, all samples were boiled in SDS/BME dye prior to loading. The results show PEF-specific IgG binds to and cross-reacts with components of the PEF complex in crude Pfu extracts, including the P50 and P45 components. In contrast, no cross-reaction was observed with extracts from T. aquaticus or E. coli.

3. Western Blot Detection of Native PEF and Recombinant P45 Using Anti-rP45 Sera Native PEF samples were electrophoresed on a 4-20% gradient Tris-Glycine SDS gel. The samples were loaded without denaturation (P300 form) or after partial (boiling in 2% SDS; P45 form) or complete (boiling 2% SDS plus 1% TCA) denaturation. The samples were transferred to nitrocellulose and the blots developed as described above, except that sera from rabbits immunized with recombinant P45 was used (diluted 1:000).

Figure 26:
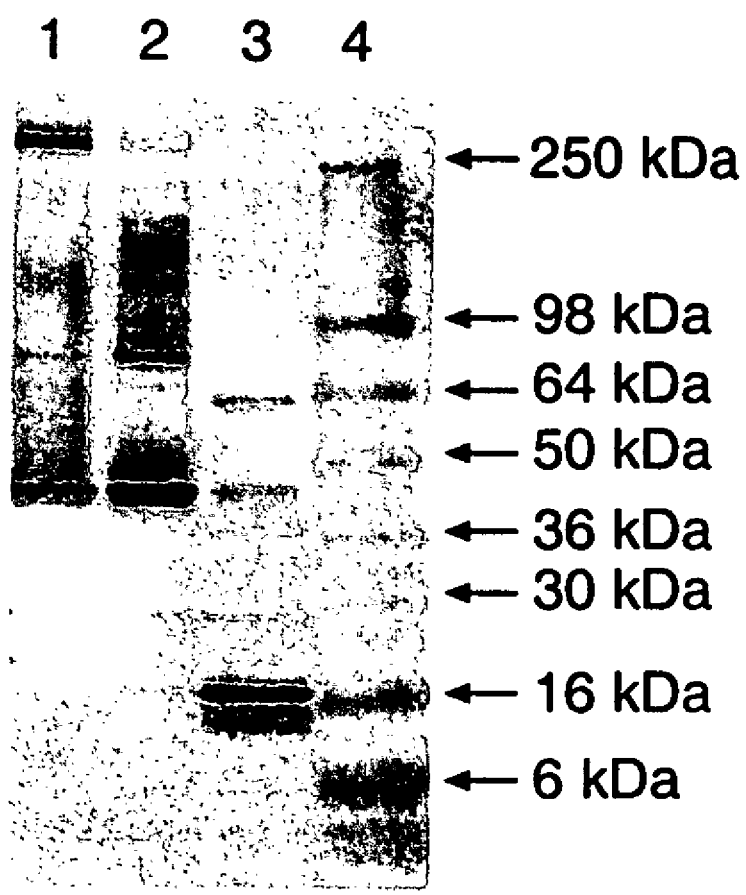
FIG. 26. Western blot analysis of native PEF samples using anti-recombinant P45 antibody. Three samples (700 ng each) of native Pfu PEF were prepared as follows: unheated/2% SDS loading dye (lane 1); heated/2% SDS loading dye (lane 2); and heated/1% TCA/2% SDS loading dye (lane 3). Heating was carried out for 5 minutes at 95° C. The samples were electrophoresed on a 4-20% gradient gel and transferred to nitrocellulose. The blot was probed as described in the text with rabbit anti-rP45 sera. Novex prestained molecular markers (SeeBlue™) were run adjacent to the PEF samples in lane 4.

In FIG. 26, antibodies specific to recombinant P45 cross-react with bands in undenatured, partially denatured, and fully denatured samples of native PEF. The predominant bands are the P300 aggregate (P45/P50) present in the unheated lane, the 45 kD (partially denatured) form present in the boiled/SDS sample, and the 17 kD (fully denatured) form present in the boiled/1% TCA/2% SDS lane, which presumably represents the fully denatured monomer. In addition to these different aggregation states of native P45, there are also minor bands present in the Western blot, which may represent additional forms of P45 or the cross-reaction of antibodies to *Pyrocossus* proteins sharing common epitopes with *E. coli* contaminants present in the recombinant P45 preps.

Figure 27:
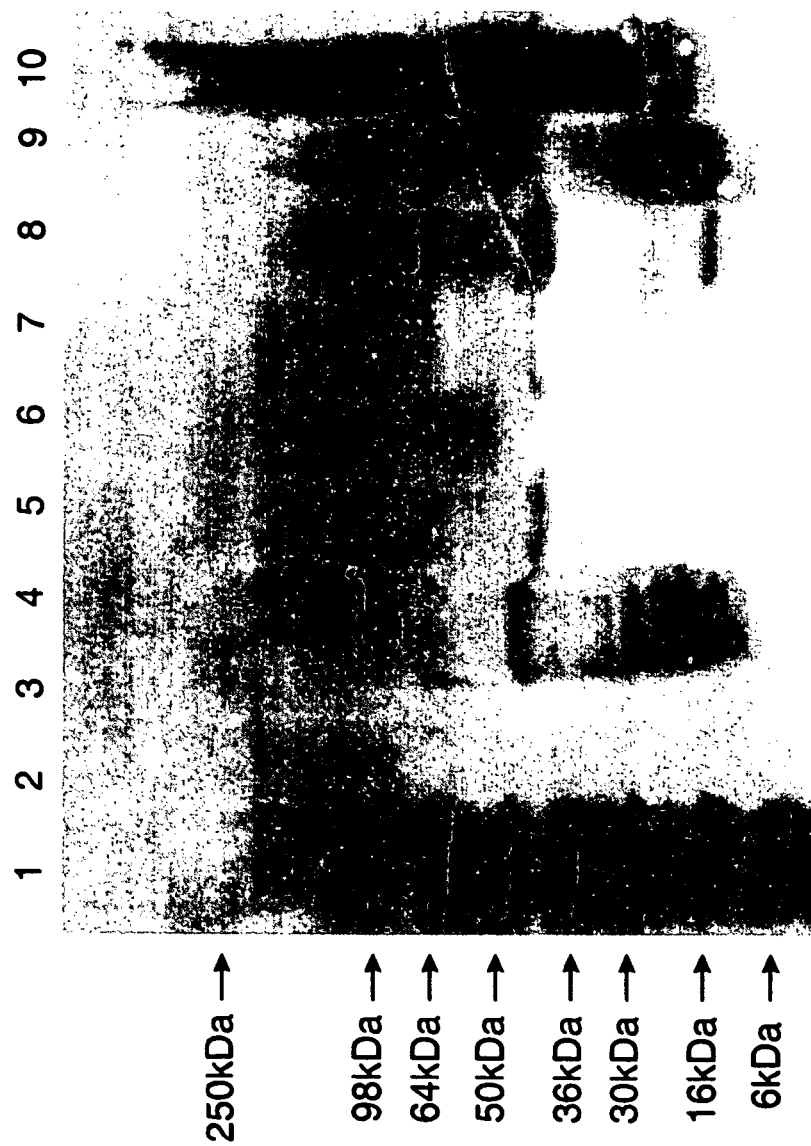
FIG. 27. Western blot using the antibody to CBP-rP45 and cell lysates from different species. The lysates shown in lanes 2-7 were prepared by sonication. The samples were heated at 95° C. prior to loading except for the sample loaded in lane 10 which was left at room temperature. Lane 1, SeeBlue™ Markers (Novex), Lane 2, Uncharacterized *Bacillus* species (Magenta), lane 3, *Thermus aquaticus,* lane 4, uncharacterized species, Lane 5, *Pyrococcus furiosus,* Lane 6, *Methanobacterium thermoautotrophicum,* lane 7, Human lymphoma HL60 cells, Lane 8 purified *Pyrococcus furious* PEF, Lane 9 purified fusion CBP-rP45. Lane 10 purified fusion CBP-rP45.

As with the PEF-specific IgG from above, anti-rP45 sera can also be used to identify immunochemically-related proteins from other species. In FIG. 27, the rP45-specific IgG was used to probe a blot containing cellular extracts from bacteria (*Bacillus* species, *T. aquaticus*), archea (*P. furiosus, M. thermoautotrophicum,* and an uncharacterized species) and human cells (HL60 lymphoma). The results obtained show the antibodies bind to proteins from *P. furiosus*, the uncharacterized species, and the human cell line, which migrate with the same apparent molecular weight as purified native PEF. The antibodies also bind weakly with proteins in the *Bacillus* and *M. thermoautotropicum* extracts, although these bands migrate with a different apparent molecular weight than *P. furiosus* PEF species. As with the PEF-specific IgG, no cross-reactivity was detected with *T. aquaticus* extracts.

In a separate Western assay, samples from *Thermus thermophilis* were run out on an SDS-PAGE gel and probed with the rP45 antisera. The rP45 antibody binds to a band of approximately 24 kD (between markers of 16 kD and 30 kD) and another band approximately twice that size, presumable a dimeric or multimeric form. This demonstrates that PEF activity or protein is present in the *T. thermophilis* samples. The PEF as dUTPase activity in these samples was further confirmed by a dUTP conversion assay employing reverse phase HPLC. The assay detected the turn-over of dUTP with the *T. thermophilis* samples, but a control sample showed no detectable turn-over of the dUTP present.

EXAMPLE 14

Use of PEF Complex in Nucleic Acid Replication Reactions

Initially and as a control to confirm the activity of the DNA polymerase used, gapped-duplex calf thymus DNA (Pharmacia) assays were performed. The polymerase cocktail contained 50 mM Tris-HCl, pH 8.0, 5 mM $MgCl_2$, 1 mM DTT, 50 µg/ml BSA, 4% glycerol, 200 µM each dNTP, [$^3$H]TTP (0.5 mCi/µmole final concentration), and 250 µg/ml of activated calf thymus DNA (Pharmacia). Samples containing Pfu DNA polymerase or *P. furiosus* PEF were serially diluted in Pfu DNA polymerase storage buffer (50 mM Tris-HCl, pH 8.2, 0.1% NP-40, 0.1% Tween-20, 0.1 mM EDTA, 1 mM DTT, 50% glycerol) and then 1 µl of each dilution was added to 10 µl aliquots of polymerase cocktail. Polymerization reactions were conducted in triplicate of 30 minutes at 72° C. The extension reactions were quenched on ice, and then 5 µl aliquots were spotted immediately onto DE81 filters (Whatman). Unincorporated [$^3$H]TTP was removed by 6 washes with 2×SCC (0.3M NaCl, 30 mM sodium citrate, pH 7.0), followed by one wash with 100% ethanol. Incorporated radioactivity was measured by scintillation counting. The assay was calibrated by counting a known amount of [$^3$H] TTP on DE-81 filters, omitting the wash steps. One unit of polymerase activity is defined as the amount of enzyme which catalyzes the incorporation of 10 nmoles of total dNTP into polymeric form (binds to DE-81 paper) in 30 minutes at 72° C. Polymerase concentrations (U/ml) were extrapolated from the slope of the linear portion of units vs. enzyme volume plots.

The PEF samples tested exhibit no significant DNA polymerase activity while the Pfu DNA polymerase exhibited a specific activity of $2\text{-}4\times10^4$ u/mg. enhancing activity assay.

2. Screening Assays for PCR-Enhancing Activity Using Pfu-derived Samples

A number of amplification assays can be designed to detect the presence or absence of PEF activity, and/or compare PEF activity between samples. Generally, these tests employ a sample containing a rare sequence to be amplified. The sequence is so rare, or the conditions so designed, that amplification under normal situations results in barely detectable or no detectable amplified product. By adding a sample with putative PEF activity, any effects on the amount of amplified product formed can be detected.

One particular screening assay is called the "On/Off" assay, which detects the presence or absence of PEF. The "On/Off" assay results in appreciable amplified product only when PEF activity is present, or a detectable difference in amplified product when PEF activity is present compared to when PEF is not present. Methods for detecting the amount of amplified product are known in the art and include those using electrophoresis and hybridization.

One embodiment of an assay used to screen for PEFs, in this case from *Pyrococcus furiosus*, involved amplifying a 6.2 kb target from transgenic mouse DNA (6.2 kb primer-template assay). A master PCR cocktail was prepared consisting of: 200 µM each dNTP, 2 µg/ml primer F432-21 (5'-CTA-TTG-AGT-ACG-AAC-GCC-ATC) (SEQ ID NO.: 62), 2 µg/ml primer R6656-20 (GTC-ACG-CCT-GCT-CCA-CTC-CG) (SEQ ID NO.: 63), 2.5 µg/ml λAA742 DNA (transgenic mouse DNA having 40 copies of a lambda phage DNA shuttle vector), 1× cloned Pfu DNA polymerase PCR buffer (10 mM KCl, 10 mM $(NH_4)_2SO_4$, 20 mM Tris-HCl (pH 8.8), 2 mM $MgSO_4$, 0.1% (v/v) Triton X-100, and 100 µg/ml BSA), and 25U/ml cloned Pfu DNA polymerase. Samples were diluted in 1× cloned Pfu DNA polymerase PCR buffer, and 1 µl of each diluted sample was added to 24 µl of the PCR cocktail. PCR amplifications were conducted on the RoboCycler 96 Temperature Cycler (Stratagene), using the following conditions: 96° C. for 45 s (1 cycle)/96° C. for 45 s; 60° C. for 45 s; 72° C. for 14 min. (35 cycles)/72° C. for 10 min. (1 cycle). PCR products (10 µl/lane) are run out on 1% agarose gels and PCR product bands visualized by ethidium bromide staining. Samples with PCR enhancing activity exhibiting higher yields of the expected 6.2 kg PCR product than can be obtained in the presence of DNA polymerase alone. When PCR enhancement is due to the presence of PEFs, rather than contaminating endogenous DNA polymerase activity, amplifications performed in the absence of exogenous DNA polymerase (e.g. Pfu DNA polymerase) yield no PCR product. Moreover, PCR amplifications performed in the absence of exogenous DNA template should yield no PCR product when the PEF sample lacks contaminating target DNA.

1. Enhancement of Cloned Pfu DNA Polymerase with Pfu PEF

Figure 28:
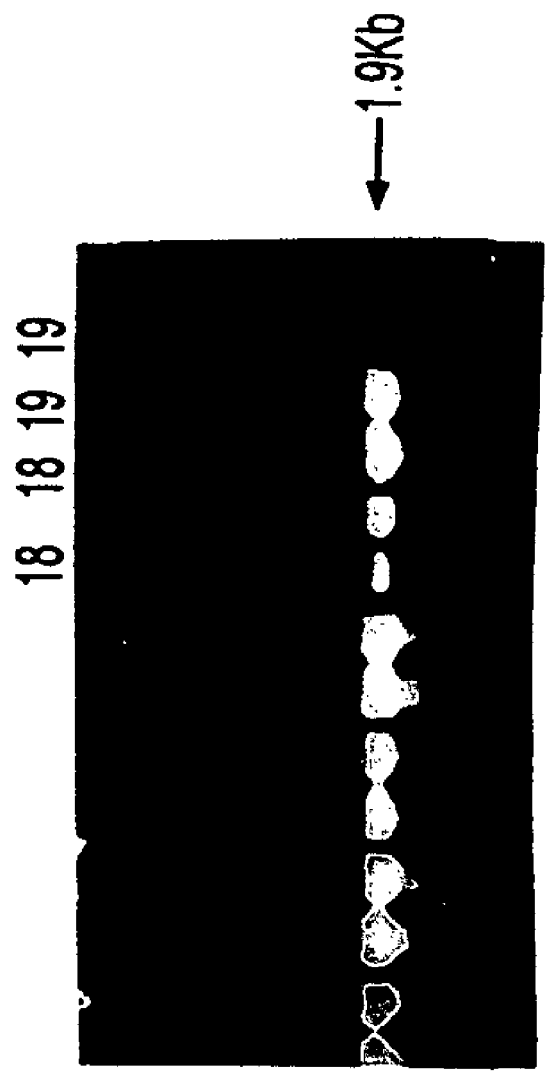
FIGS. 28, 29, and 30. PCR enhancing activity of *P. furiosus* PEF in cloned Pfu DNA polymerase PCRs. PCR amplifications were performed as described in example 14 with the following additional notes.
Figure 29:
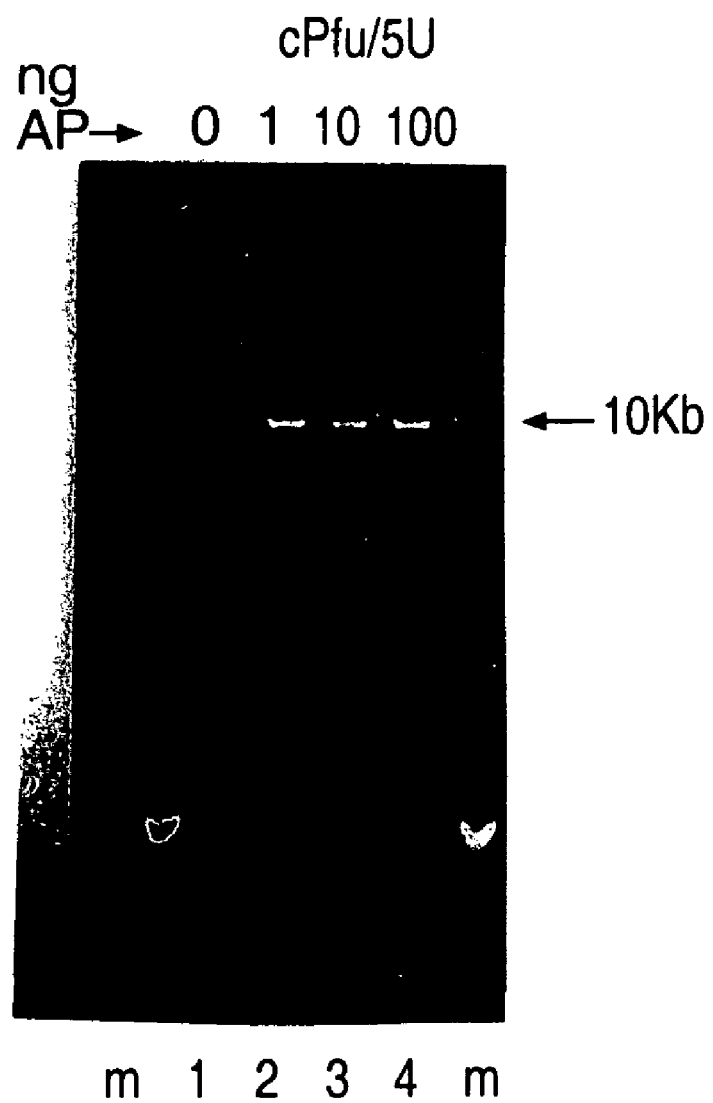
Figure 30:
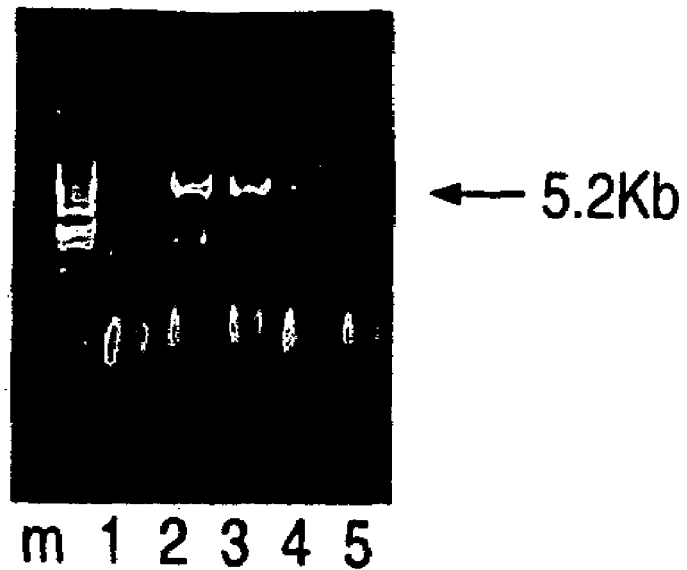

*P. furiosus* PEF has been demonstrated to enhance the yield of PCR products generated with recombinant Pfu DNA polymerase using plasmid, lambda, and genomic DNA templates (FIGS. 28-30). The results demonstrate that the addition of *P. furiosus* PEF increases PCR product yield for a variety of PCR systems, ranging in target complexity. Relatively easy targets, e.g. plasmid DNA, can be successfully amplified with Pfu DNA polymerase, and the addition of PEF further increases product yield (FIG. 28). We have found that fewer PCR cycles or lower template concentrations can be used in PEF-containing reactions, demonstrating the advantageous properties of the proteins and compositions described and the methods employing them.

The most dramatic enhancements were observed when long (FIG. 29) and/or highly complex targets (FIG. 30) are amplified. The presence of PEF unexpectedly and significantly improves the amplification of these targets, which are often poorly amplified by single enzyme PCR reactions. In FIG. 29, the addition of 1-100 ng of PEF (S200-purified PEF; prep. 3) to 100 µl PCR reactions containing 5U of Pfu DNA polymerase significantly increased yeilds of a 10 kb PCR product. In FIG. 30, a 5.2 kb target was successfully amplified from human genomic DNA in the presence of 0.3-280 ng PEF (SCS #52 S200 purified) per 100 µl PCR, but not in the absence of PEF, despite the use of 1.9 min. per kb extension times.

Figure 31:
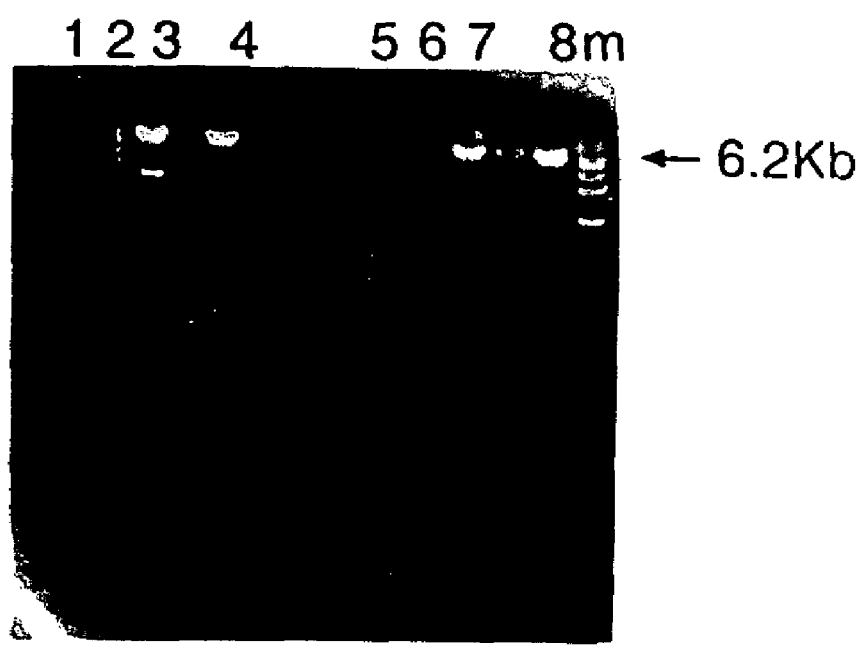
FIG. 31. Effect of Stratagene's Perfect Match (*E. coli* ssb) on the specificity of PCRs conducted with cloned Pfu DNA polymerase and *P. furiosus* PEF. PCRs were conducted using the 6.2 kb test system (example 1) in 100 µl reaction volumes. 1 µl of the following were added to PCRs: lanes 1,5-dilution buffer; lanes 2,6-undiluted PEF-containing heparin sepharose fraction (microcon 30-concentrated SCS #36 H.S. #78, prep. 2; ≈40 ng/µl PEF); lanes 3,7-PEF fraction diluted 1:10; lanes 4,8-PEF fraction diluted 1:100. 1 µl of Perfect Match was added to PCRs run in lanes 5-8. No DNA samples were loaded in the lanes between lanes 3 and 4, 4 and 5, and 7 and 8.

*P. furiosus* PEF has been found to enhance the yields of both specific and non-specific PCR products, when amplifications are conducted under less stringent PCR conditions with PCR primers that hybridize to more than one target. *E. coli* ssb (single-stranded binding protein; Stratagene's PerfectMatch) has been shown previously to increase the specificity of primer extension reactions, presumably by minimizing the formation of poorly matched primer-template complexes. When used in conjunction with *E. coli* ssb, *P. furiosus* PEF has been found to enhance the yield of specific PCR products (FIG. 31). Pfu PEF also enhances yields of PCR products obtained with exo-Pfu and a mixtures of Taq and Pfu polymerase (for example, TaqPlus Long™, Stratagene; La Jolla, Calif.). Therefore, Pfu PEF is useful with polymerase mutants, truncated versions of polymerases, mixtures of polymerases, and polymerase-additive combinations (for example, Perfect Match®, Stratagene).

2. Enhancement of Native Pfu DNA Polymerase with Pfu PEF

Figures 32A, 32B:
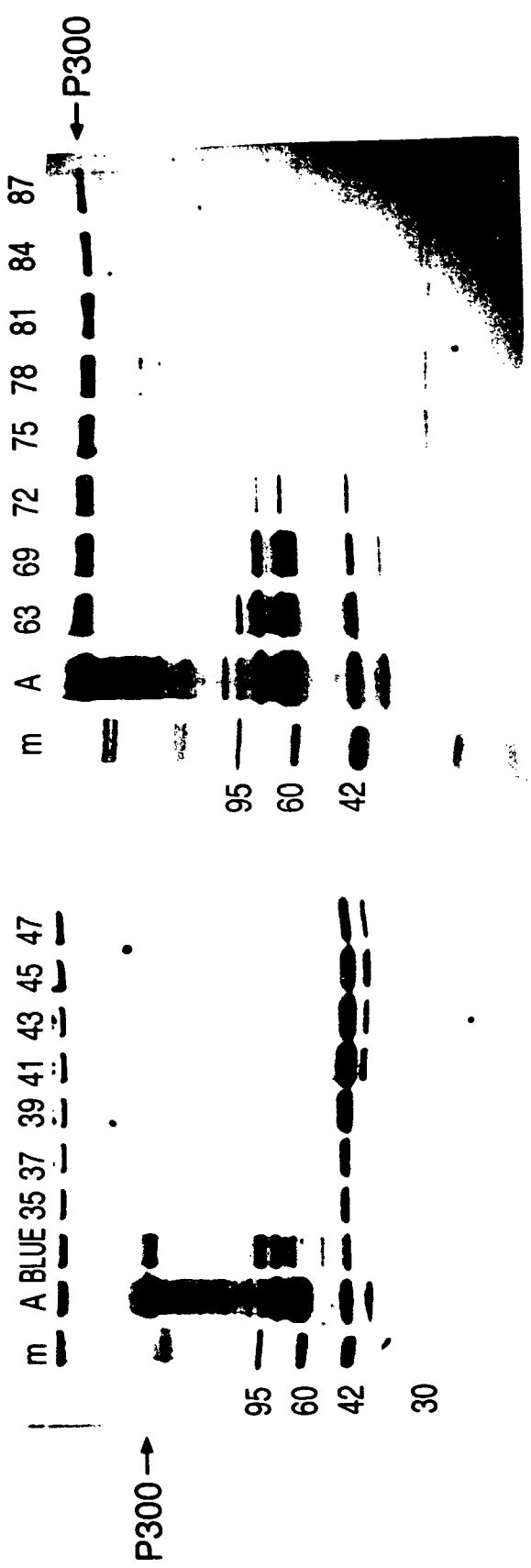
FIG. 32. SDS-PAGE analysis of heparin sepharose (H.S.) column fractions. The heparin sepharose fractions indicated (# at top) from SCS native Pfu DNA polymerase prep. #37 (SCS #37) were analyzed on 4-20% SDS-PAGE gels (4 µl/lane). Prestained molecular weight markers were run in lanes denoted "m" and 4 µl of SCS #36 H.S. #78 (PEF prep. 2) was run in lanes marked "A". The peak of DNA polymerase (95 kD) activity eluted between fractions 50 and 61.

Subsequent to identifying PEF from *P. furiosus*, we recognized that certain lots of native Pfu DNA polymerase preparations contained PEF. Varying amounts of the >250 kD aggregate could be detected on silver-stained SDS-PAGE gels (e.g., lots 38 and 46 in FIG. 24). Eleven of the 23 preparations examined were found to visibly contain low levels (8/11 lots; 0.1-1% total protein) to high levels (3/11 lots; 10-30% total protein) of PEF. PEF co-migrates with Pfu DNA polymerase during the initial Q- and SP-Sepharose columns in Pfu DNA polymerase purification, and elutes just after the major peak of Pfu DNA polymerase activity on the Heparin Sepharose column (FIG. 32). Pfu DNA polymerase fractions pooled after the Heparin Sepharose step are typically contaminated with varying amounts of PEF, depending upon the column efficiency and pooling strategy employed.

Contamination of native Pfu DNA polymerase with varying amounts of PEF could potentially contribute to lot-to-lot variation in the performance of native Pfu DNA polymerase in PCR. It is expected that lots containing approximately 1-100 ng of PEF per 2.5U of Pfu DNA polymerase will give rise to higher PCR product yields than amplifications conducted with cloned Pfu DNA polymerase or native Pfu DNA polymerase lots contaminated with ≦10 pg per 2.5U Pfu DNA polymerase (<0.02% total protein). In theory, a lot containing certain PEF concentrations would exhibit reduced Pfu DNA polymerase performance, based upon the apparent inhibition of PEF at high concentrations discussed below (>900 ng per 2.5U Pfu DNA polymerase in 100 µl PCRs).

When adding PEF to native Pfu DNA polymerase PCR amplifications, it is anticipated that the level of PEF contained in a particular lot of native Pfu must be taken into account to avoid smearing, inhibition of synthesis, or sub-optimal enhancement.

EXAMPLE 15

Use of PEFs in Amplification Reactions

1. Activity of Pfu PEF in a Standard PCR Protocol

To enhance PCR product yield, *P. furiosus* PEF is added, separately or pre-mixed with the DNA polymerase, to standard PCR amplifications. PCR amplification reactions generally consist of the following: 0.01-0.05U/µl DNA polymerase, 2.5 pg/µl to 1 ng/µl *P. furiosus* PEF, 1-5 ng/µl of each primer, 0.5-10 ng/µl of genomic DNA template, and 0.2 mM each dNTP in a suitable buffer (e.g., cloned Pfu DNA polymerase buffer consists of 10 mM KCl, 10 mM $(NH_4)_2SO_4$, 20 mM Tris-HCl (pH 8.8), 2 mM $MgSO_4$, 0.1% (v/v) Triton X-100, and 100 ng/µl BSA). Amplifications from less-complex templates (e.g., lambda or plasmid DNA) are typically successful with 0.1-100 pg/µl DNA. The minimum amounts of native PEF typically used in PCR correspond to amounts of enzyme sufficient to catalyze the release of 0.1 to 0.4 nmole PPi/hr per 100 µl PCR reaction (see example 11, section 2). PCR amplifications are conducted under standard conditions; e.g., 94-96° C. for 0.5-2 min. (1 cycle)/94-96° C. for 0.5-2 min.; 50-65° C. for 0.5-2 min.; 68-72° C. for 0.5-3 min. per kb of target amplified (30-40 cycles)/72° C. for 0-10 min. (1 cycle).

2. Enhancement of PCR Amplification Reactions Employing DNA Polymerases Other than Pfu DNA Polymerases

*P. furiosus* PEF has been found to enhance the performance of other α-type (Family B-related) DNA polymerases from thermophilic archea. Enhanced PCR product yields were observed when *P. furiosus* PEF was added to amplifications conducted with DNA polymerases from both *Pyrococcus* and *Thermococcus* species. DNA polymerases demonstrated to function with *P. furiosus* PEF include: Pwo DNA polymerase (Boehringer Mannheim; cloned from *P. woesei*), Deep Vent DNA polymerase (New England Biolabs; cloned from *P. sp.* GBD), JDF3 DNA polymerase (Stratagene; cloned from *P. sp.* JDF3), ES4 DNA polymerase (Stratagene; purified from *P. sp.* ES4, renamed *P. endeavon*) and Vent DNA polymerase (New England Biolabs; cloned from *T. litoralis*).

Figure 33:
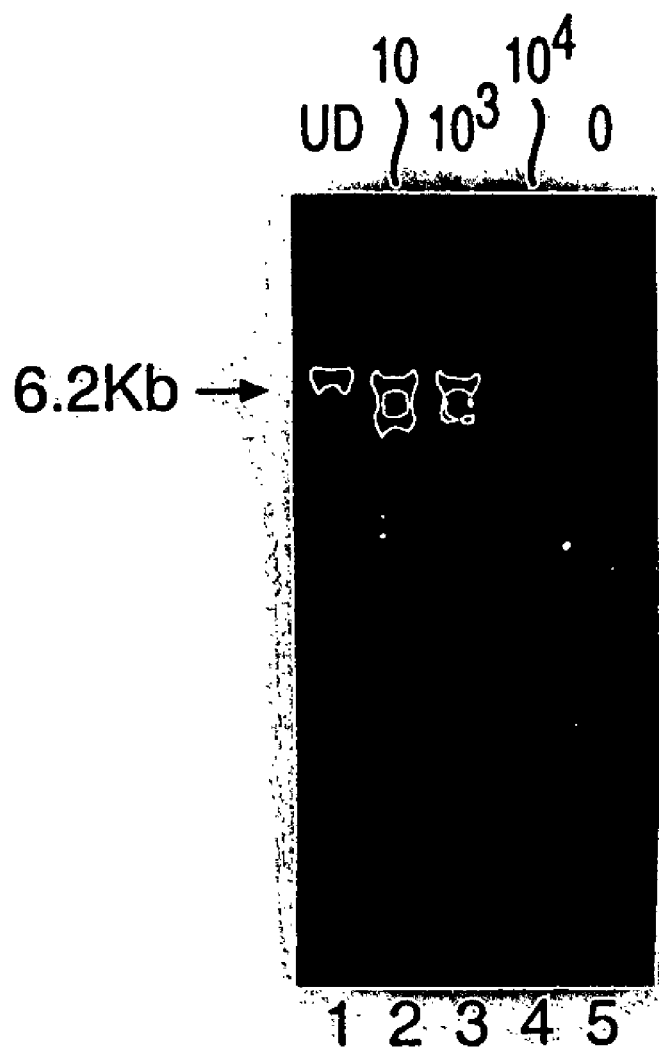
FIGS. 33, 34, 35, and 36. Enhancing activity of *P. furiosus* PEF in PCRs conducted with Pwo (FIG. 33), JDF-3 (FIGS. 34 and 35), ES4 and Vent (FIG. 35), and Deep Vent (FIG. 36) DNA polymerases.
Figure 34:
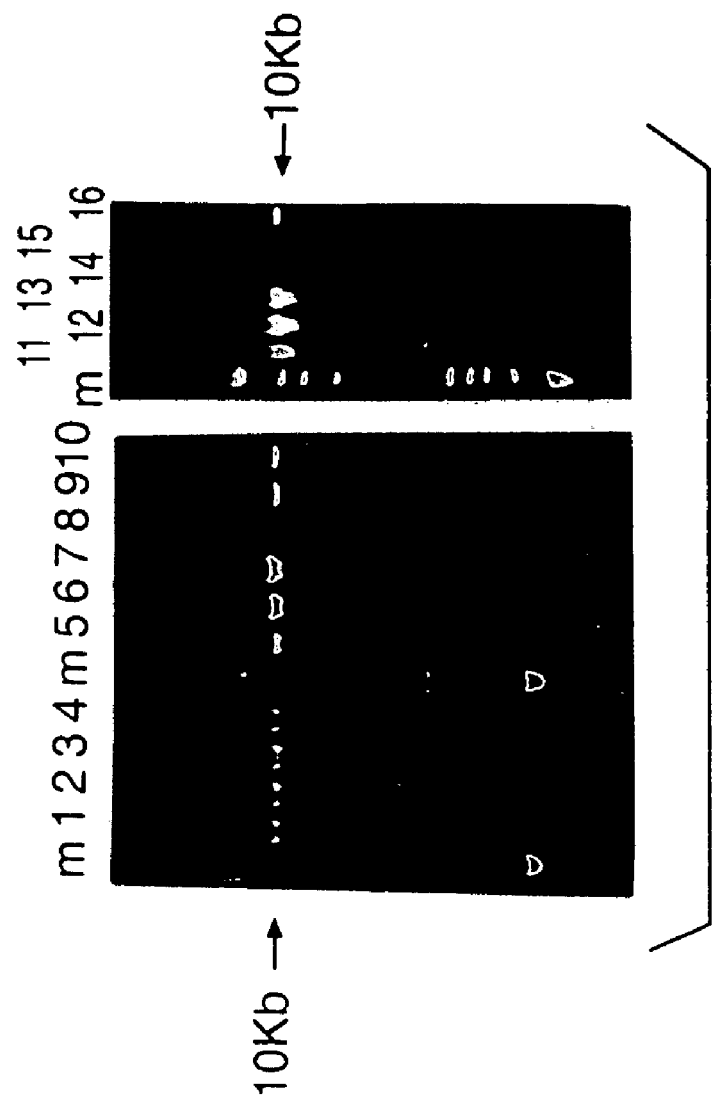
Figure 35:
Figure 36:
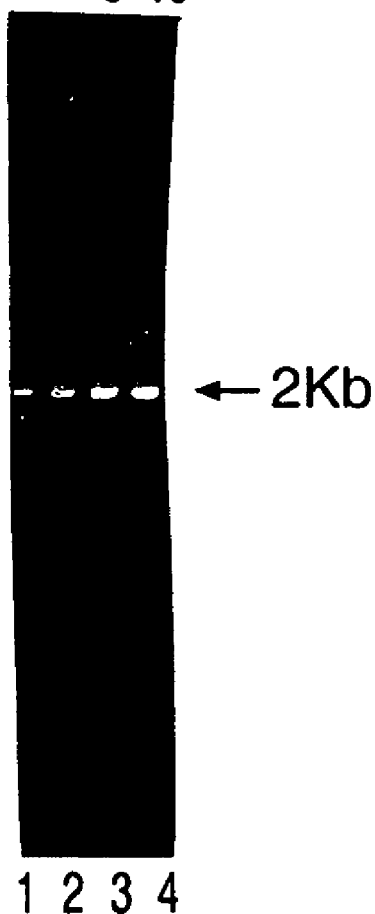

In FIG. 33, S200-purified Pfu PEF (prep. 1) increased yields of a 6.2 kb PCR product obtained with 2.5U of Pwo DNA polymerase. In FIG. 34, the addition of S200-purified PEF (prep. 3) to JDF3 DNA polymerase PCRs increased the yield of a 10 kb product amplified from lambda DNA (lanes 5-7; 11-13) and mouse genomic DNA containing 40 copies (lanes 8-10) or 1 copy (lanes 14-16) of a lambda DNA transgene. In JDF3 DNA polymerase-based PCRs, amplifications are typically conducted with 1U of enzyme and extension times of 0.5 min./kb target. In FIG. 35, the addition of 5 ng of S200-purified PEF (prep. 3) to ES4, JDF3, Pfu, and Vent DNA polymerase PCRs increased the yield of a 1.9 kb product amplified from *P. furiosus* genomic DNA. In FIG. 36, the addition of *P. furiosus* PEF was also shown to increase yields of a 2 kb PCR product amplified with Deep Vent DNA polymerase from transgenic mouse genomic DNA.

Figure 23:
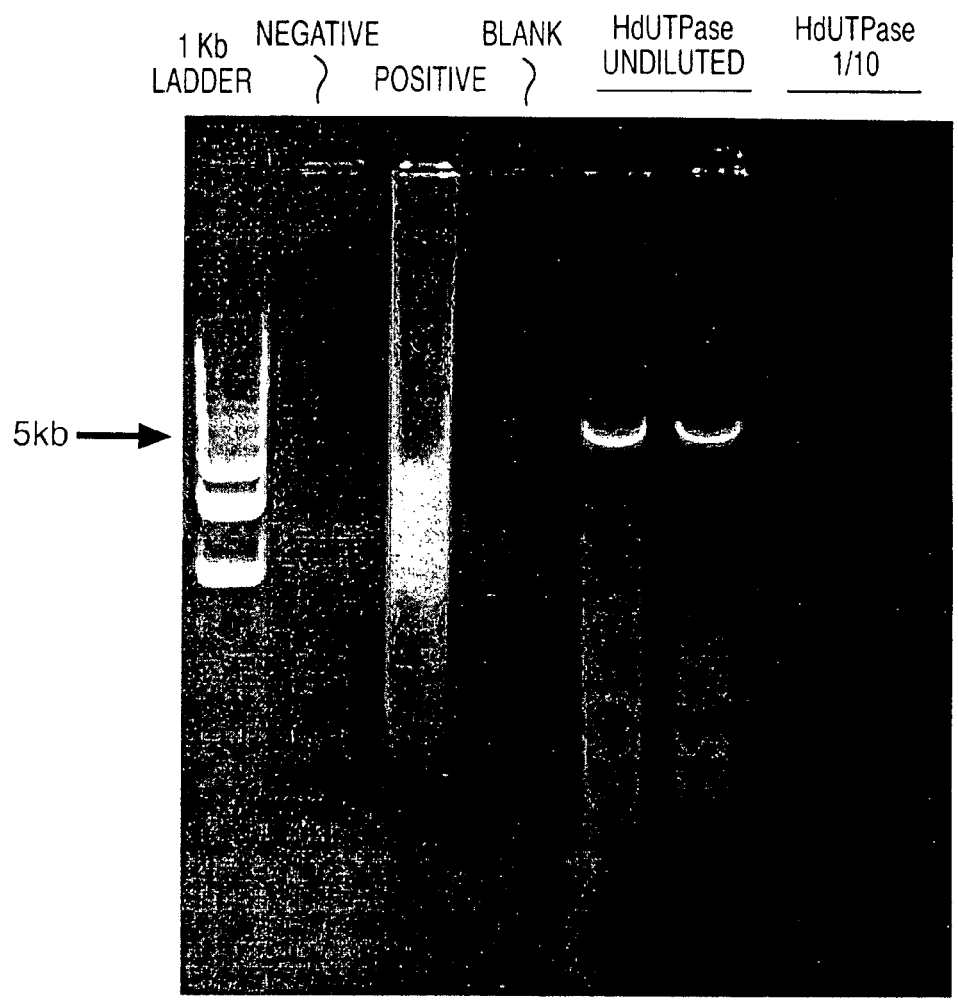
FIG. 23. Human dUTPase mimics PEF/P45 activity. PEF activity was measured using the 5.2 kb primer-template assay described in example 1. At each annealing step of the PCR reaction, 0.5 µl of the following were added: dUTPase storage buffer (negative control), recombinant P45 (at 2 ng/µl) (positive control), human dUTPase preparation undiluted (duplicate reactions), or diluted 1:10 (duplicate reaactions).

The addition of *P. furiosus* PEF may not enhance the yield of PCR products generated with Taq DNA polymerase (FIG. 34, lanes 1-4 and FIG. 23, lanes 9-10). Taq DNA polymerase is a Pol I-like (Family A-related) DNA polymerase isolated originally from the thermophilic eubacteria *Thermus aquaticus*.

3. Enhancement of RT-PCR Reactions

*P. furiosus* PEF has also been shown to enhance the yield of PCR products amplified from reverse transcribed RNA (cDNA) in a process known as RT-PCR, known in the art. Enhancement has been observed in both 2-step (FIG. 37) and 1-tube RT-PCR protocols (data not shown). In the former procedure, aliquots of cDNA synthesis reactions are added to PCR reactions containing a thermostable DNA polymerase (e.g., Pfu DNA polymerase) and *P. furiosus* PEF. In the latter approach, RNA is added to reaction mixtures containing a thermolabile RT, dNTPs, primers, a thermostable DNA polymerase (Pfu DNA polymerase), and *P. furiosus* PEF. cDNA synthesis and PCR amplification take place sequentially, in the same tube, by conducting cDNA synthesis at 37-42° C., followed by PCR amplification at elevated temperatures.

In the 2-step RT-PCR procedure, cDNA synthesis is first performed by combining the following reagents (50 µl final volume): 5 µg total RNA pre-annealed to 300 ng of primer (oligo dT, random hexamers, or a gene-specific primer), 4 mM each dNTP, 20U RNase block (optional), and 50U MMLV RT (or other RT) in buffer containing 50 mM Tris-HCl (pH 8.3), 75 mM KCl, 3 mM $MgCl_2$, and DEPC-treated water. cDNA synthesis is allowed to proceed for 1 hour at 37-42° C. After heat inactivation of the RT, 1 µl of cDNA is added to a 50 µl PCR reaction containing 5U Pfu DNA polymerase, 0.01-50 ng *P. furiosus* PEF, 1 µM of each primer, and 0.2 mM each dNTP in buffer consisting of 10 mM KCl, 10 mM $(NH_4)_2SO_4$, 20 mM Tris-HCl (pH 8.8), 3 mM $MgSO_4$, 0.1% (v/v) Triton X-100, and 100 µg/ml BSA. PCR can be conducted using the following cycle conditions: 94° C. 2 min.; 60° C. 2 min.; 68° C. 1 min. per kb (1 cycle) and then 94° C. 1 min.; 60° C. 1 min.; 68° C. 1 min. per kb (40 cycles).

The enhancement of RT-PCR with *P. furiosus* PEF was evaluated using PCR primers designed to span at least one intron-exon junction in the EGF receptor gene. Two primer sets were used (antisense: 5'GAG-TTA-AAT-GCC-TAC-ACT-GTA-TCT (SEQ ID NO.: 29); sense: 5'CAG-GAC-TCA-GAA-GCT-GCT-ATC-GAA (SEQ ID NO.: 30) (1 kb) or 5'CTG-CAC-GTG-CCC-TGT-AGG-ATT-TGT (SEQ ID NO.: 31) (3 kb)), which generate PCR products of 1 kb or 3 kb, as indicated, when amplification occurs from spliced RNA rather than contaminating DNA.

Figure 37:
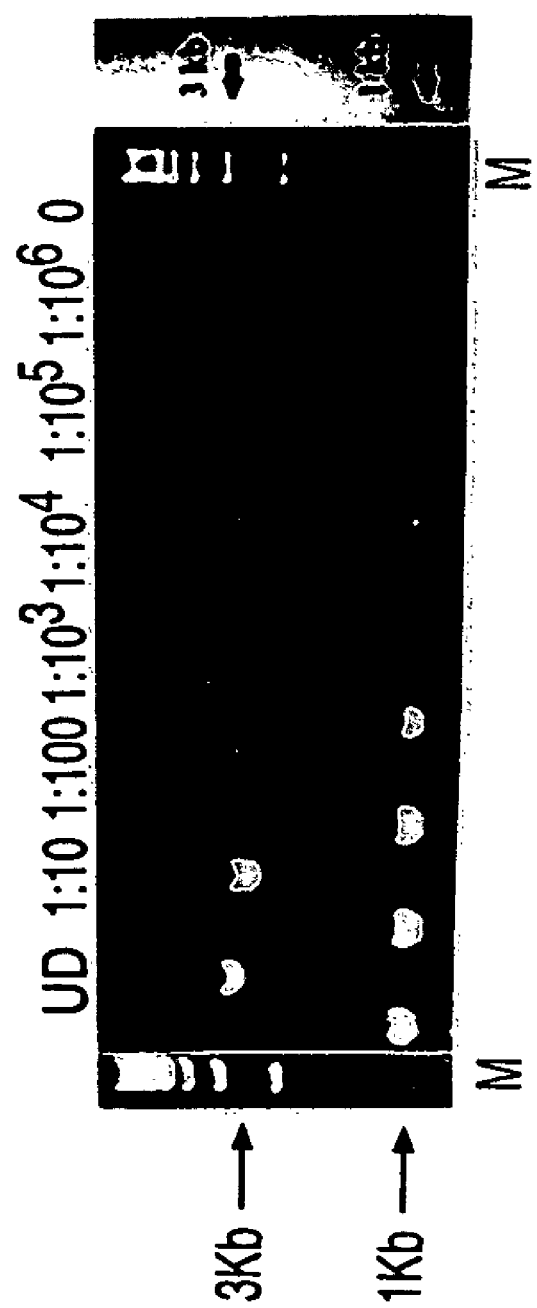
FIG. 37. Enhancement of RT-PCR with P. furiosus PEF. A portion of the EGF receptor sequence was amplified from HepG$_2$ total RNA using the 2-step RT-PCR protocol described with the following additions. 1 µl of a cDNA synthesis reaction was added to 50 µl PCR reactions containing 5U Pfu DNA polymerase, 1 µM antisense primer (5' GAG-TTA-AAT-GCC-TAC-ACT-GTA-TCT) (SEQ ID NO: 29), 1 µM sense primer [5' CAG-GAC-TCA-GAA-GCT-GCT-ATC-GAA (SEQ ID NO: 30) (1 kb product) or 5'CTG-CAC-GTG-CCC-TGT-AGG-ATT-TGT (SEQ ID NO: 31) (3 kb product)]. 1 µl of buffer (0) or 1 µl of a PEF-containing heparin sepharose fraction (SCS #37 H.S. #75; prep. 4; ≈10 ng/µl PEF) was added undiluted (UD) or diluted 1:10 to 1:10$^6$ (as indicated). PCRs were conducted in cloned Pfu PCR buffer, containing 3 mM MgSO$_4$.

The PEF concentration which gives optimal performance was determined by titrating PEF preparation 3 (S-200 purified) and preparation 4 (heparin sepharose fraction) in the 2-step RT-PCR procedure described here. With PEF preparation 4, significant increase in the yield of the 1 kb product was observed when 0.001-1 µl was added (10 pg-10 ng PEF) (FIG. 37). Synthesis of the 3 kb product was significantly enhanced when 0.1-1 µl (1-10 ng PEF) of preparation 4 was added. With PEF preparation 3, significant increases in the yields of both the 0.6 kb and the 3 kb products were observed for all amounts tested in the range of 0.002-0.1 µl (1-50 ng).

4. Enhancement of Seamless™ Cloning Protocol

Figure 38:
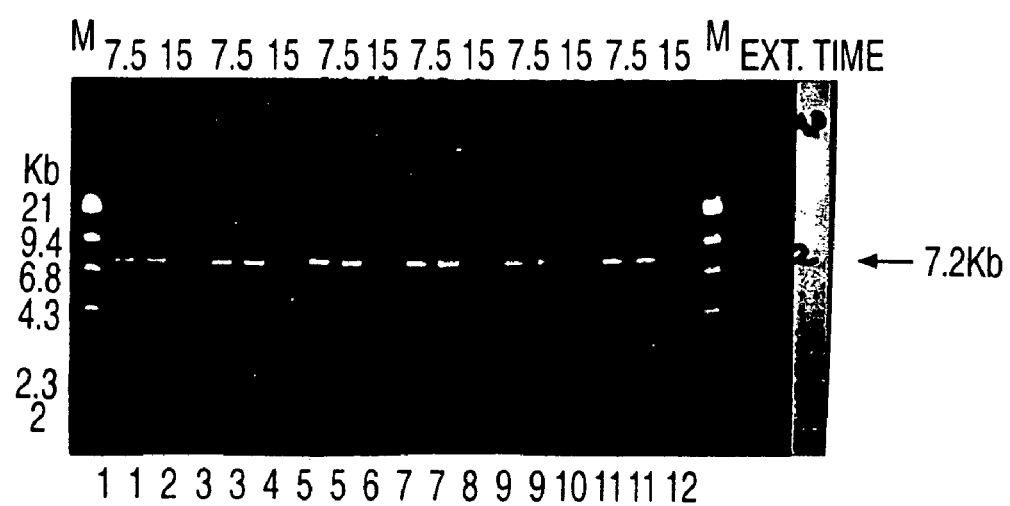
FIG. 38. Enhancement of Pfu DNA polymerase-based Seamless Cloning with P. furiosus PEF. 20 ng of plasmid was amplified as described in the Seamless Cloning kit protocol in the absence (lanes 2, 4, 6, 8, 10, 12) or presence (duplicate lanes 1, 3, 5, 7, 9, 11) of S200-purified P. furiosus PEF (prep. 3; 550 ng/µl), diluted 1:100. A 7.2 kb target was amplified with 6 different primer pairs (each set of 3 lanes). An extension time of 7.5 minutes was used for PEF-containing reactions, while an extension time of 15 minutes was used for reactions lacking PEF.

Seamless Cloning was performed using Stratagene's Seamless™ Cloning kit (Stratagene; La Jolla, Calif., 1997/1998 Stratagene Catalog, specifically incorporated herein by reference), following the recommended protocol. The effect of *P. furiosus* PEF on the efficiency of Seamless Cloning is shown in FIG. 38. Increased yield of a 7.2 kb PCR product was observed when 5 ng of S-200 purified PEF (prep. 1) was added to 50 µl PCR reactions containing 2.5U Pfu DNA polymerase and methyl dCTP. Amplifications conducted in the presence of PEF utilized 1 min. per kb extension times. In the absence of PEF, very little PCR product was generated despite the use of longer 2 min./kb extension times.

5. Enhancement of Linear Amplification Reactions: QuikChange™ Mutagenesis Protocol Site-specific mutagenesis can be accomplished efficiently with double-stranded DNA templates using a linear amplification-based strategy employing Pfu DNA polymerase (QuikChange™ Site-Directed Mutagenesis Kit; Stratagene; La Jolla, Calif., 1997/1998 Stratagene Catalog, specifically incorporated herein by reference). PCR primers containing the desired mutation(s) are designed to anneal to the same site on opposite strands. Primer extension reactions are conducted with a thermostable DNA polymerase (e.g. Pfu DNA polymerase) at temperatures which allow efficient synthesis in the absence of strand displacement activity (68° C.). The amplification product is treated with DpnI to digest the parental methylated plasmid DNA and the resulting gapped, double-stranded DNA is then transformed into competent *E. coli* cells. Mutant clones are identified by DNA sequencing.

In evaluating *P. furiosus* PEF, mutagenesis was conducted using Stratagene's Quik Change mutagenesis kit, except that both recombinant and native Pfu DNA polymerase were used in the kit-supplied reaction buffer. The effect of *P. furiosus* PEF on the efficiency of QuikChange mutagenesis is shown in FIG. 39. The addition of 0.04 to 4 ng of PEF of PEF prep. 2 (heparin sepharose fraction lot 36 H.S. #78; 40 ng/µl) to 50 µl reactions increased the number of transformants generated by native and cloned Pfu DNA polymerases, while retaining mutation frequencies of 90-97%. Optimal results were obtained with 0.4 ng of PEF, which gave 7.5-fold and 5.3-fold increases in the number of mutant colonies generated with native and cloned Pfu DNA polymerase, respectively.

The use of PEFs in the QuikChange™ mutagenesis protocol corresponds to the use of PEFs in other linear amplification reactions known in the art, such as cycle sequencing reactions, primer extension reactions, and the like. PEFs can be employed in any linear amplification method to enhance the activity of the polymerase used. For example, the effect of Pfu PEF on cycle sequencing can be evaluated by comparing the quality and length of sequencing ladders generated with a polymerase, for example exo⁻Pfu DNA polymerase, in the absence and in the presence of PEF. A number of different cycle sequencing reactions, known to one skilled in the art, can be used in combination with the PEF complexes and proteins of this invention to enhance polymerase activity. In addition, primer extension reactions can also be enhanced with the use of PEFs. Numerous primer extension reactions are known in the art.

EXAMPLE 16

Enhancing Titer of PEF

The nucleic acid replication enhancing activity of several different preparations of Pfu PEF have been evaluated in PCR, PCR-related applications, linear amplification-based applications, mutagenesis applications, cycle sequencing applications, and primer extension applications. One skilled in the art will appreciate that similar methods to optimize the use of any PEF, such as those specifically discussed herein, are apparent from the disclosure herein. A sample of substantially homogeneous PEF (e.g. S200-purified) enhances the performance of Pfu DNA polymerase in PCR amplification reactions when added at concentrations spanning a 10,000-fold range (0.09-900 ng/100 µl). The highest yields of amplified product are observed in the presence of ≈1 to 100 ng of P50. The addition of excess PEF (≧900 ng/100 µl, where protein concentration was determined by the silver-staining intensity of the P50 band as compared to known protein standards) or very low PEF concentrations (<9 pg/100 μl) in a PCR reaction resulted in lower PCR product yield.

Figure 10:
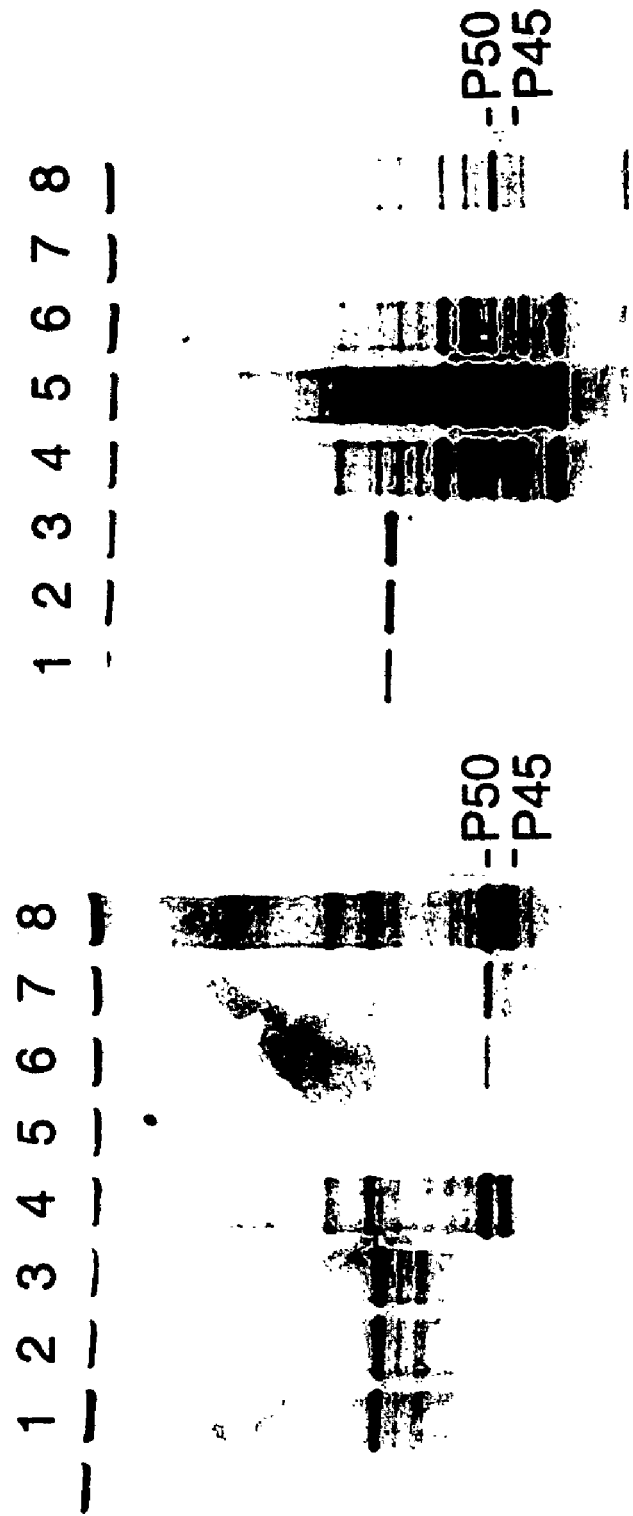
FIG. 10. SDS-PAGE analysis of *P. furiosus* PEF preparations. In the left panel, the following samples were subject to SDS-PAGE silver stain analysis, conducted as described: cloned Pfu DNA polymerase lot#24A (56 ng/μl) [lanes 1-3, 1 μl, 2 μl, 4 μl]; S200 purified *P. furiosus* PEF fraction #46 (prep. 1 from SCS #38) [lane 4- 2 μl]; S200 purified *P. furiosus* PEF pool fractions #47-48 (550 ng/μl; prep. 3 from SCS #38) [lanes 5-8, 0.1 μl, 0.2 μl, 0.4 μl, 1 μl]. In the right panel, the following samples were run: cloned Pfu DNA polymerase lot#24A (56 ng/μl) [lanes 1-3, 1 μl, 2 μl, 4 μl]; microcon 30-concentrated SCS #36 heparin sepharose fraction #78 (prep. 2) [lanes 4-6, 1 μl, 2 μl, 0.4 μl]; SCS #37 heparin sepharose fraction #75 (prep. 4) [lanes 7-8, 1 μl, 5 μl].
Figure 11A:
FIG. 11. PDVF blots of *P. furiosus* PEF. PEF-containing heparin sepharose fractions (from SCS #37 Pfu purification) were concentrated and aliquots electrophoresed in 8 or 9 lanes on 4-20% SDS-PAGE gels as described. The samples were boiled for 3 min. prior to loading to recover the 50 kD monomeric PEF (top) or were loaded in the absence of heat treatment to recover the >250 kD aggregate (bottom). The proteins were transferred to PDVF filters (BioRad) and stained with Amido black.
Figure 11B:
Figure 40:
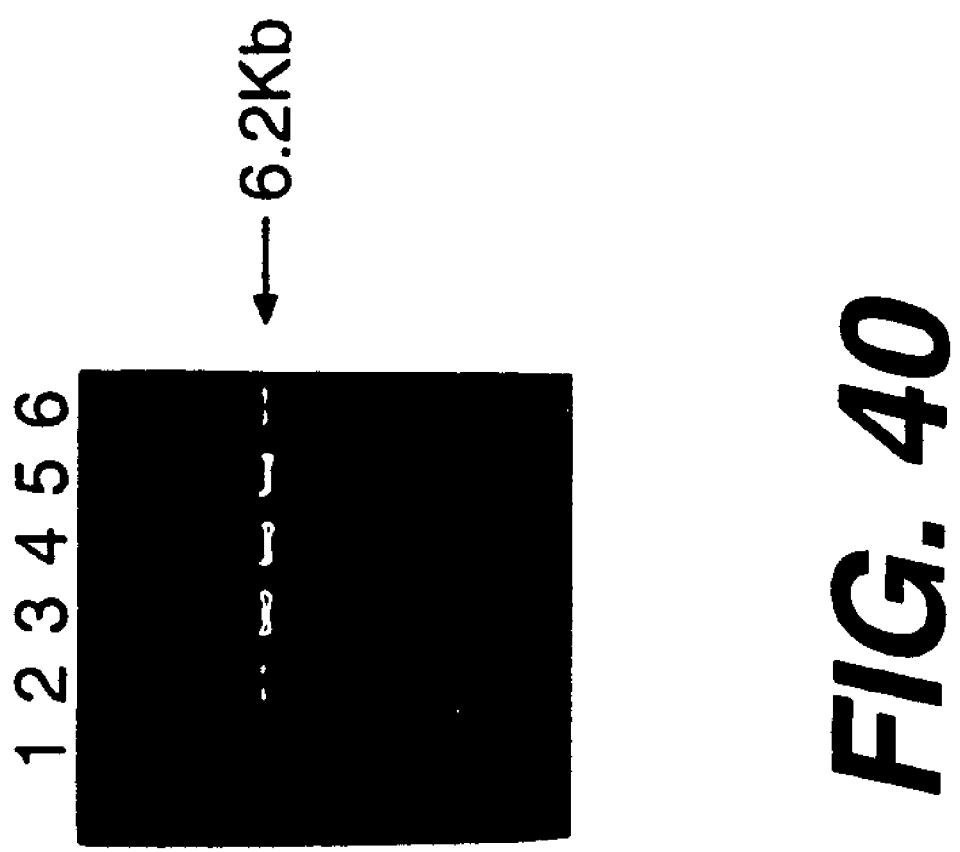
FIGS. 40 and 41. PCR enhancing activity of S200-purified P. furiosus PEF. PCR enhancing activity was measured in duplicate assays using the 6.2 kb test system described in Example 1.
Figure 41:
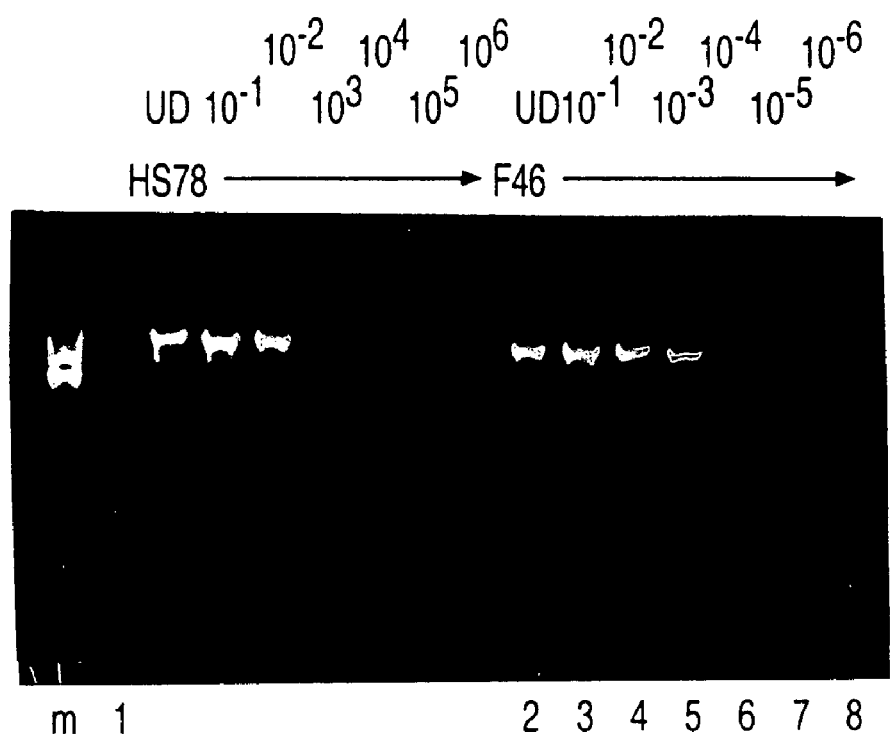

The relative purity and PEF content of 4 preparations was examined by SDS-PAGE analysis (FIG. 10). Preparations 1 and 3 consist of S200-purified PEF of >95% homogeneity, while preparations 2 and 4 consist of concentrated heparin sepharose fractions of 10-20% homogeneity. The PCR enhancing titer of S200-purified $P.$ $furiosus$ PEF (prep. 1; FIGS. 40 and 41) was determined using the F432-21/R6656-20/λAA742 primer-template system described in example 1. This preparation is approximately 95% pure, contains <0.001U/μl DNA polymerase activity, and ≈225 ng/μl PEF. PCR enhancing activity was found to be optimal when 0.004-0.4 μl (0.9-90 ng) of homogeneous $P.$ $furiosus$ PEF was added to 100 μl PCR reactions containing 2.5U of Pfu DNA polymerase. Reduced, but significant, PCR product yield was observed when 4 μl (900 ng) or 0.0004 μl (0.09 ng) of the S200-purified protein was added (FIG. 40). In a second identical experiment, significant enhancement was noted when 0.004-4 μl was added, and very little improvement was noted with 0.0004 μl (FIG. 41).

Figure 42:
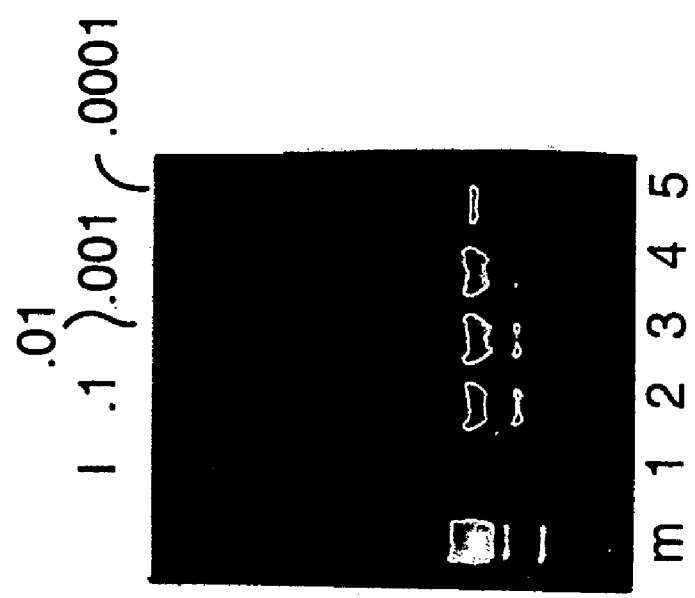
FIGS. 42 and 43. PCR enhancing activity of heparin sepharose-purified P. furiosus PEF. PCR enhancing activity was measured using the 6.2 kb test system described. The PEF fraction (≈40 ng/µl; prep. 2 in text) was diluted in 1× cloned Pfu PCR buffer.
Figure 43:
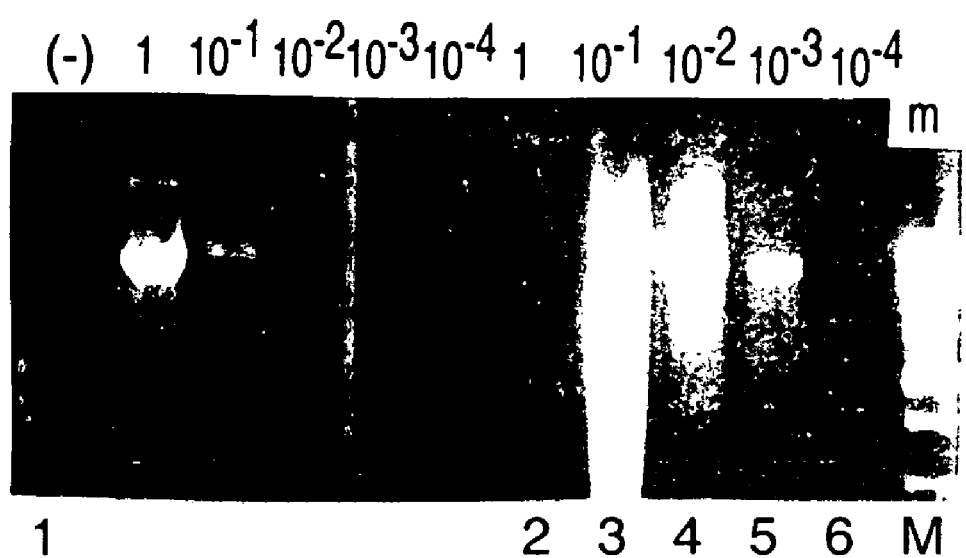

The PCR enhancing titer of PEF preparation 2 was also determined (FIGS. 42-43). Preparation 2 consisted of a concentrated (Microcon-30) heparin sepharose fraction, in which $P.$ $furiosus$ PEF made up approximately 10% of the total protein and was present at approximately 40 ng/μl. Enhanced PCR product yield was observed when 0.0002-2 μl (0.008-8 ng) of the column fraction was added to 100 μl PCR reactions containing 2.5U of Pfu DNA polymerase, with greatest enhancements observed in the range of 0.002-2 μl (0.08-8 ng) (FIG. 42). In a second identical experiment, enhanced PCR product yield was observed when 0.004-0.04 μl (0.16-1.6 ng) of PEF preparation 2 was added to 2.5U of DNA polymerase per 100 μl PCR reaction (FIG. 43). No PCR product was observed in the presence of 4 μl (160 ng) or 0.0004 μl (0.016 ng) of the column fraction, while a smear was generated when 0.4 μl (16 ng) of the column fraction was added to PCR. Smeary PCR products were also noted previously when 1 μl of heparin sepharose fractions containing the highest concentrations of PEF are added to PCRs (e.g., lot 37 H.S. fractions 69-81 in FIG. 44; PEF prep. 2 in FIG. 31).

In summary, sunstantially homogeneous $P.$ $furiosus$ PEF enhances the performance of Pfu DNA polymerase in test PCR amplifications when added at concentrations spanning a 10,000-fold range (0.09-900 ng/100 μl). The highest yields are observed in the presence of ≈1 to 100 ng of PEF. The addition of excess PEF (≧900 ng/100 μl) or PEF <9 pg/100 μl PCR reaction, was found to give reduced performance (lower PCR product yield). Partially-purified PEF samples (heparin sepharose column fractions) also appears to enhance PCR product yield over a fairly broad range of PEF concentrations. With the column fraction analyzed here, highest yields of PCR were obtained in the range of 0.08 ng to 8 ng. The addition of higher amounts of the column fraction resulted in smearing (16-40 ng) or lack of enhancement (160 ng).

Inhibition of PCR enhancement at high concentrations of PEF appears to occur irrespective of the purity of the PEF sample. The addition of higher concentrations of homogeneous PEF (≧900 ng) resulted in lower yields of PCR product than could be obtained with <900 ng PEF. Heparin sepharose fractions of 10-20% purity also gave reduced PCR product yields when high amounts of PEF were added. Up to 8 ng of PEF in prep. 2 (H.S. #78 fraction) could be added before smearing or inhibition occurred. The discrepancy between the amount of PEF which is inhibitory in homogeneous preparations (≧900 ng), as compared to partially-purified column fractions (>16 ng), suggests that additional protein or DNA contaminants may be present in the heparin sepharose fractions.

Figure 44B:
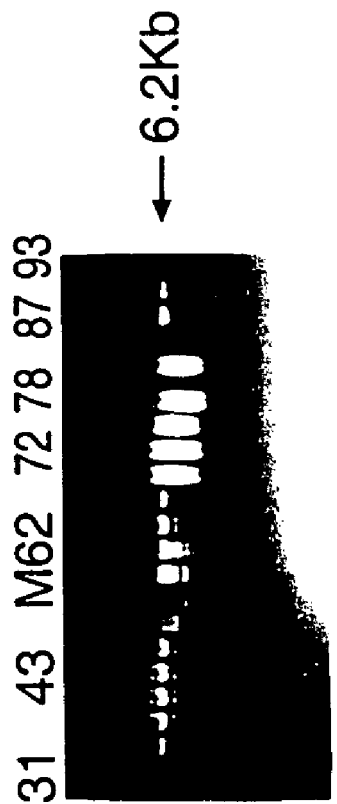
FIG. 44 PCR enhancing activity of heparin sepharose column fractions. The PCR enhancing activity contained in 1 µl of each column fraction (fractions 1-93 from FIG. 32; numbered at top) was measured using the assay 6.2 kb primer-template PCR described in Example 1. Fractions 50-61 contained the peak of Pfu DNA polymerase activity and were excluded from analysis.
Figure 44A:
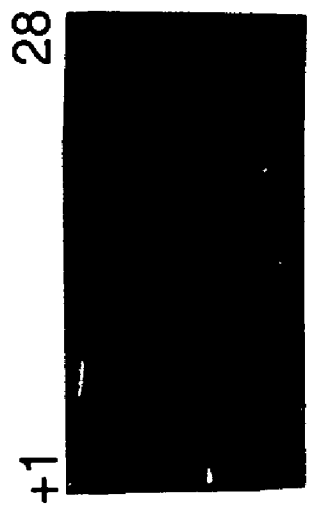

Examination of heparin sepharose fractions revealed that $P.$ $furiosus$ PEF elutes just after the major peak of Pfu DNA polymerase activity (e.g., fractions 50-61 in FIG. 32). SDS-PAGE analysis showed that the highest levels of the >250 kD PEF appeared in fractions 63-78 from the native Pfu DNA polymerase purification (FIG. 32). PCR enhancing activity was observed in fractions 37-90 (FIG. 44). Discrete PCR product bands were generated with fractions 37-48 and 87-90, which contain very low levels of PEF. Interestingly, DNA smears were generated with fractions 69-81 (FIG. 44), which contain the highest levels of PEF and no detectable Pfu DNA polymerase. These results are consistent with the hypothesis that $P.$ $furiosus$ PEF acts as an inhibitory substance when present at high concentrations. However, concentrations high enough to adversely effect polymerization and PCR reactions can easily be determined through the methods and assays described herein. Thus, one skilled in the art can avoid concentrations of PEF that inhibit polymerase activity or PCR reactions without undue experimentation.

As observed with PCR, inhibition during linear amplification protocols was noted with high concentrations of PEF-containing heparin sepharose fractions (FIG. 39). The addition of 40 ng (1 μl prep. #2) of PEF to QuickChange™ reactions resulted in reduced yield of amplification product, as visualized by a reduction in the ethidium bromide-staining intensity of DNA bands on agarose gels. Reduced yield accompanied a 1.8 to 2.8-fold reduction in the number of transformants and a slight, but reproducible, decrease in mutation frequency.

A possible and the most likely explanation for inhibition by homogenous PEF preparations is depletion of dCTP. In Example 11, section 1, we demonstrated that PEF can utilize dCTP as a substrate, although much less efficiently than dUTP. At high PEF concentrations it is possible that enough dCTP is hydrolyzed by PEF to drop the dCTP levels below what is required for optimal DNA synthesis. It is also possible that moderate to high levels of PEF could alter dCTP levels enough to affect DNA polymerase misincorporation rates. Alternatively, contaminants in the substantially homogenous PEF preparations may also cause the inhibition and may only be present in sufficient concentrations when high concentrations of PEF are used.

Each of the references referred to herein can be relied on by one skilled in the art in making and using embodiments of the invention. In addition, each reference is specifically incorporated, in its entirety, into this disclosure.

The sequence listing information that follows incorporates the sequences in prior U.S. patent application Ser. No. 08/822,744, which is specifically herein by reference. The sequence information from any one sequence or any combination of sequences can be translated into a computer readable medium by those of skill in the art. Furthermore, the sequences of the specific clones or plasmids described or identified herein can be easily determined and used in a computer readable medium by one skilled in the art.

What is claimed is:

1. A method of enhancing a nucleic acid polymerase reaction comprising:
    (a) forming a nucleic acid polymerase reaction composition comprising:
        (i) a nucleic acid
        (ii) at least one nucleic acid polymerase selected from a Pfu DNA polymerase, an exo⁻Pfu DNA polymerase, a Pwo DNA polymerase, a Vent DNA polymerase, a Deep Vent DNA polymerase, a JDF3 DNA polymerase, and an ES4 DNA polymerase, and
        (iii) a P45 protein, wherein the P45 protein is in monomeric, dimeric, or multimeric form, and wherein the P45 protein is produced from a cell containing a DNA construct comprising a sequence encoding polymerase enhancing factor protein P45 operably linked to an expression vector, and wherein the P45 protein comprises the sequence of SEQ ID NO:72, and
    (b) incubating the nucleic acid polymerase reaction composition under conditions allowing a nucleic acid polymerase reaction, wherein the P45 protein increases rate, fidelity and/or yield of the nucleic acid polymerase reaction.

2. A method of enhancing a nucleic acid polymerase reaction as claimed in claim 1, wherein the P45 protein is present in a polymerase enhancing factor complex.

3. A method for controlling the activity of a polymerase in a nucleic acid polymerase reaction, comprising:
    (a) forming a nucleic acid polymerase reaction composition comprising:
        (i) a nucleic acid
        (ii) at least one nucleic acid polymerase selected from a Pfu DNA polymerase, an exo⁻Pfu DNA polymerase, a Pwo DNA polymerase, a Vent DNA polymerase, a Deep Vent DNA polymerase, a JDF3 DNA polymerase, and an ES4 DNA polymerase, and
        (iii) a polymerase enhancing factor activity, wherein the polymerase enhancing factor activity comprises the sequence of SEQ ID NO:72, and wherein the the polymerase enhancing activity changes the amount of dUTP present or generated during the reaction, and (b) incubating the nucleic acid polymerase reaction composition under conditions allowing a nucleic acid polymerase reaction, wherein changing the amount of dUTP present or generated during the reaction controls the activity of the polymerase in the polymerization reaction.

4. A method according to claim 3, wherein the polymerase enhancing factor activity comprises a P45 protein, wherein the P45 protein is in monomeric, dimeric, or multimeric form, and wherein the P45 protein is produced from a cell containing a DNA construct comprising a sequence encoding polymerase enhancing factor protein P45 operably linked to an expression vector.

* * * * *